US007632468B2

(12) United States Patent
Barski et al.

(10) Patent No.: US 7,632,468 B2
(45) Date of Patent: Dec. 15, 2009

(54) RETAINING CLIP FOR REAGENT TEST SLIDES

(75) Inventors: Stanislaw Barski, Limerick, ME (US); Joseph Michael Chiapperi, Rochester, NY (US); Mark Elliott Deacon, Rochester, NY (US); Mark R. Dumont, Saco, ME (US); Mark Weston Pierson, Saco, ME (US); Timothy Robert Keegan, Wells, ME (US); Mark Benno Loeser, Rochester, NY (US); Gerald George Meiler, Ontario, NY (US); Ross Bryan Goldman, Scarborough, ME (US); Carl Russell Rich, Falmouth, ME (US); Richard James Versluys, Spencerport, NY (US)

(73) Assignees: IDEXX Laboratories, Inc., Westbrook, ME (US); Ortho-Clinical Diagnostics, Inc., Rochester, NY (US)

( * ) Notice: Subject to any disclaimer, the term of this patent is extended or adjusted under 35 U.S.C. 154(b) by 128 days.

(21) Appl. No.: 11/002,599

(22) Filed: Dec. 2, 2004

(65) Prior Publication Data

US 2005/0238541 A1    Oct. 27, 2005

Related U.S. Application Data

(60) Provisional application No. 60/526,885, filed on Dec. 4, 2003, provisional application No. 60/526,884, filed on Dec. 4, 2003.

(51) Int. Cl.
*B01L 3/00* (2006.01)
*G01N 21/00* (2006.01)
*G01N 31/00* (2006.01)
*B01L 9/00* (2006.01)

(52) U.S. Cl. .......... 422/102; 422/58; 422/60; 422/61; 422/63; 422/64; 422/65; 422/66; 422/67; 422/99; 422/104

(58) Field of Classification Search ........ 206/126, 206/159, 340, 562, 468, 467; 422/58, 99, 422/104
See application file for complete search history.

(56) References Cited

U.S. PATENT DOCUMENTS

| 2,630,219 | A | 3/1953 | Pierce |
| 2,919,021 | A | 12/1959 | Robinson, et al. ........... 353/118 |
| 2,942,365 | A | 6/1960 | Badalich |
| 3,133,332 | A | 5/1964 | Johnson |
| 3,244,273 | A | 4/1966 | Wiklund |

(Continued)

*Primary Examiner*—Jill Warden
*Assistant Examiner*—Neil Turk
(74) *Attorney, Agent, or Firm*—Gerald T. Bodner

(57) ABSTRACT

A retaining clip for retaining reagent test slides in a stacked arrangement includes a first assembly having a first cover plate and at least two parallel, co-planar rails extending transversely from an inner surface of the first cover plate. A second assembly includes a second cover plate, and a rail receiving platform extending transversely from an inner surface of the second cover plate. The first cover plate and the second cover plate define between them a space for receiving the plurality of reagent test slides. The rails of the first assembly include ratchet teeth, and the rail receiving platform of the second assembly includes pawls. The pawls engage the ratchet teeth to prevent the separation of the first assembly and the second assembly and to securely but removably hold the plurality of reagent test slides in a stacked arrangement between the first and second cover plates.

27 Claims, 42 Drawing Sheets

U.S. PATENT DOCUMENTS

| | | | |
|---|---|---|---|
| 3,416,250 A | 12/1968 | Schweers | |
| 3,467,251 A | 9/1969 | Janss et al. | |
| 3,552,846 A | 1/1971 | Hansen | |
| 3,600,762 A * | 8/1971 | Rissberger | 206/53 |
| 3,624,873 A | 12/1971 | Frey | |
| 3,701,558 A | 10/1972 | Baker | |
| 3,710,975 A | 1/1973 | Jansen | 220/31 |
| 3,711,905 A | 1/1973 | Eckerdt et al. | 24/263 |
| 3,756,393 A | 9/1973 | Markwitz et al. | 206/62 |
| 3,992,158 A | 11/1976 | Przybylowicz et al. | 23/253 |
| 4,053,381 A | 10/1977 | Hamblen et al. | 204/195 |
| 4,077,515 A | 3/1978 | Shoberg | 206/456 |
| 4,081,119 A * | 3/1978 | Messmore | 206/454 |
| 4,114,166 A | 9/1978 | Driscoll et al. | 354/76 |
| 4,151,931 A | 5/1979 | Scherer et al. | 221/226 |
| 4,159,875 A | 7/1979 | Hauser | 356/244 |
| 4,230,757 A | 10/1980 | Toner | 428/137 |
| 4,437,566 A * | 3/1984 | Szahler | 206/1.5 |
| 4,440,301 A | 4/1984 | Intengan | 206/456 |
| 4,568,519 A | 2/1986 | Hamilton et al. | 422/64 |
| 4,584,275 A | 4/1986 | Okano et al. | 435/290 |
| 4,589,551 A | 5/1986 | Hellon | 206/456 |
| 4,635,791 A | 1/1987 | Jackson et al. | 206/210 |
| 4,689,858 A | 9/1987 | Barber | 24/17 B |
| 4,696,396 A | 9/1987 | Samuels | 206/339 |
| 4,737,344 A | 4/1988 | Kolzumi et al. | 422/100 |
| 4,766,714 A | 8/1988 | Sugaya | 53/242 |
| 4,776,689 A | 10/1988 | Maclay | 353/111 |
| 4,826,659 A | 5/1989 | Akisada | 422/63 |
| 4,828,111 A | 5/1989 | Rosenberg | 206/456 |
| 4,855,109 A | 8/1989 | Muraishi et al. | 422/63 |
| 4,857,272 A | 8/1989 | Sugaya | 422/65 |
| 4,960,224 A | 10/1990 | Boenisch | 206/456 |
| 5,053,198 A | 10/1991 | Quenin | 422/64 |
| 5,080,869 A * | 1/1992 | McCormick | 422/102 |
| 5,081,038 A | 1/1992 | Sugaya et al. | 436/46 |
| 5,089,229 A | 2/1992 | Heidt et al. | 422/64 |
| 5,090,568 A | 2/1992 | Tse | 206/456 |
| 5,102,624 A | 4/1992 | Muraishi | 422/64 |
| 5,119,573 A | 6/1992 | Dentella | 40/367 |
| 5,147,042 A | 9/1992 | Levy | 206/456 |
| 5,154,889 A | 10/1992 | Muraishi | 422/65 |
| 5,176,257 A | 1/1993 | Levy | 206/456 |
| 5,250,262 A | 10/1993 | Heidt et al. | 422/64 |
| 5,265,726 A | 11/1993 | Johnson | 206/456 |
| 5,292,000 A | 3/1994 | Levy | 206/456 |
| 5,297,383 A | 3/1994 | Mackay | 52/712 |
| 5,336,467 A | 8/1994 | Heidt et al. | 422/64 |
| 5,358,019 A | 10/1994 | Sumner, III | 150/147 |
| 5,358,692 A * | 10/1994 | Reynolds | 422/104 |
| 5,507,388 A | 4/1996 | Kildal et al. | 206/459.5 |
| 5,538,688 A | 7/1996 | Tezuka et al. | 422/64 |
| 5,553,720 A * | 9/1996 | Dardashti | 211/40 |
| 5,599,505 A | 2/1997 | Fujisaki et al. | 422/104 |
| 5,617,973 A | 4/1997 | Seto et al. | 221/56 |
| 5,653,942 A | 8/1997 | Terashima et al. | 422/63 |
| 5,674,454 A | 10/1997 | Karl et al. | 422/63 |
| 5,718,329 A | 2/1998 | Ippolito et al. | 206/38 |
| 6,006,911 A | 12/1999 | Levy | 206/456 |
| 6,713,018 B2 | 3/2004 | Sugaya et al. | 422/58 |
| 2003/0186647 A1 | 10/2003 | Ikeda | 436/48 |
| 2005/0123444 A1 | 6/2005 | Tomasso et al. | 422/64 |

* cited by examiner

FIG. 21
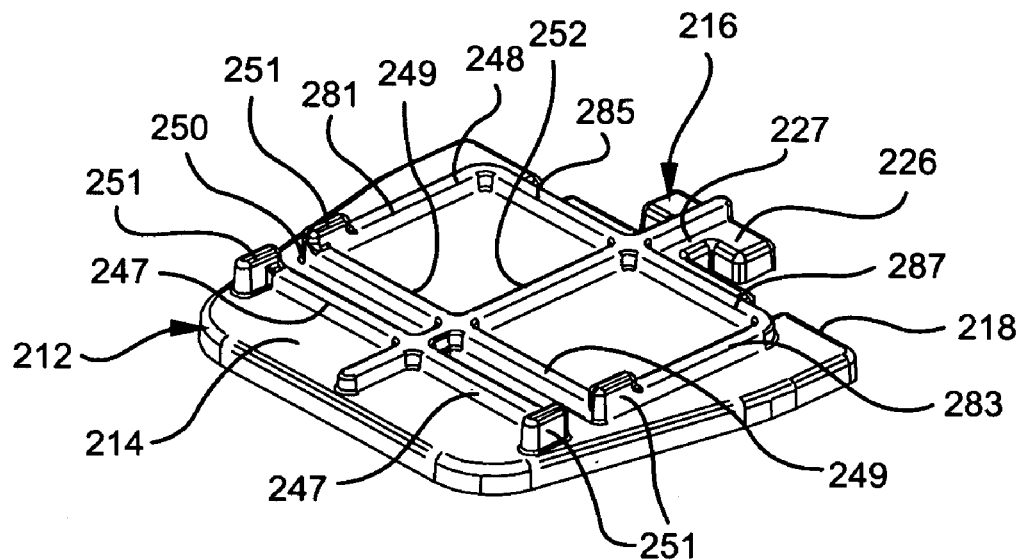
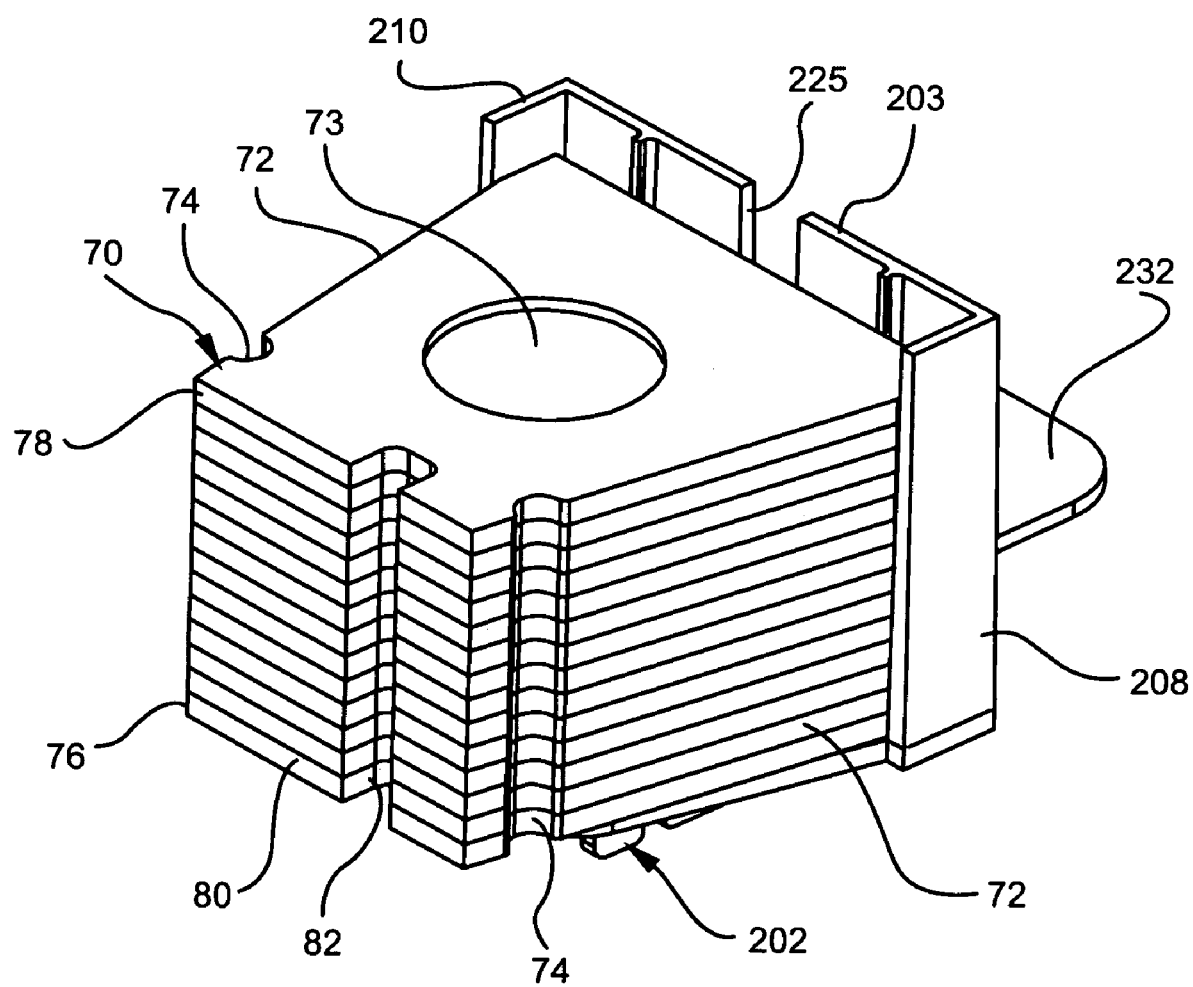

FIG. 22
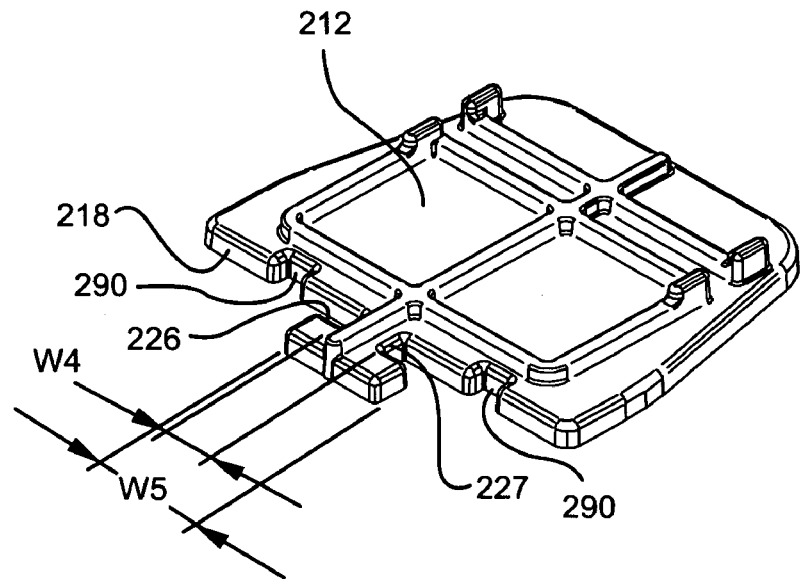
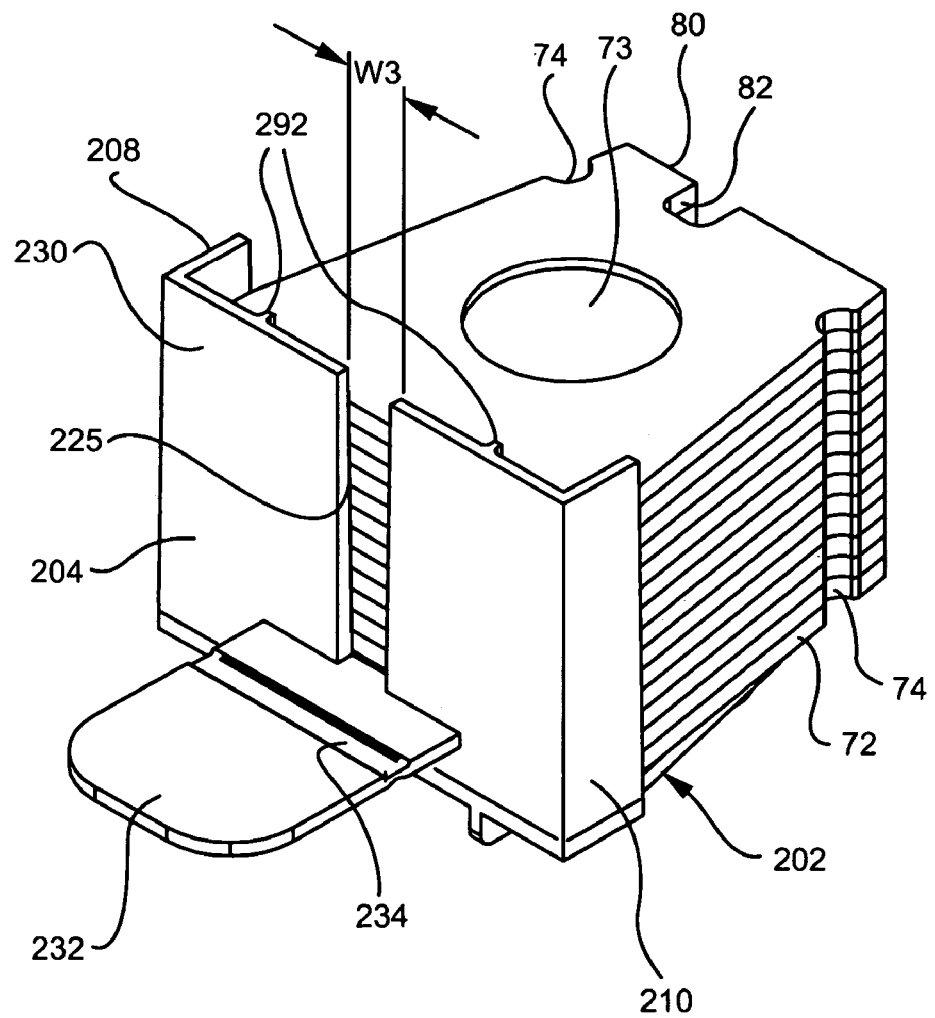

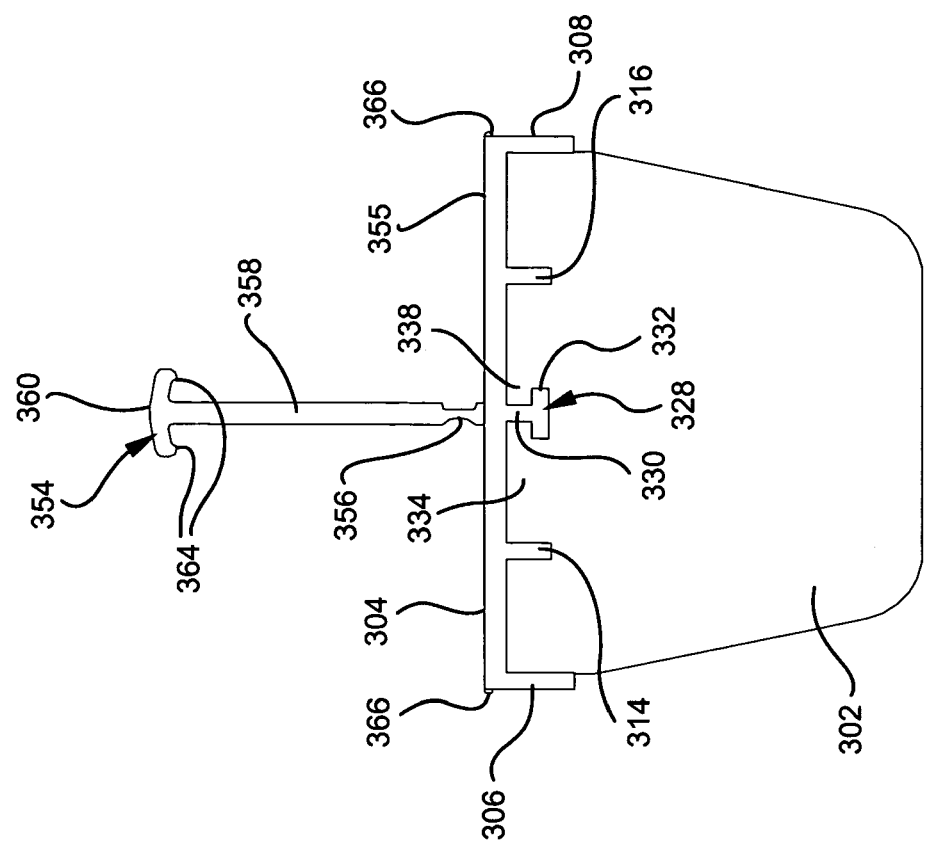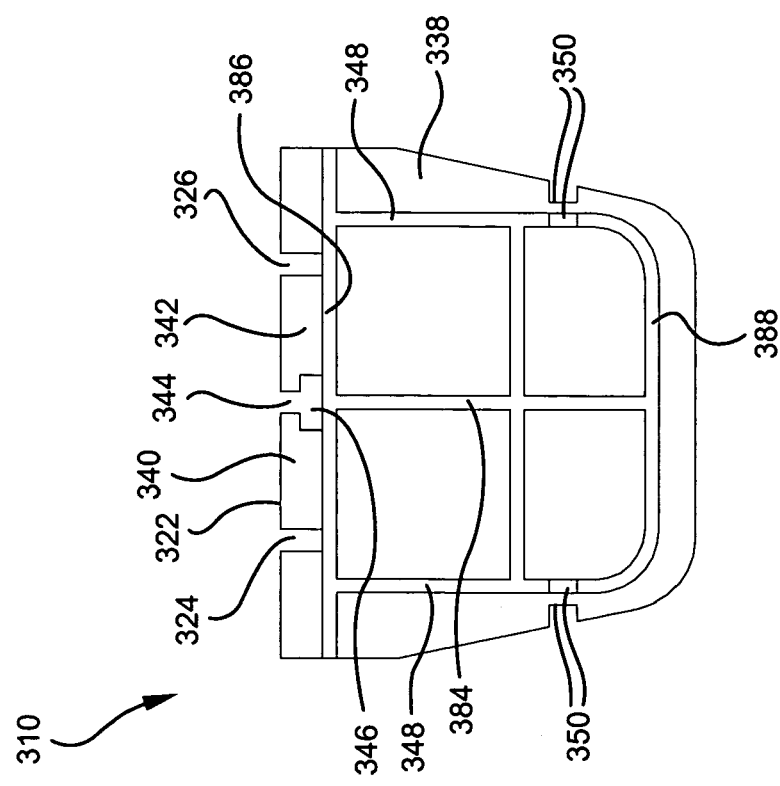

RETAINING CLIP FOR REAGENT TEST SLIDES

CROSS-REFERENCE TO RELATED APPLICATIONS

This application is related to U.S. provisional patent application Ser. No. 60/526,885, filed on Dec. 4, 2003, and entitled "Retaining Clip For Reagent Test Slides", and to U.S. provisional patent application Ser. No. 60/526,884, filed on Dec. 4, 2003, and entitled "Reagent Test Slide Injector Mechanism Having a Scotch Drive and Rotatable Turntable Having a Geneva Drive for a Chemical Analyzer", the disclosure of each of which is incorporated herein by reference. This application claims benefit of priority under 35 U.S.C. §119 to the aforementioned related provisional applications.

BACKGROUND OF THE INVENTION

1. Field of the Invention

The present invention relates to chemical analyzers using dry chemistry reagent test slides, and more particularly relates to holding and storage devices for such reagent test slides prior to use and upon insertion of the test slides in a chemical analyzer.

2. Description of the Prior Art

Automated systems for carrying out quantitative chemical analysis of fluid samples have increasingly been developed for use with essentially dry, analytical elements which are preferably in the form of test slides. The test slides are formed as a multi-layer element containing the necessary reagents for reaction with components of a biological fluid, such as blood serum, deposited thereon. Certain reactions colorimetrically or fluorescently produce a change in optical density which is sensed by a reflectometer or other optical device, the amount of light reflected from the element varying in accordance with the reaction and being indicative of the amount of a particular component present in the fluid. An example of such a reagent test slide is disclosed in U.S. Pat. No. 4,053,381, which issued on Oct. 11, 1977 to Hamblen et al., and in U.S. Pat. No. 3,992,158, which issued on Nov. 16, 1976 to Przybylowicz et al., the disclosures of which are incorporated herein by reference. A chemical analyzer which uses such reagent test slides is described in U.S. Pat. Nos. 5,089,229, 5,250,262 and 5,336,467, each of which issued on Feb. 18, 1992, Oct. 5, 1993, and Aug. 9, 1994, respectively, to Heidt et al., the disclosures of which are incorporated herein by reference.

Such typical reagent test slides must be carefully handled and stored during and prior to use in the chemical analyzer. The analyte deposited on the film of the test slide must remain free from contaminants and must not be exposed to other test slides having a different chemical reagent deposited thereon. A user of the chemical analyzer must take care in handling the reagent test slides to ensure that fingers do not touch the film portion containing the dry analyte. Additionally, once the test slide is removed from its sealed container, it should be used or otherwise loaded immediately in the chemical analyzer, as the analyte on the film portion of the test slide is now exposed to contaminants in the environment which may corrupt the tests performed by the chemical analyzer.

OBJECTS AND SUMMARY OF THE INVENTION

It is an object of the present invention to provide a holding device for retaining a plurality of reagent test slides.

It is another object of the present invention to provide a retaining clip for holding a plurality of reagent test slides in a stacked arrangement.

It is a further object of the present invention to provide a retaining clip which is adaptable for holding one or more test slides in a stacked arrangement.

It is still another object of the present invention to provide a retaining clip for holding a plurality of test slides which avoids the need for the user to handle the edges of the test slides when inserting them into a chemical analyzer.

It is yet a further object of the present invention to provide a retaining clip for a plurality of test slides which minimize the contamination of the slides from the environment or other sources.

In accordance with one form of the present invention, a clip for retaining a plurality of reagent test slides in a stacked arrangement includes a first assembly which has a cover plate and at least one rail extending transversely from the cover plate, and a second assembly which also includes a cover plate and a rail receiving platform extending transversely from the cover plate. The rail receiving platform of the second assembly slidably receives the at least one rail of the first assembly when the first assembly is mated with the second assembly. The two cover plates define between them a space for receiving the plurality of reagent test slides in a stacked arrangement. Preferably, the at least one rail includes ratchet teeth, and the rail receiving platform includes a pawl which lockingly engages the ratchet teeth to prevent the separation of the first assembly and the second assembly and to hold the plurality of reagent test slides between the two cover plates.

In another embodiment of the present invention, the retaining clip includes a middle plate having opposite first and second sides and a slot formed through the thickness thereof, a first cover plate extending outwardly from the first side of the middle plate and which preferably has an extended portion that passes through the slot of the middle plate, and a second cover plate which is joined to the middle plate and extends outwardly from the first side of the middle plate. The first cover plate and the second cover plate are in overlying relationship with each other to define therebetween a space for receiving the plurality of reagent test slides in a stacked arrangement. Preferably, the retaining clip includes a foldable handle extending from the second side of the middle plate. When folded, the handle partially overlies the surface of the second side of the middle plate to provide the retaining clip with a compact size for shipping or when not being handled.

In another form, the retaining clip of the present invention includes a middle plate having a first side and a second side opposite the first side, a first cover plate joined to and slidable on the middle plate and extending outwardly from the first side of the middle plate, and a second cover plate joined to the middle plate and extending outwardly from the first side of the middle plate. The first cover plate and the second cover plate are in overlying relationship with each other to define therebetween a space for receiving the plurality of reagent test slides in a stacked arrangement. The middle plate includes a T-shaped rail extending outwardly from the first side thereof and in a direction between the first cover plate and the second cover plate, and the first cover plate includes structure which defines a T-shaped slot, such as a pair of L-shaped legs which are spaced apart from one another and which define the T-shaped slot between them. The T-shaped slot of the first cover plate receives the T-shaped rail of the middle plate in order to slidably mount the first cover plate to the middle plate. Of course, it is envisioned to be within the scope of the present invention to reverse the positions of the cooperating T-shaped rail and the T-shaped slot so that the slot is defined by structure situated on the middle plate and the rail or T-shaped structure is situated on the first cover plate.

Alternatively, the retaining clip just previously described may be modified such that the middle plate may further include undulations which define at least one recess formed in the first side of the middle plate and extending toward the second side and in a direction between the first cover plate and the second cover plate, and at least one projecting guide structure extending outwardly toward the space for receiving the plurality of reagent test slides and in a direction between the first cover plate and the second cover plate. Also, the first cover plate may be modified from the just previously described embodiment to further include at least one tab which is slidably received by the at least one recess of the middle plate. The first cover plate also includes an exposed edge facing the middle plate and at least one recess formed in the exposed edge. The at least one projecting guide structure of the middle plate is slidably received by the at least one recess of the first cover plate. Accordingly, the at least one tab and the at least one recess of the first cover plate cooperate respectively with the at least one projecting guide structure and the at least one recess of the middle plate to minimize lateral movement of the first cover plate with respect to the middle plate. Again, of course, the positions of the cooperating recesses, tab and guide structure on the middle plate and first cover plate may be reversed.

In accordance with a further embodiment of the present invention, a retaining clip for retaining a plurality of reagent test slides in a stacked arrangement includes a first cover plate, and a second cover plate operatively coupled to the first cover plate. The first cover plate and the second cover plate are in overlying relationship with each other to define therebetween a space for receiving the plurality of reagent test slides in a stacked arrangement. The second cover plate has a concave shape and is resilient to exert pressure on the plurality of reagent test slides held in a stacked arrangement between the first cover plate and the second cover plate. The concavity of the second cover plate is directed toward the first cover plate so that the distance between the first cover plate and the second cover plate varies over the longitudinal lengths of the first cover plate and the second cover plate. Preferably, the minimum distance separating the first cover plate from the second cover plate is situated such that it is substantially at the center of the reagent test slides of the plurality of test slides measured along the longitudinal axis of the test slides.

These and other objects, features, and advantages of the present invention will be apparent from the following detailed description of illustrative embodiments thereof, which is to be read in connection with the accompanying drawings.

BRIEF DESCRIPTION OF THE DRAWINGS

FIG. 21 is a partially exploded, front isometric view of the retaining clip shown in FIG. 17, and being further shown holding a plurality of reagent test slides.

FIG. 22 is a partially exploded, rear isometric view of the retaining clip shown in FIG. 17 and further shown holding a plurality of reagent test slides.

FIG. 25A is a top plan view of a first portion of the retaining clip shown in FIG. 23.

FIG. 25B is a top plan view of a second portion of the retaining clip shown in FIG. 23.

DETAILED DESCRIPTION OF THE PREFERRED EMBODIMENTS

Figure 1:
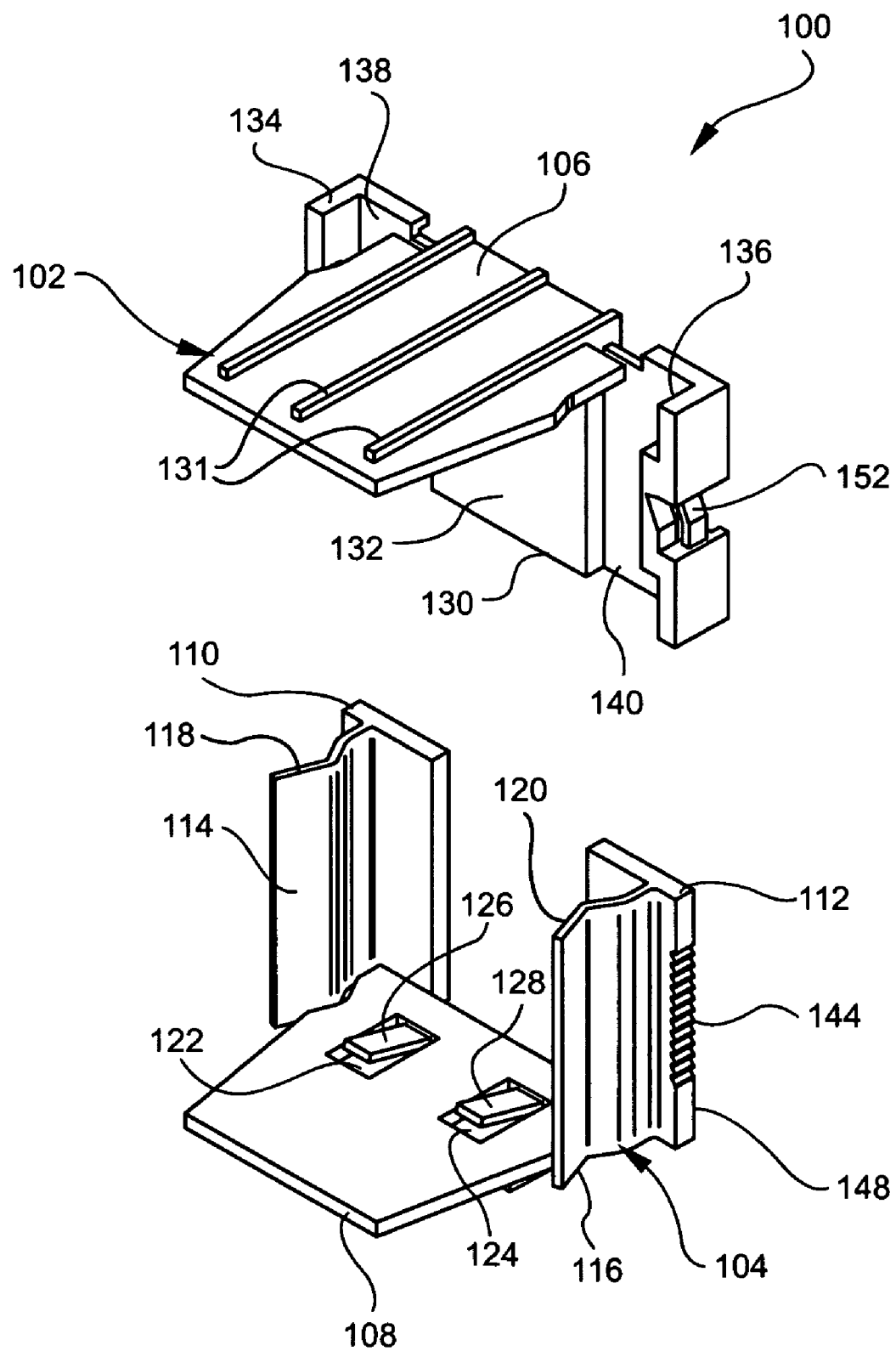
FIG. 1 is an exploded, isometric view of a first embodiment of a retaining clip formed in accordance with the present invention.
Figure 3:
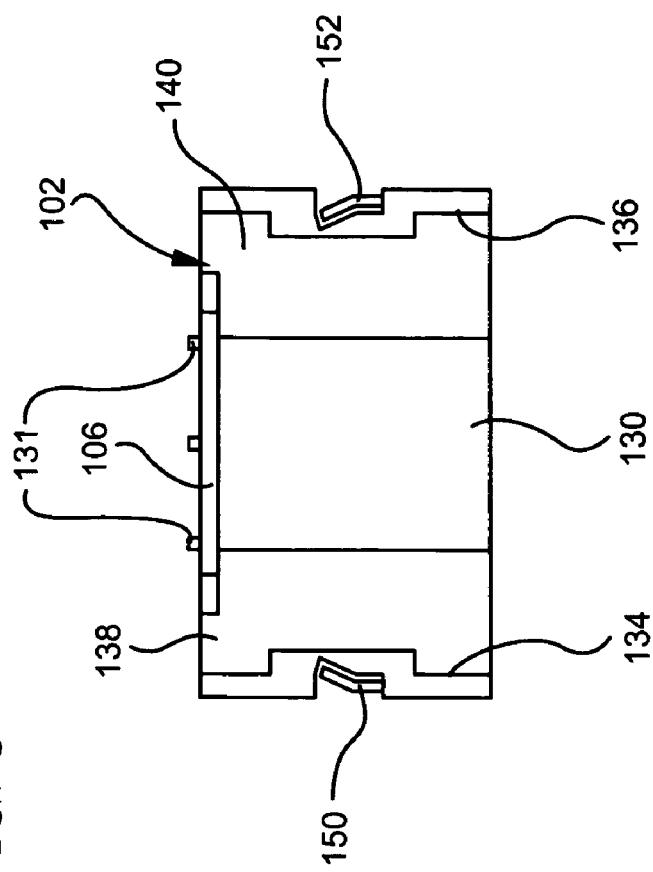
FIG. 3 is a front view of the first portion of the retaining clip shown in FIG. 2.
Figure 2:
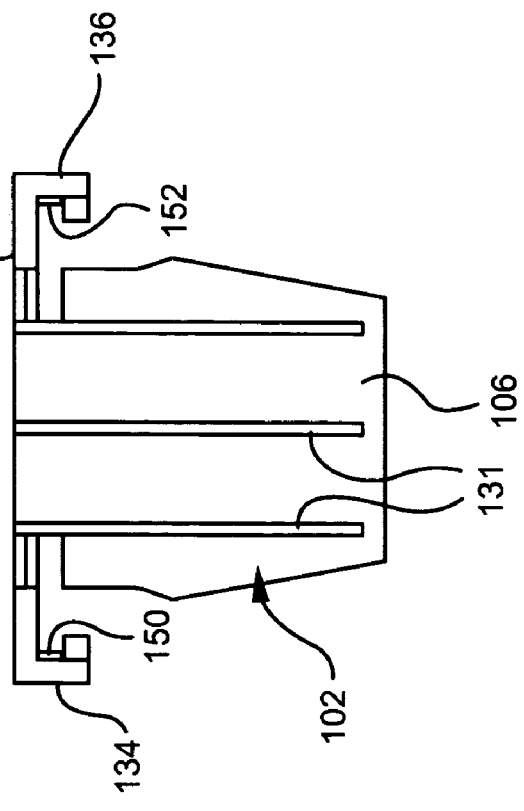
FIG. 2 is a top plan view of a first portion of the retaining clip shown in FIG. 1.
Figure 5:
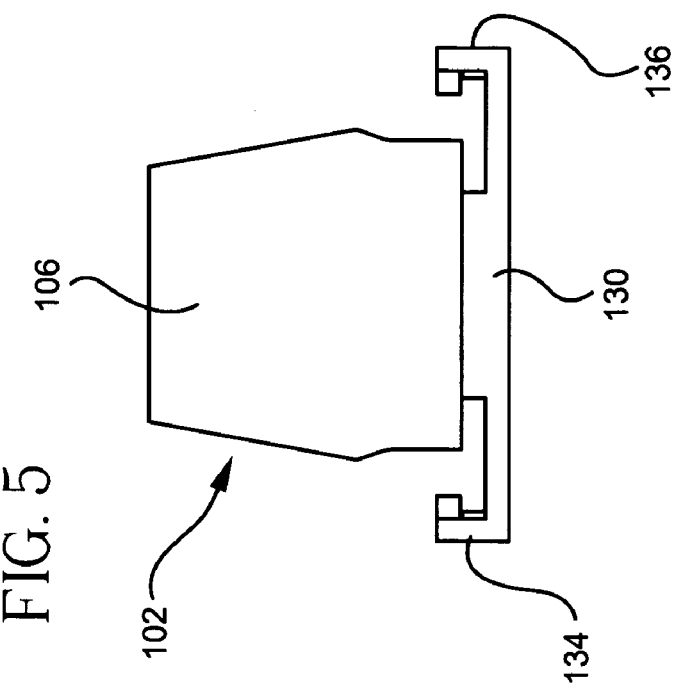
FIG. 5 is a bottom plan view of the first portion of the retaining clip shown in FIG. 2.
Figure 4:
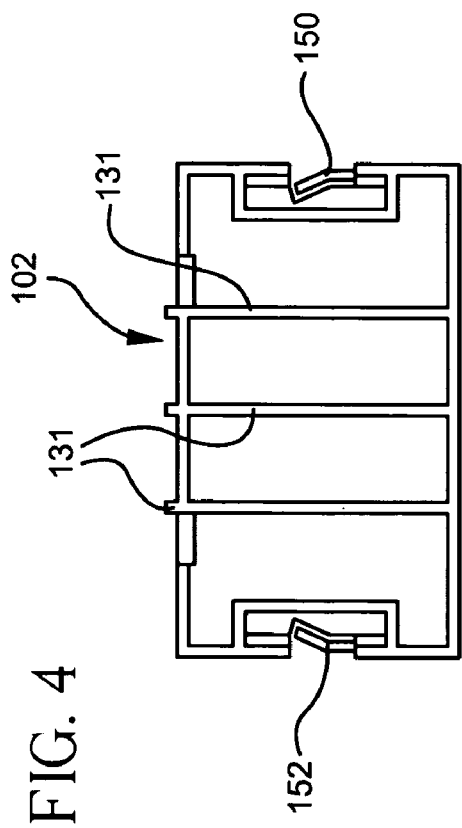
FIG. 4 is a rear view of the first portion of the retaining clip shown in FIG. 2.
Figure 7:
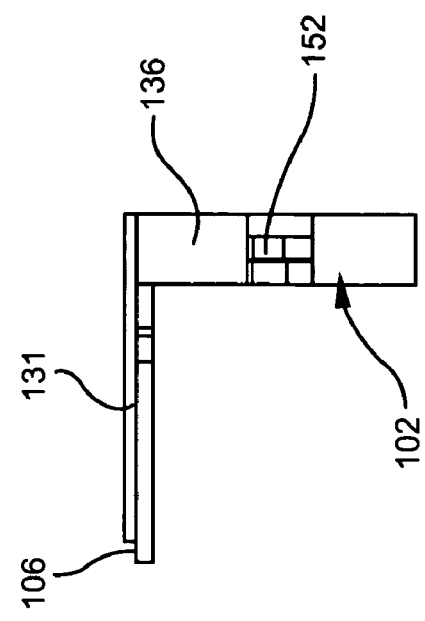
FIG. 7 is an opposite second side view of the first portion of the retaining clip shown in FIG. 2.
Figure 6:
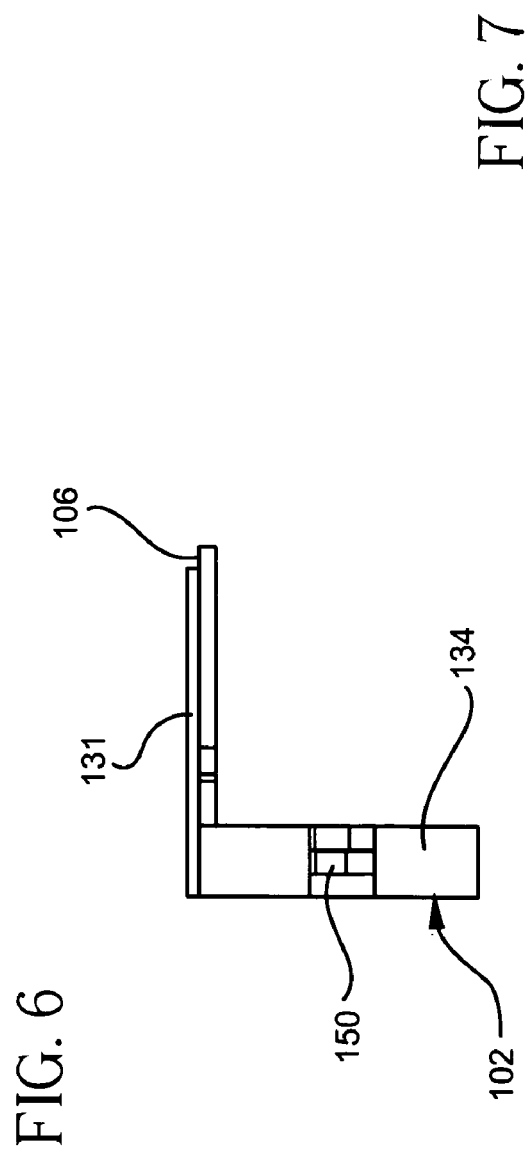
FIG. 6 is a first side view of the first portion of the retaining clip shown in FIG. 2.
Figure 8:
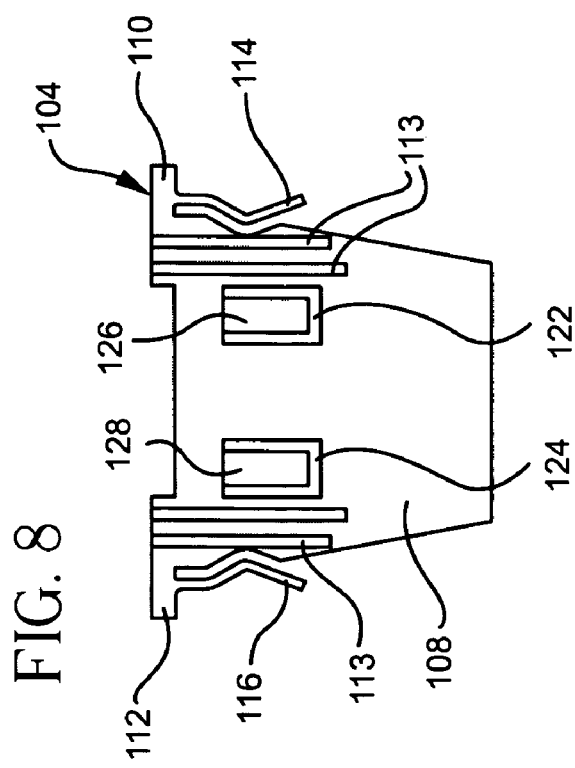
FIG. 8 is a top plan view of a second portion of the retaining clip shown in FIG. 1.
Figure 9:
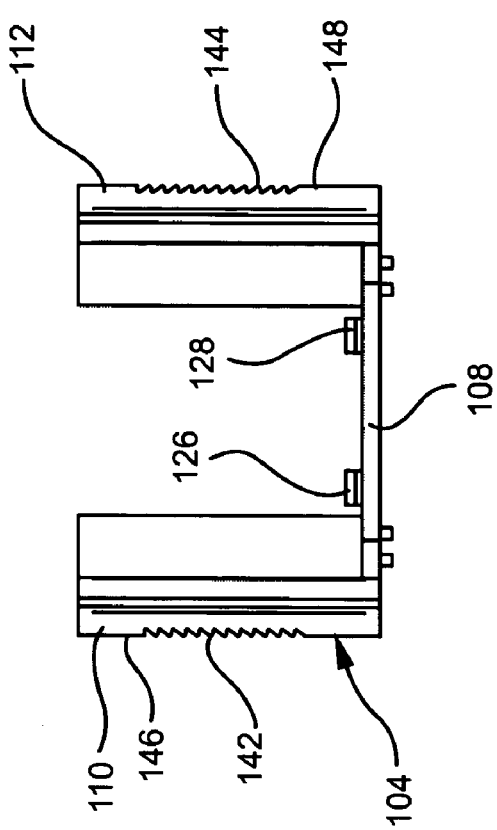
FIG. 9 is a front view of the second portion of the retaining clip shown in FIG. 8.
Figure 11:
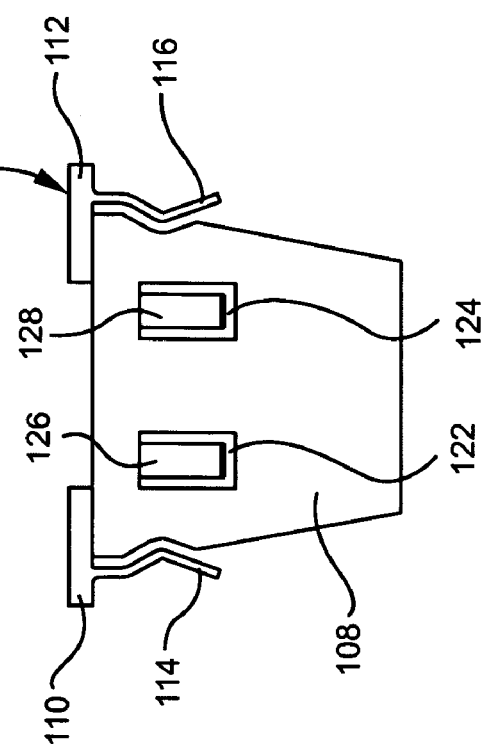
FIG. 11 is a bottom view of the second portion of the retaining clip shown in FIG. 8.
Figure 10:
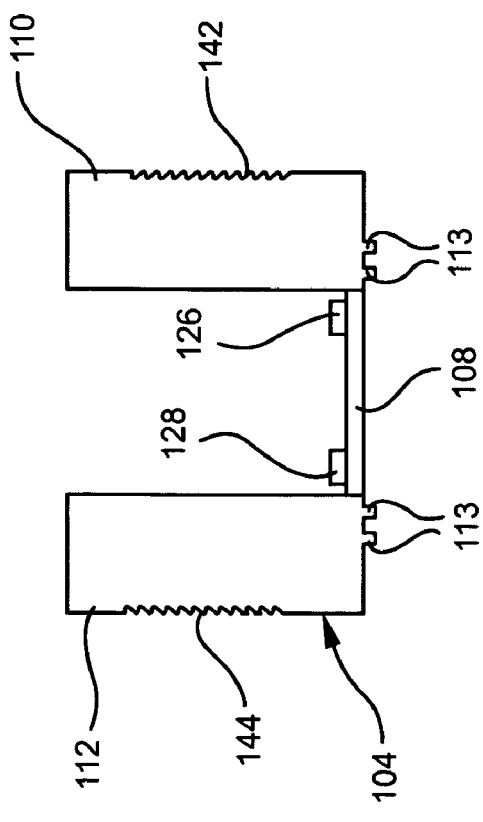
FIG. 10 is a rear view of the second portion of the retaining clip shown in FIG. 8.
Figure 13:
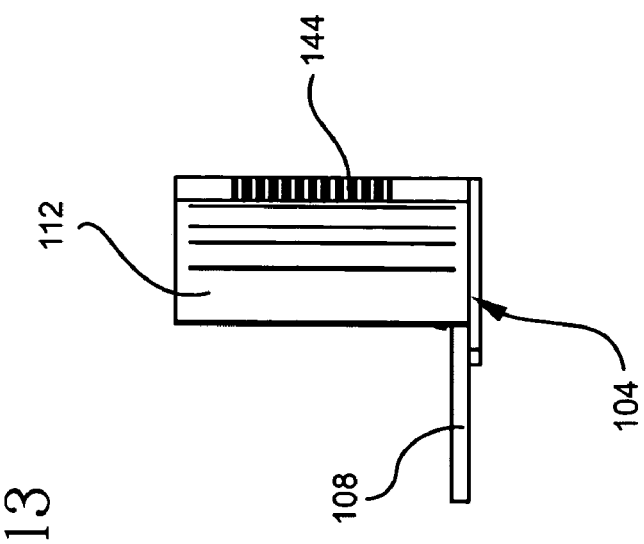
FIG. 13 is an opposite second side view of the second portion of the retaining clip shown in FIG. 8.
Figure 12:
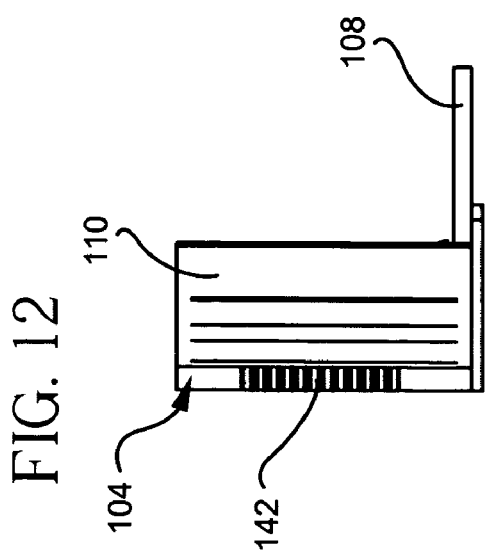
FIG. 12 is a first side view of the second portion of the retaining clip shown in FIG. 8.

A first embodiment of a retaining clip 100 formed in accordance with the present invention is illustrated by FIGS. 1-16 of the drawings. The retaining clip 100 of this particular embodiment includes a top cover assembly 102 and a bottom cover assembly 104. The top cover assembly 102 includes a top cover plate (also referred to herein as "first cover plate") 106, and the bottom cover assembly 104 includes a bottom cover plate (also referred to herein as "second cover plate") 108. The top cover plate 106 and the bottom cover plate 108 define between them a space for receiving a plurality of reagent test slides.

The bottom cover assembly 104 includes the bottom cover plate 108, as mentioned previously, and a first rail 110 and a second rail 112 extending parallelly in the same direction from, and affixed to, the bottom cover plate 108. Each of the first and second rails 110 and 112 are plate-like in formation, and includes free standing, resilient members 114 and 116 biased inwardly toward one another into the space for receiving the reagent test slides 70 (see FIG. 14). As will be seen, each free standing resilient member 114 and 116 acts as a leaf spring and exerts pressure on the lateral edges 72 of the test slides 70 to hold them in place between the top cover assembly 102 and the bottom cover assembly 104. Preferably, each free standing resilient member 114 and 116 includes a free end 118 and 120 which may be bent outwardly (away from the space provided for receiving the reagent test slides) to facilitate the insertion of a stack of reagent test slides 70 between the top cover plate 106 and the bottom cover plate 108 and the free standing resilient members 114 and 116 of the first and second rails 110 and 112. The outer surface of the bottom cover plate 108 may include one or more ribs 113 projecting outwardly therefrom for strengthening the bottom cover plate.

Figure 14:
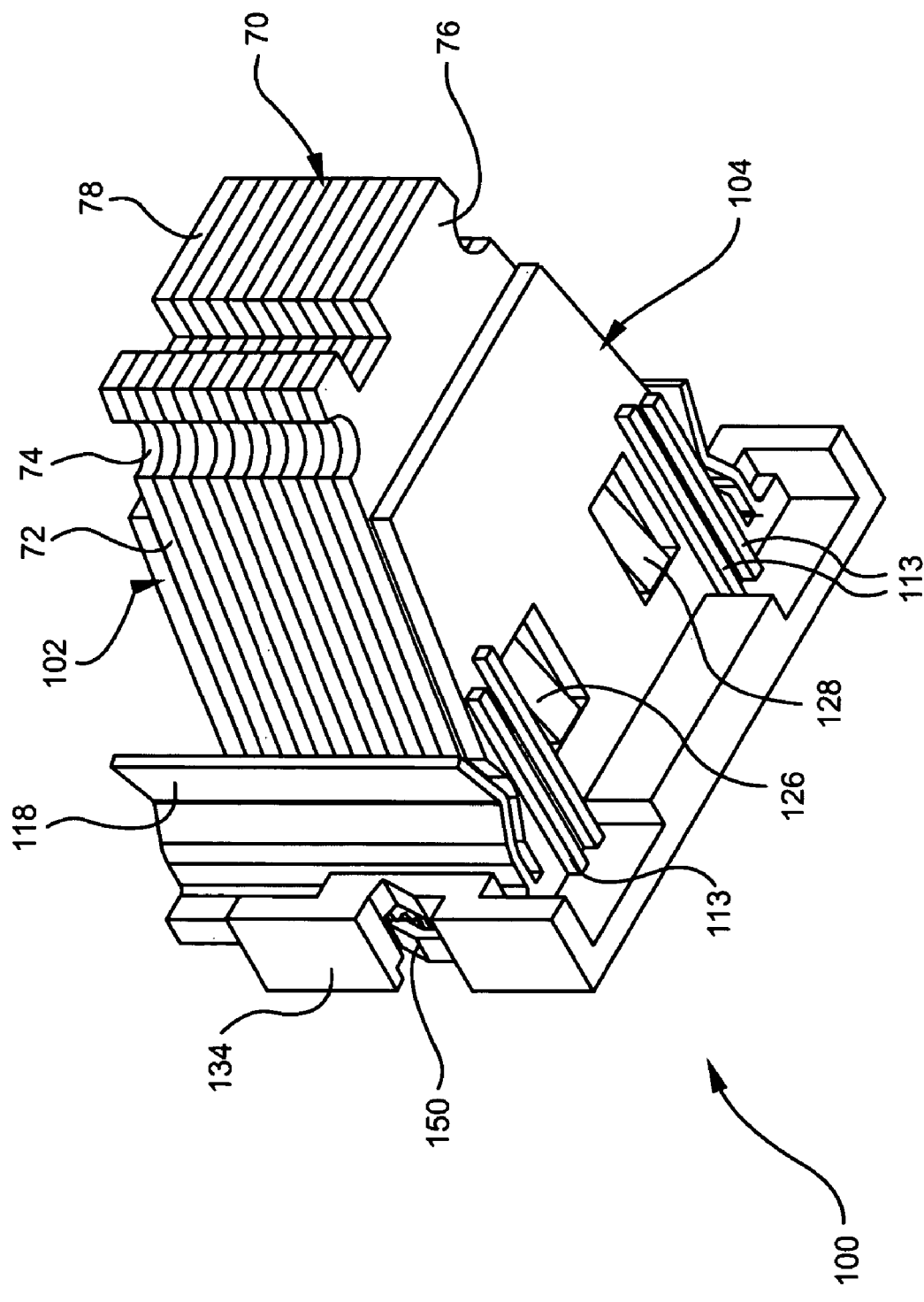
FIG. 14 is a front isometric view of the assembled retaining clip shown in FIG. 1 and shown holding a plurality of reagent test slides.
Figure 15:
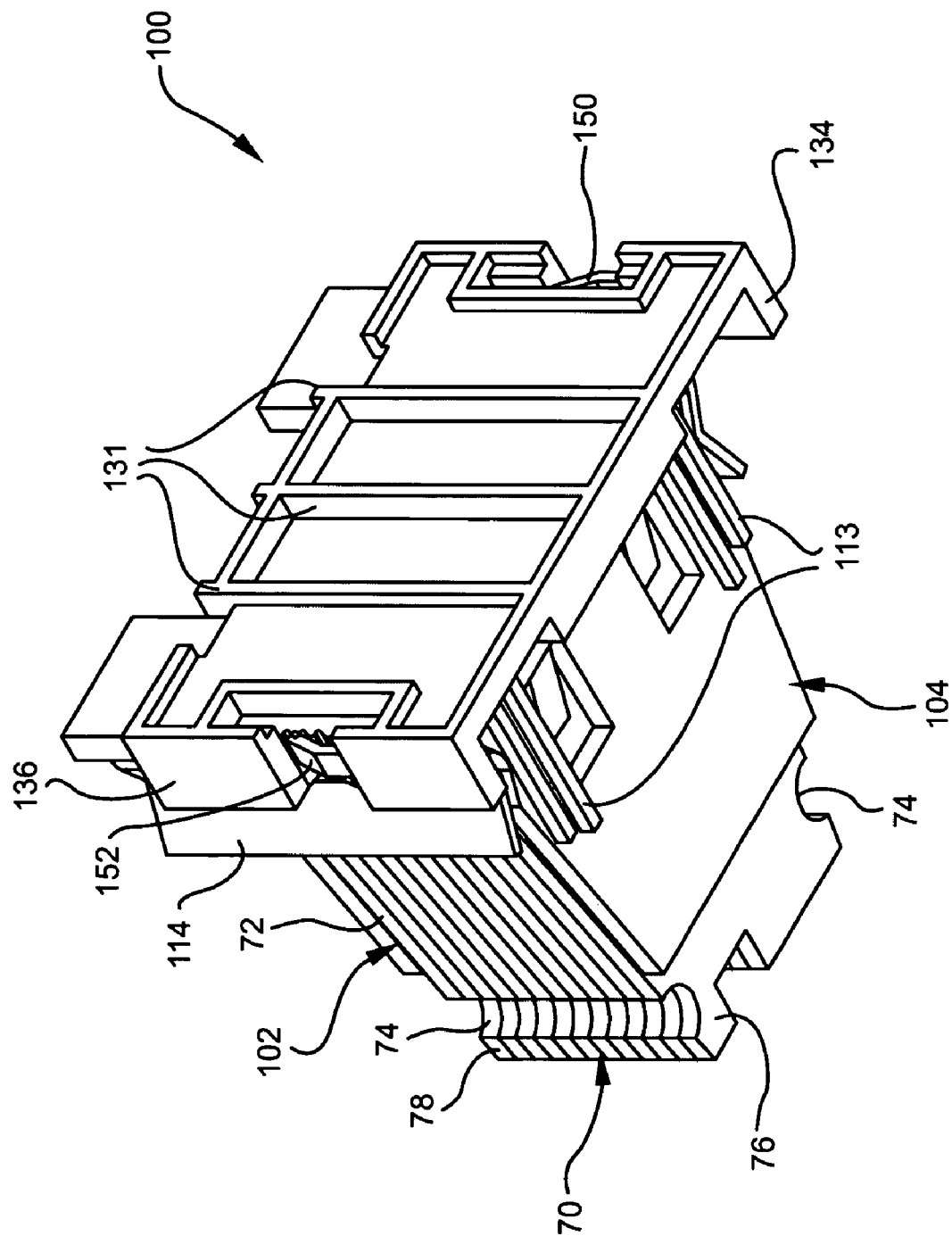
FIG. 15 is a rear isometric view of the assembled retaining clip shown in FIG. 1 and shown holding a plurality of reagent test slides.
Figure 16:
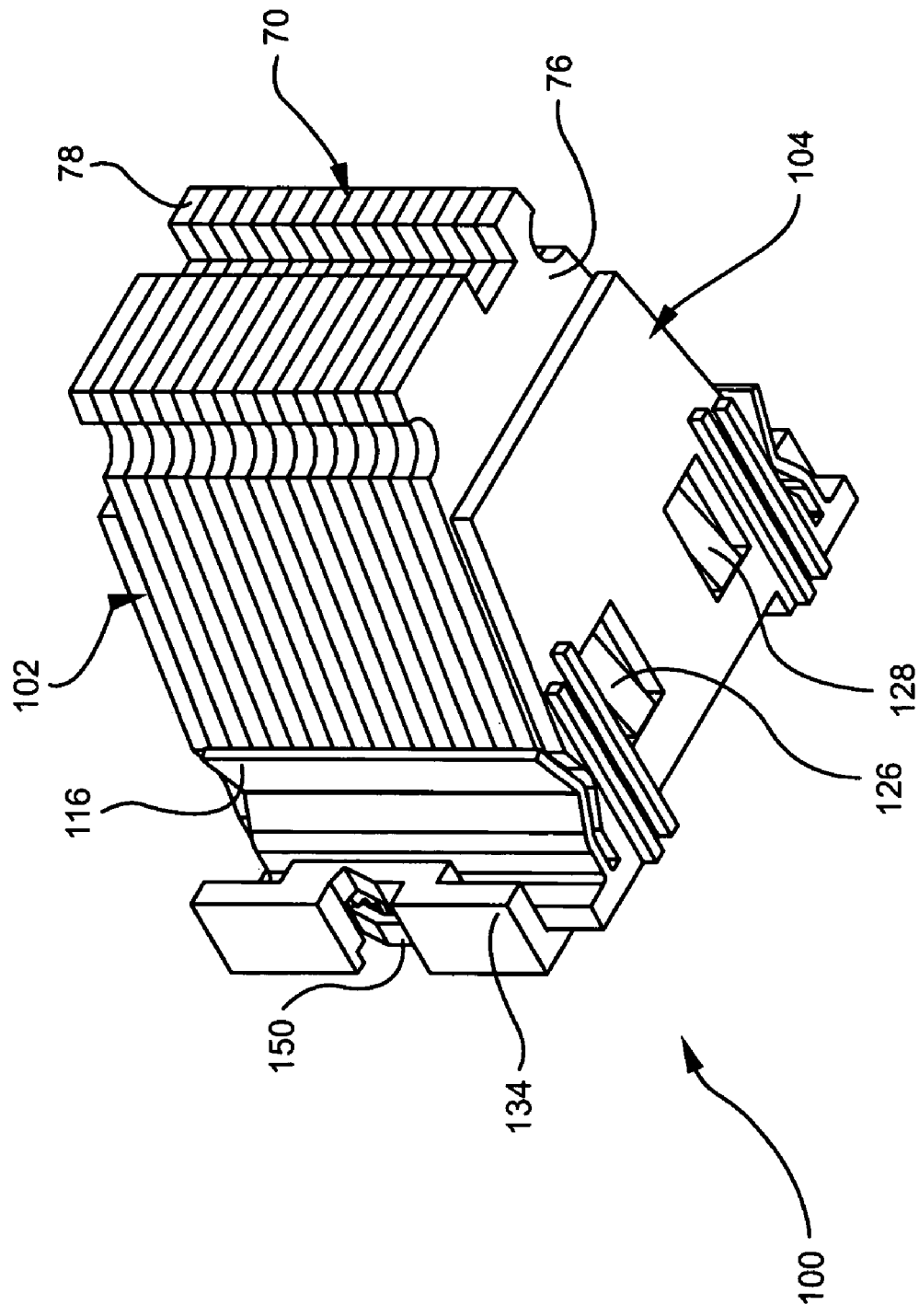
FIG. 16 is a front isometric view of the assembled retaining clip shown in FIG. 1 and shown having a plurality of reagent test slides, the number of reagent test slides being greater than that shown in FIG. 14.

The bottom cover plate 108 is preferably at least partially shaped to conform to the outer dimensions of the reagent test slides 70, as clearly shown in FIGS. 14-16 of the drawings. Furthermore, the bottom cover plate 108 preferably includes at least two cutouts 122 and 124, situated side-by-side but spaced apart a predetermined distance. Within the cutouts 122 and 124 are situated spaced apart resilient tabs 126 and 128 which are biased inwardly, that is, toward the top cover plate 106 and into the space provided for receiving the stack of reagent test slides 70. The resilient tabs 126 and 128 are spaced apart from one another, within the cutouts 122 and 124, a distance which is greater than the span of the film portion 73 of the reagent test slides 70 so that the tabs 126 and 128 exert pressure on only the support surface 71 of the bottom most slide 76 in the stack of slides 70 (see FIG. 19) and not on the film portion 73 thereof, and such that the film portion 73 of the bottom slide 76 resides between the spaced apart resilient tabs 126 and 128.

As shown in FIGS. 1 through 7 of the drawings, the top cover assembly 102 includes the top cover plate 106, as mentioned previously, and a rail receiving platform 130 which extends preferably perpendicularly from the top cover plate 106 at the bottom thereof. Like the bottom cover plate 108, the top cover plate 106 is preferably also at least partially shaped trapezoidally to conform to at least the outer dimensions of the reagent test slides 70 held by the retaining clip 100, as is clearly shown in FIGS. 1 and 16. The outer surfaces of the top cover plate 106 and the rail receiving platform 130 may include one or more ribs 131 projecting outwardly therefrom for strengthening the top cover plate 106 and the rail receiving platform 130.

The rail receiving platform 130 includes an upper surface 132, and a pair of opposite lateral side walls 134 and 136 extending preferably upwardly and perpendicularly from the upper surface 132. The upper surface 132 further has formed therein two spaced apart recesses 138 and 140 which act as tracks which are dimensioned in width to slidably receive the corresponding first and second rails 110 and 112 of the bottom cover assembly 104.

One or both of the first rail 110 and the second rail 112 include ratchet teeth 142 and 144 formed in the outwardly disposed edges 146 and 148 thereof which, as will be described in greater detail, cooperate with pawls 150 and 152 formed in the top cover assembly 102.

One or both of the lateral side walls 134 and 136 of the top cover assembly 102 may include a resilient pawl 150 and 152 which is biased inwardly to extend partially into one or both of the tracks 138 and 140. Each pawl 150 and 152 is positioned on its corresponding side wall 134 and 136 in height such that it engages the ratchet teeth 142 and 144 of the first rail 110 and second rail 112 when such rails 110 and 112 are received by the recesses or tracks 138 and 140 of the top cover assembly 102.

The slide retaining clip 100 of the first embodiment can receive a plurality of reagent test slides 70 in at least one of two ways. In the first way, the top cover assembly 102 may be spaced apart from the bottom cover assembly 104, and the plurality of the reagent test slides 70, arranged in a stack, may be slid onto the bottom cover assembly 104 between the first rail 110 and the second rail 112. Then, the bottom cover assembly 104 is mated to the top cover assembly 102, with the first rail 110 and second rail 112 being received by their corresponding recesses or tracks 138 and 140 formed in the rail receiving platform 130. The pawls 150 and 152 formed in the side walls 134 and 136 of the top cover assembly 102 engage the ratchet teeth 142 and 144 formed in the first and second rails 110 and 112 to hold the top cover assembly 102 and the bottom cover assembly 104 together and to prevent their separation, with the plurality of stacked reagent test slides 70 held between the top cover plate 106 and the bottom cover plate 108 and the free standing resilient members 114 and 116. The top cover plate 106 and bottom cover plate 108 are squeezed together so that the plurality of reagent test slides 70 are held sufficiently tightly therebetween. The resilient tabs 126 and 128 formed in the bottom cover plate 108 exert further pressure on the stack of slides 70. Stated another way, the cooperating pawls 150 and 152 and ratchet teeth 142 and 144 provide an incremental pressure on the stack of slides 70 when the bottom cover assembly 104 is received by the top cover assembly 102. The resilient tabs 126 and 128 formed in the bottom cover assembly 104 provide a fine, continuous pressure on the stack of slides 70 to account for the coarse adjustment in pressure provided incrementally by the interaction of the pawls 150 and 152 and ratchet teeth 142 and 144.

The plurality of reagent test slides 70 may also be received by inserting the slides 70, as a stack, or individually, between the free standing resilient members 114 and 116 and the top cover plate 106 and the bottom cover plate 108 of the pre-assembled top cover assembly 102 and the bottom cover assembly 104 of the retaining clip 100. Once the plurality of reagent test slides 70 are received in the space provided, the bottom cover assembly 104 is adjusted with respect to the top cover assembly 102, the pawls 150 and 152 and ratchet teeth 142 and 144 interacting to allow movement of the bottom cover assembly 104 with respect to the top cover assembly 102 in one direction only, which is toward one another, so as to exert pressure on the stack of reagent test slides 70 received therebetween and to tightly, but removably, hold the stack 70 in place on the retaining clip 100.

As shown in FIGS. 1-16, the retaining clip 100 formed in accordance with the first embodiment of the present invention can receive any number of reagent test slides, in a stack, and hold the test slides 70 in place. It should be further noted that the top cover plate 106 and bottom cover plate 108 of this embodiment of the retaining clip 100 covers the film portion 73 of the bottom and top reagent test slides 76, 78 in the stack to minimize the evaporation of any analyte provided thereon. It should be further noted that the top cover plate 106 and the bottom cover plate 108 only extend as far as necessary to cover the film portion 73 and to firmly hold the reagent test slides 70 between them. The recesses 74 formed in the lateral edges 72 of the reagent test slides 70 are exposed to allow the entire stack of slides 70 to be inserted onto the injector mechanism of the chemical analyzer, as will be described in greater detail, and the removal of the reagent test slides, as a stack, from the retaining clip 100 of the present invention.

Figure 16A:
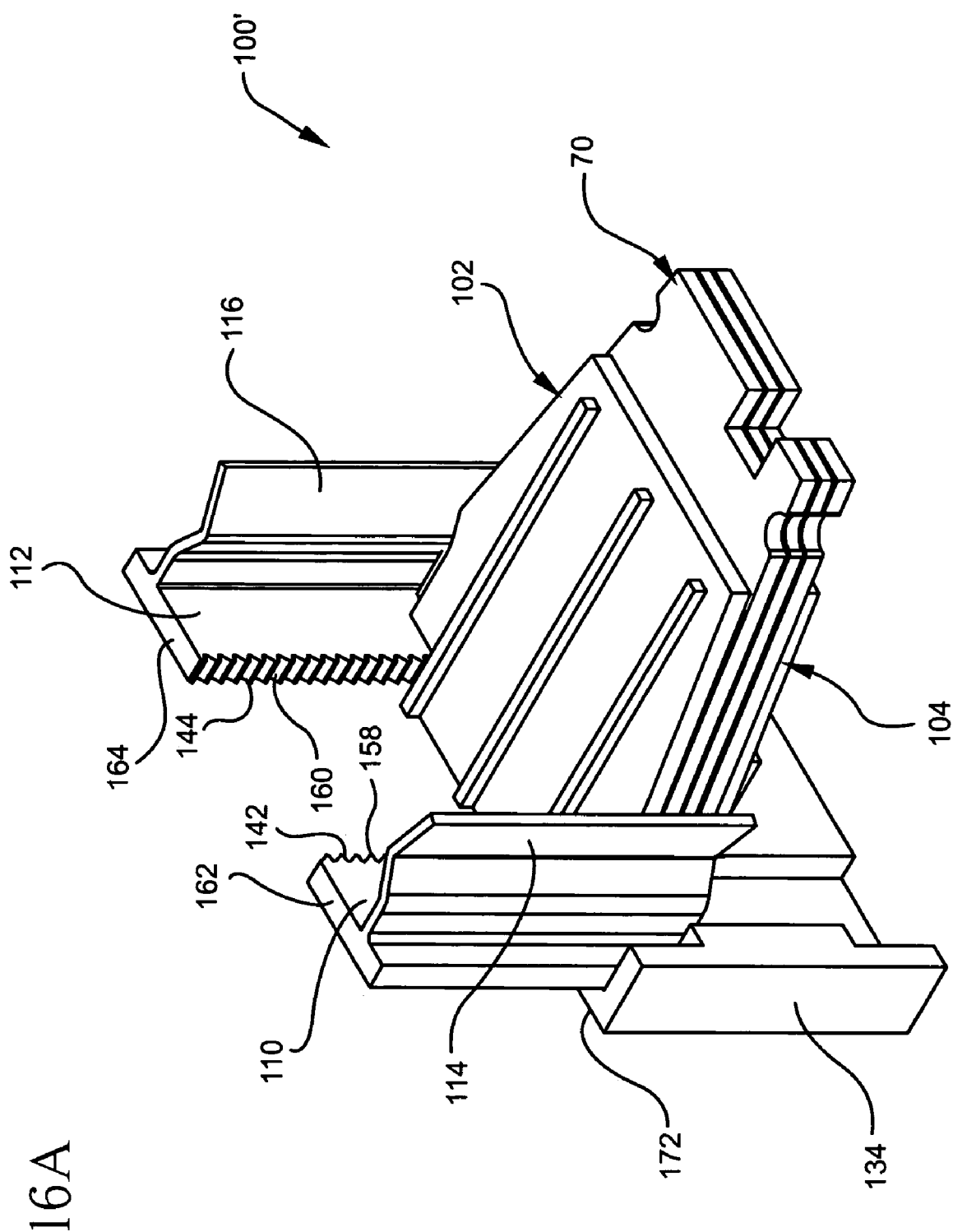
FIG. 16A is a front isometric view of a variation of the first embodiment of the retaining clip of the present invention shown in FIGS. 1 through 16.
Figure 16B:
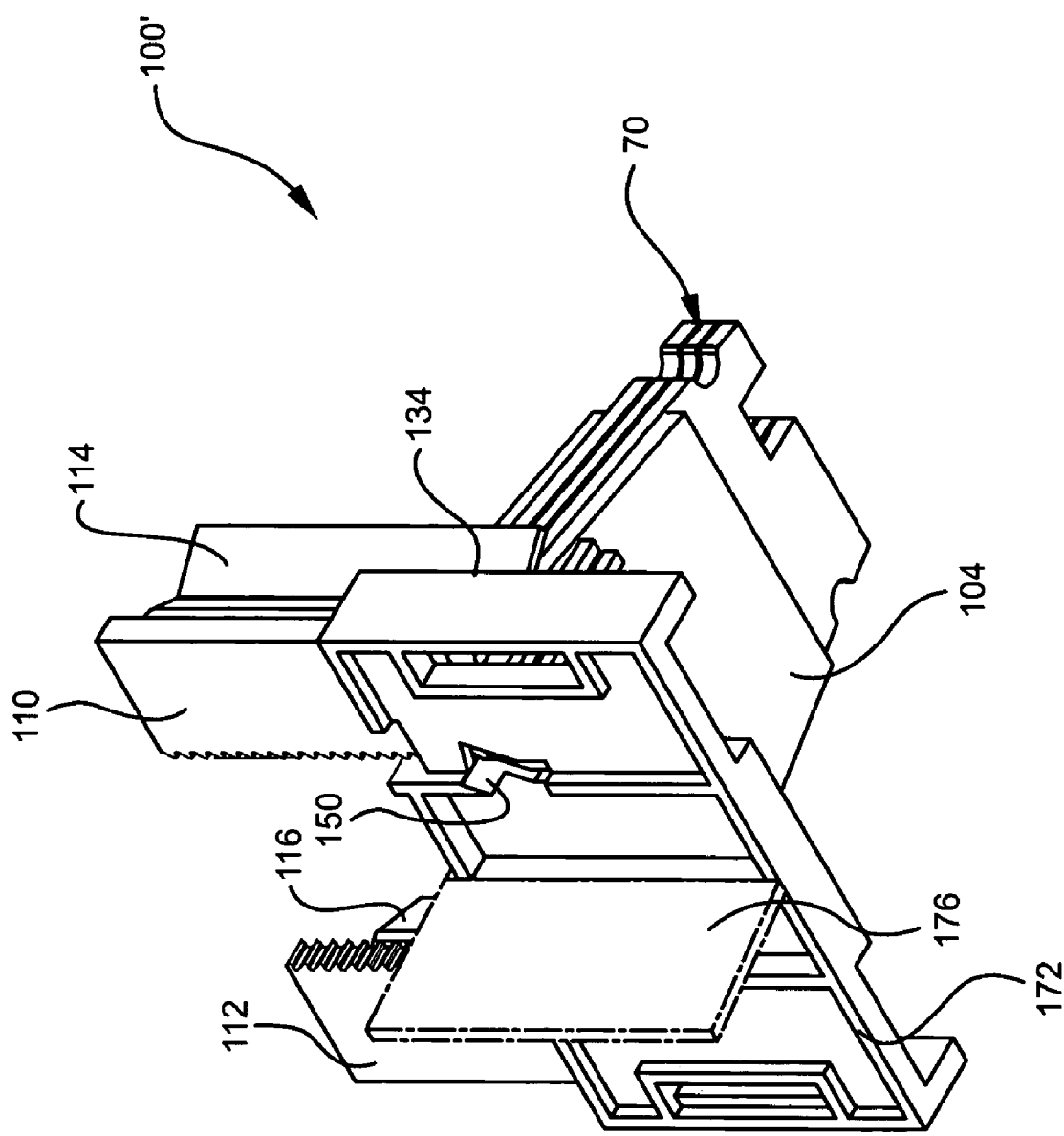
FIG. 16B is a rear isometric view of the retaining clip shown in FIG. 16A.
Figure 17:
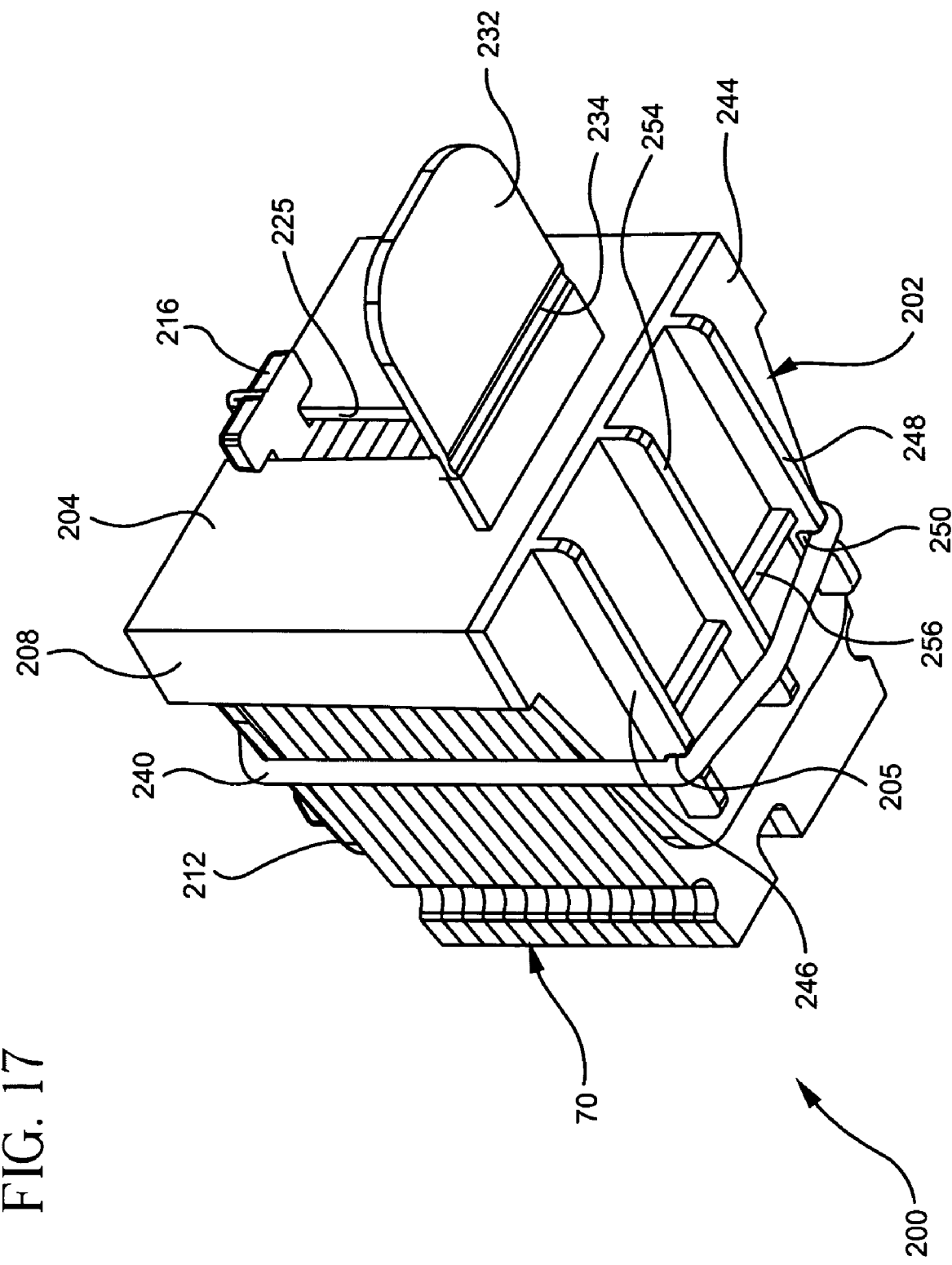
FIG. 17 is a bottom rear isometric view of a second embodiment of a retaining clip formed in accordance with the present invention, and shown holding a plurality of reagent test slides.
Figure 18:
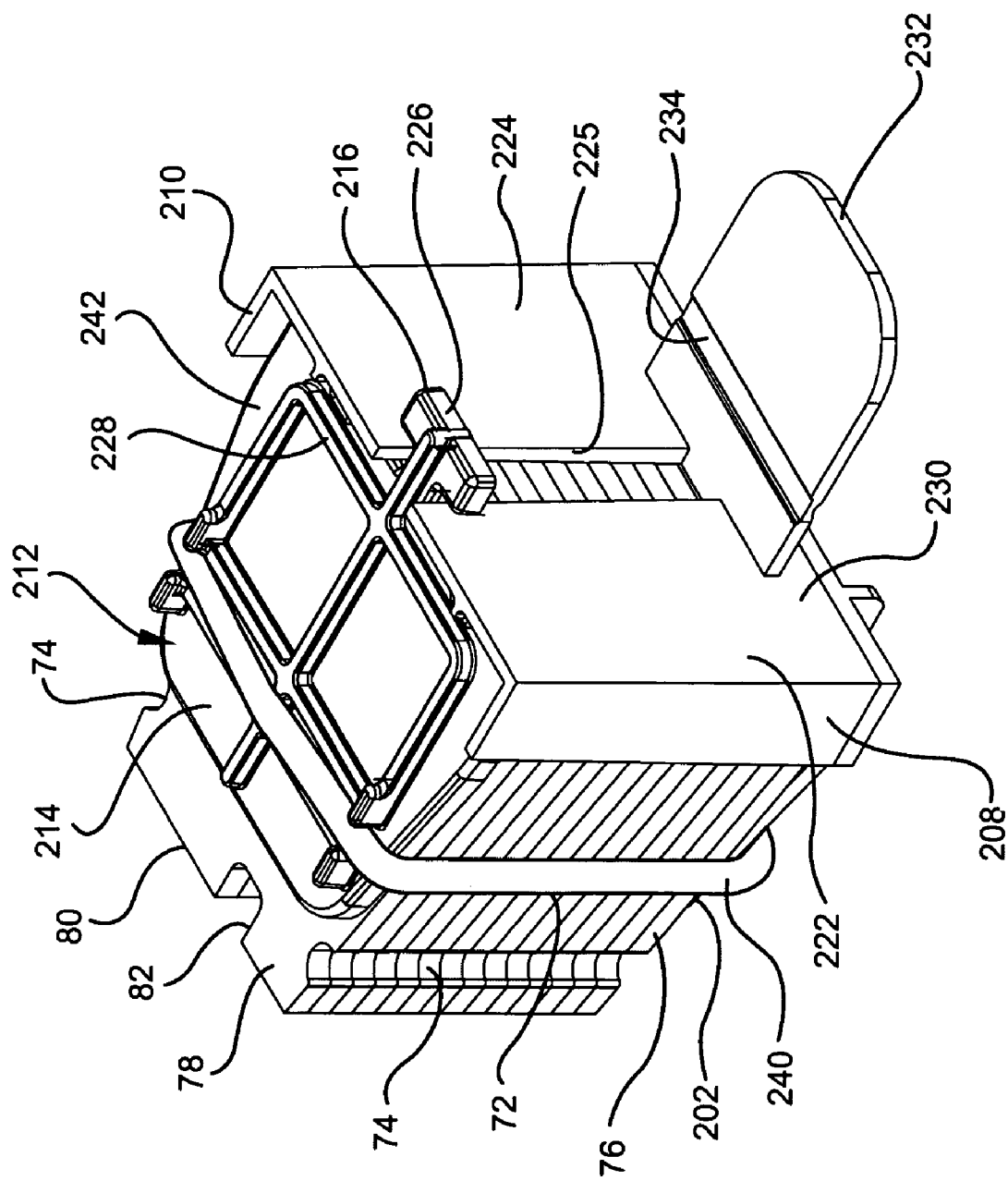
FIG. 18 is a top rear isometric view of the retaining clip shown in FIG. 17.

As shown in FIGS. 16A and 16B, the first embodiment of the retaining clip 100 may alternatively be formed as clip 100' such that the ratchet teeth 142 and 144 are positioned on the inwardly disposed edges 158 and 160 of the rails 142 and 144. The pawls 150 and 152 may also be arranged to engage the ratchet teeth 142 and 144 on the inwardly disposed edges 158 and 160. Also, in this variation of the retaining clip 100' shown in FIGS. 16A and 16B, a handle 176 for grasping by the user protrudes from the rear surface of the bottom cover assembly 104.

FIGS. 17-22 of the drawings illustrate a second embodiment of a retaining clip 200 formed in accordance with the present invention. In the second embodiment, the retaining clip 200 includes a back wall or middle plate 204, a bottom cover plate (also referred to herein as "second cover plate") 202 which is fixedly joined to the back wall 204 and extends from a front surface 206 thereof preferably perpendicularly therefrom, and a pair of lateral side walls 208 and 210 situated opposite one another and extending preferably perpendicularly from the same surface 206 of the back wall and in the same direction from which the bottom cover plate 202 extends. The inner facing surfaces of the opposite lateral side walls 208 and 210 are preferably spaced apart from one another a distance W1 which is equal to or slightly greater than the width W2 of the reagent test slides 70 so as to hold a plurality of test slides 70 between them.

The retaining clip 200 of the second embodiment further includes a top cover plate (also referred to herein as "first cover plate") 212 which is slidably mounted on the back wall 204. More specifically, the top cover plate 212 includes a generally planar main body portion 214, and a T-shaped extension 216 which extends from its rear edge 218 of the main body portion 214. The T-shaped extension 216 includes a narrow portion 227 extending outwardly from the main body portion 214, and a widened portion 226 joined to the end of the narrow portion 227. This T-shaped extension 216 is slidingly received by a slot 225 formed preferably centrally through the thickness of the back wall 204 and extends at least partially longitudinally along the back wall 204 between the bottom cover plate 202 and the top edge 203 of the back wall 204. The slot 225 in the back wall 204 is particularly dimensioned to have a width W3 which is equal to or slightly greater than the width W4 of the narrower portion 227 of the T-shaped extension 216 of the top cover plate 212, but less than the width W5 of the wider portion 226 of the T-shaped extension 216 so as to hold the top cover plate 212 captive to the back wall 204 but allow it to slide reciprocatingly within the slot 225.

Preferably, slot 225 is open at the top edge of the back wall 204 to receive the T-shaped extension 216 of the top cover plate 212 through the open end of the slot, as shown in FIGS. 17-22. However, it is envisioned to be within the scope of the present invention to have the slot 225 closed at both ends; the retaining clip having such slot structure would be assembled by turning the top cover plate 212 through an angle of 90 degrees from its normal position, of course with no slides being held by the retaining clip, such that the plane in which the top cover plate 212 generally resides is parallel to the longitudinal axis of the back wall slot 225. The T-shaped extension 216 of the top cover plate 212 is inserted through the slot 225, and the top cover plate 212 is then rotated in the reverse direction by 90 degrees to its normal position such that the widened portion 226 of the T-shaped extension 216 extends beyond the lateral confines of the slot 225 and the rear surface 230 of the back wall 204.

A plurality of reagent test slides 70 are received between the lateral side walls 208 and 210 of the retaining clip 200 and the top cover plate 212 and the bottom cover plate 202, and are held in place thereby as a stack. Preferably, the shape of the top cover plate 212 and the bottom cover plate 202 is such as to at least partially conform to, or partially overlap, the shape and dimensions of the reagent test slides 70. Preferably, the top cover plate 212 and the bottom cover plate 202 extend beyond, and thus cover, the film portions 73 of the top slide 78 and the bottom slide 76 in the stack of reagent test slides 70 to help minimize evaporation of any analyte deposited thereon. However, preferably the top cover plate 212 and the bottom cover plate 202 extend outwardly from the back wall 204 only a distance which allows the recesses 74 formed in the lateral edges 72 of the reagent test slides 70 and the orientation notch 82 formed in the front edge 80 of the slides to be exposed so that the entire stack of reagent test slides 70, still held by the retaining clip 200, may be received by a slide injector mechanism of a chemical analyzer, as will be described in greater detail.

Preferably, the retaining clip 200 of this second embodiment of the present invention includes a foldable handle 232 which extends outwardly from the rear surface 230 of the back wall 204. The foldable handle 232 is preferably joined to the rear surface 230 of the back wall 204 by using a living hinge 234 to allow it to fold in either direction, or more preferably, upwardly toward the top cover plate 212 of the retaining clip 200. More specifically, in a first position, the handle 232 extends preferably 90 degrees outwardly from the rear surface 230 of the back wall 204 of the retaining clip 200, and is situated on the back wall 204 closer to the bottom cover plate 202 than to the top cover plate 212.

The handle 232 may be pivoted at the living hinge 234 to a second position such that it is essentially folded against or in close proximity to the rear surface 230 of the back wall 204 and such that it does not protrude outwardly from the back wall 204 for compactness during shipping or packaging and when the retaining clip 200 is not being handled. When it is desired to load the plurality of test slides 70 onto the slide injector mechanism of the chemical analyzer, the user may move the handle 232 from its unextended position to its extended position for grasping.

To ensure that the plurality of reagent test slides 70 remain held in place by the retaining clip 200, an elastic or flexible band 240, such as an o-ring, may be used, encircling the stack of reagent test slides 70 and the top cover plate 212 and the bottom cover plate 202. In order to hold the elastic band 240 in place, the outer surface 244 of the bottom cover plate 202 may include a pair of spaced apart first ribs 246 and 248 extending outwardly therefrom and in each of which is formed a recess 250 to receive and properly seat the elastic band 240. The outer surface 242 of the top cover plate 212 preferably includes a pair of parallel ribs 247 and 249 extending outwardly therefrom and transversely across the top cover plate 212. The ribs 247 and 249 have raised projections 251 at their opposite ends. The ribs 247 and 249 and projections 251 define between them a valley for receiving and securing in place the elastic band 240. The top cover plate 212 and the bottom cover plate 202 may further include other transverse and longitudinal projecting ribs, such as ribs 252, 254, 256, 281, 283, 285 and 287, to help strengthen the top cover plate 212 and the bottom cover plate 202.

The top cover plate 212 may further include notches 290 formed in its rear edge 218, which notches are aligned with and receive corresponding ribs 292 formed in and projecting outwardly from the front surface 206 of the back wall 204, which ribs 292 extend from the bottom cover plate 202 to the top edge 203 of the back wall 204.

FIGS. 23 through 28 illustrate a third embodiment of a retaining clip 300 formed in accordance with the present invention. The third embodiment of the slide retaining clip 300 includes a back wall (also referred to herein as "middle plate") 304, a bottom cover plate (also referred to herein as "second cover plate") 302 attached to the back wall 304 and preferably extending perpendicularly therefrom, and opposite lateral side walls 306 and 308 attached to the back wall 304 and extending preferably perpendicularly therefrom in the same direction as the bottom cover plate 302. A top cover plate (also referred to herein as "first cover plate") 310 is slidably mounted on the back wall 304 at its front surface 312 and is situated between the opposite lateral side walls 306 and 308.

Situated on the front surface 312 of the back wall 304 of the slide retaining clip 300 are a pair of spaced apart guide plates 314 and 316. The guide plates 314 and 316 preferably extend perpendicularly outwardly from the front surface 312 of the back wall 304, but not as far as the opposite lateral side walls 306 and 308 extend from the front surface 312 of the back wall 304. The guide plates 314 and 316 extend preferably from the inner surface 318 of the bottom cover plate 302 to the top edge 320 of the back wall 304. The rear edge 322 of the top cover plate 310 has notches 324, 326 formed therein which slidably receive guide plates 314, 316, respectively.

A T-shaped rail 328 is positioned preferably centrally on the front surface 312 of the back wall 304 and preferably extends from the inner surface 318 of the bottom cover plate 302 to the top edge 320 of the back wall 304. The T-shaped rail 328 preferably extends perpendicularly outwardly from the front surface 312 of the back wall 304, and includes a narrow portion 330 and a widened portion 332 mounted on the narrow portion 330. The widened portion 332 of the T-shaped rail 328 and the front surface 312 of the back wall 304 together define a pair of slots 334, 336 therebetween.

The top cover plate 310 includes a main body portion 338 and a pair of spaced apart L-shaped extended portions 340, 342 extending from the rear side of the main body portion 338 and disposed in the same plane in which the main body portion 338 and generally the top cover plate 310 reside. The L-shaped extended portions 340, 342 are spaced apart from one another and are disposed in mirrored symmetry to one another, thereby defining therebetween a narrow slot 344 and a widened slot 346 communicating with the narrow slot 344. The spacing between the L-shaped extended portions 340, 342 which define the narrow slot 344 is dimensioned with a width that is slightly greater than the width of the narrow portion 330 of the T-shaped rail 328. The spacing between the L-shaped extended portions 340, 342 of the top cover plate 310 which define between them the widened slot 346 is dimensioned to be slightly greater than the width of the widened portion 332 of the T-shaped rail 328. Accordingly, the T-shaped rail 328 may be received between the pair of L-shaped extended portions 340, 342 of the top cover plate 310 within the narrow slot 344 and widened slot 346 which the L-shaped extended portions 340, 342 define. Thus, the cooperating structure of the back wall 304 and the top cover plate 310 allows the top cover plate 310 to be mounted to the back wall 304 but reciprocatingly movable thereon along the T-shaped rail 328 from preferably the inner surface 318 of the bottom cover plate 302 to the top edge 320 of the back wall 304. As mentioned previously, the top cover plate 310 resides between the opposite lateral side walls 306, 308 of the back wall 304, and the rear edge 322 of the top cover plate 310 further contacts the front surface 312 of the back wall 304, with the guide plates 314, 316 being slidably received by notches 324, 326, respectively, of the top cover plate 310. Thus, this particular structure allows the top cover plate 310 to move reciprocatingly slidably on the T-shaped rail 328 of the back wall 304, but prevents lateral movement of the top cover plate 310 with respect to the back wall 304 when the top cover plate 310 is mounted thereon.

Figure 27:
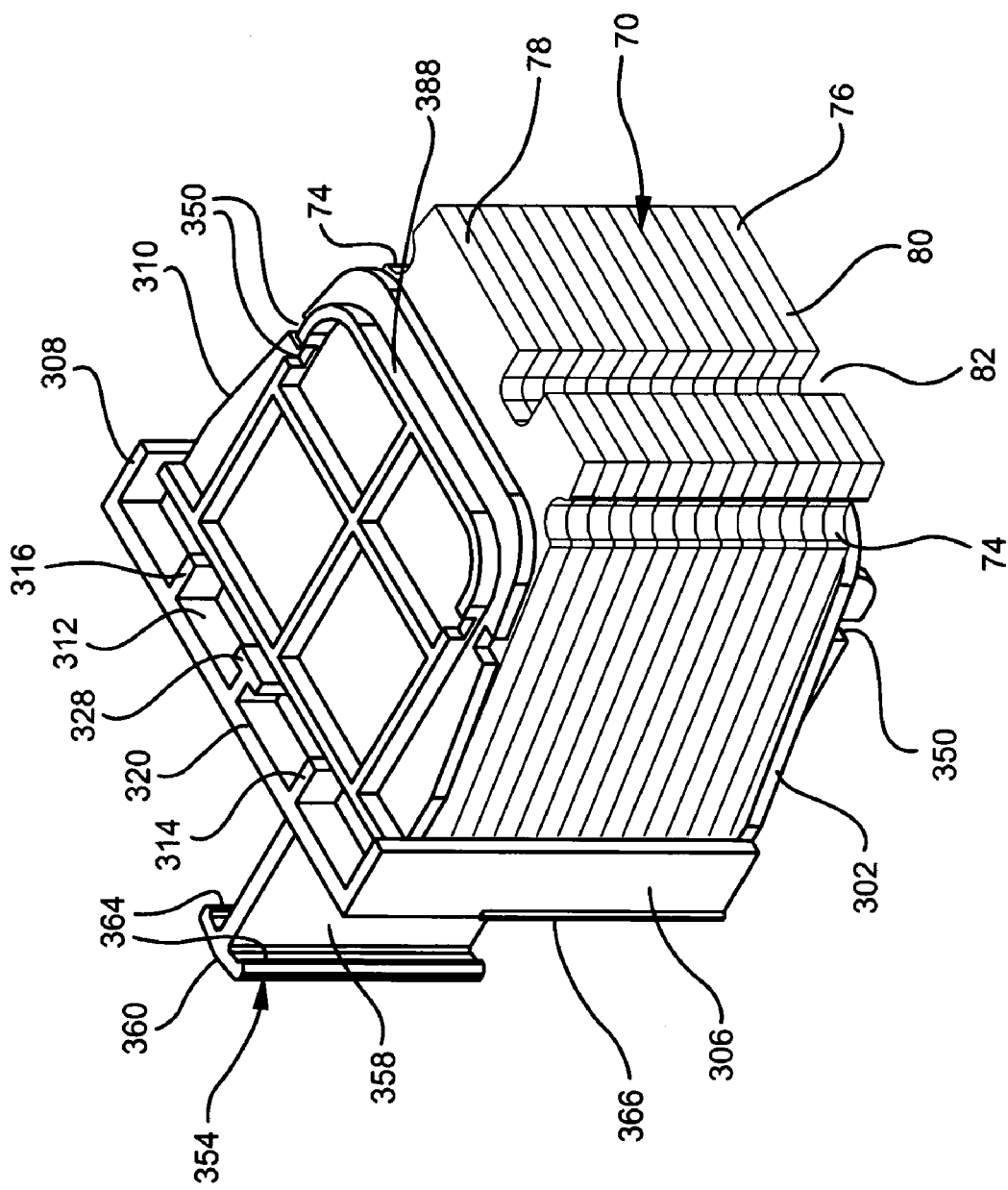
FIG. 27 is a front isometric view of the retaining clip shown in FIG. 23 and further shown holding a plurality of reagent test slides and having a part thereof in an extended position.
Figure 28:
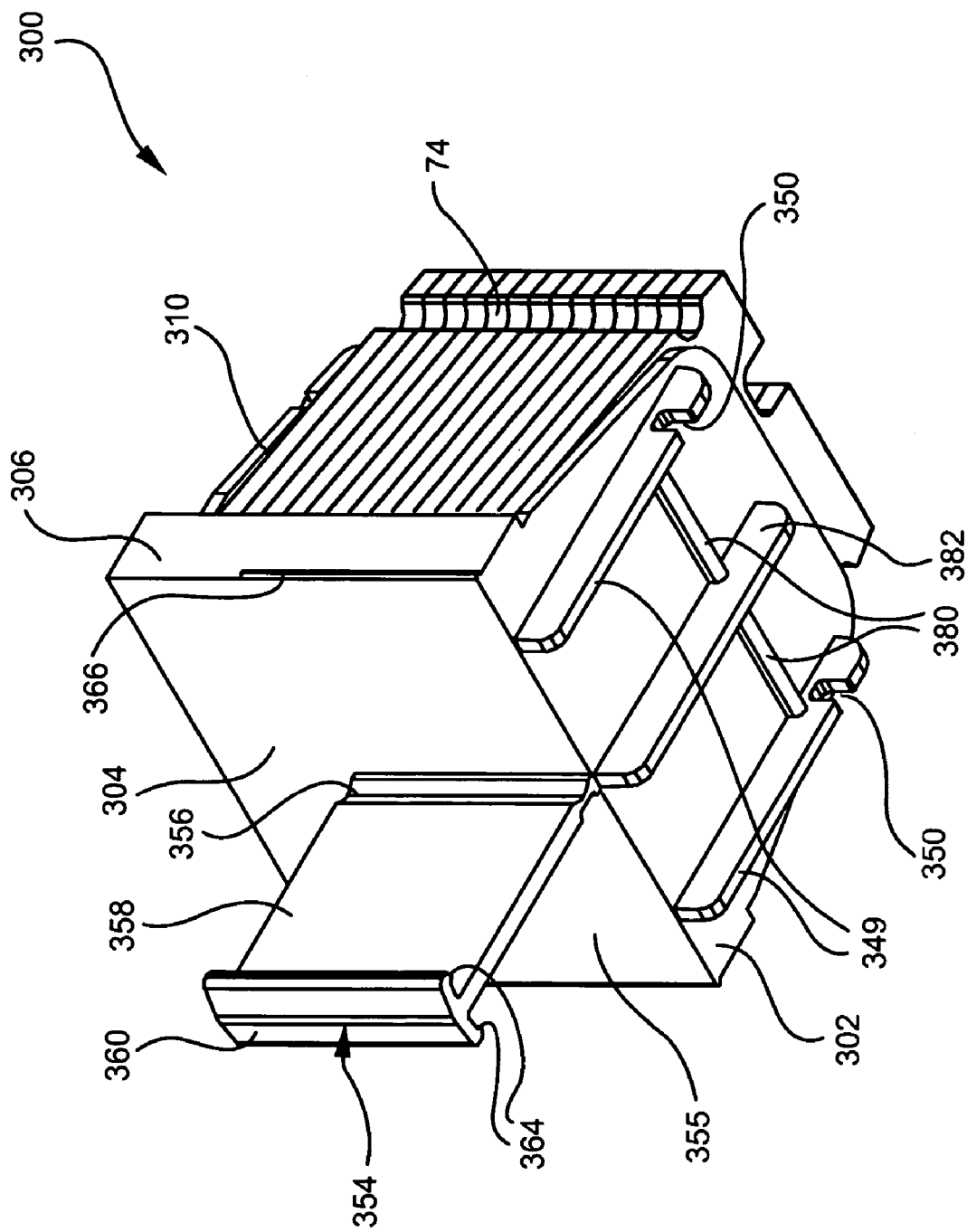
FIG. 28 is a rear isometric view of the retaining clip shown in FIG. 23 and shown holding a plurality of reagent test slides and with a part thereof shown in an extended position.

FIGS. 27 and 28 illustrate the retaining clip 300 of this embodiment holding a plurality of chemical reagent test slides 70 in a stacked arrangement. Any number of reagent test slides 70 may be held in place between the top cover plate 310 and the bottom cover plate 302 and the opposite lateral side walls 306, 308, as the top cover plate 310 may move on the T-shaped rail 328 with respect to the bottom cover plate 302 and be spaced from the bottom cover plate 302 at any desired distance.

As in the previous embodiment shown in FIGS. 17 through 22, the top and bottom cover plates 310, 302 may include ribs 348 and 349 extending outwardly respectively from the top and bottom surfaces thereof, which ribs 348, 349 have recesses 350 formed therein to receive and hold in place an elastic band 352 which encircles the top and bottom cover plates 310, 302 of the retaining clip 300 and the plurality of reagent test slides 70 situated therebetween. These recesses 350 may also be formed in the lateral edges of the top cover plate 310 to further receive and help hold in place the elastic band 352. As in the previous embodiment, the retaining clip 300 may have its top cover plate 310 and bottom cover plate 302 formed with additional transverse and longitudinal ribs 380, 382, 384, 386, 388 projecting outwardly from the outer surfaces thereof to help strengthen the top and bottom cover plates 310, 302.

Furthermore, the top and bottom cover plates 310, 302 preferably extend outwardly from the front surface 312 of the back wall 304 a sufficient distance to cover the film portion 73 of the top slide 78 and bottom slide 76 in the stacked arrangement of slides 70 to minimize the evaporation of any analyte deposited thereon, but does not extend so far outwardly as to cover the recesses 74 formed in the lateral edges 72 of the reagent test slides 70 or the orientation notch 82 formed in the front edge 80 of the slides to allow the entire stack of test slides 70, while still held by the retaining clip 300, to be loaded onto a slide injector mechanism of a chemical analyzer, such as will be described and which cooperates with this and the other embodiments described herein. Additionally, the preferred shape of the top cover plate 310 and bottom cover plate 302 conforms at least partially to the overall shape of the reagent test slides 70.

As in the previous embodiment illustrated by FIGS. 17-22, the third embodiment illustrated by FIGS. 23-28 includes a handle 354 for grasping by the user. The handle 354 extends outwardly and preferably perpendicularly from the rear surface 355 of the back wall 304 and is connected to the rear surface 355 through a bi-directional living hinge 356. Unlike the previous embodiment illustrated by FIGS. 17-20, in this particular embodiment, the bi-directional living hinge 356 is used to mount the handle 354 to the back wall 304 and to allow the handle 354 to be moved from its outwardly extended position to a folded, unextended position against or in close proximity to the rear surface 355 of the back wall 304 in the direction of either one lateral side wall 306 or the other lateral side wall 308.

Preferably, the handle 354 is T-shaped in longitudinal cross-section, and is formed with an extended portion 358 which is joined to the living hinge 356, and a transverse section 360 mounted on the free end of the extended portion 358 and extending outwardly and generally perpendicularly from opposite sides thereof to define the handle 354 with an overall T-shape in cross-section. At each end of the transverse section 360 is a bulbous member, or barb 364, which is used to secure the handle 354 in its folded, unextended position against or in close proximity to the rear surface 355 of the back wall 304 of the retaining clip 300. For this purpose, a bead 366 extends outwardly from each lateral side wall 306, 308 at the corner defined by the rear surface 355 of the back wall 304 and the outer surfaces of the lateral side walls 306, 308, which bead 366 runs at least partially along each lateral side wall 306, 308 from the bottom edge 368 of the back wall 304 at least partially toward the top edge 320. The handle 354 is particularly dimensioned with respect to the length of the extended portion 358 and the length of the transverse portion 360 such that, when it is moved to its folded, unextended position, the bulbous end or barb 364 engages and rises over either bead 366 formed on each lateral side wall 306, 308 and comes to rest on the other side of the bead 366. The handle 354 and, for that matter, the entire retaining clip 300, are preferably formed from a plastic or polymer material such as polypropylene, polyethylene, polyurethane or the like, and this provides the handle 354 in particular, with some resiliency. Because of the resiliency of the handle 354, the barb 364 engages the bead 366 and flexes to ride up over the bead 366 to come to rest on the other side of the bead 366 so that the handle 354 is retained in its folded position.

When the user wishes to hold the retaining clip 300, he or she pries the transverse portion of the handle 354 away from the lateral side wall 306, 308 and back over the retaining bead 366, and pivots the handle 354 to its extended position. When the handle 354 is not in use, it may be folded in either direction against or near the rear surface 355 of the back wall 304, with the transverse portion 360 and in particular the bulbous portion or barb 364 thereof engaging the retaining bead 366.

A fourth embodiment of a slide retaining clip 400 formed in accordance with the present invention is illustrated by FIGS. 29-34 of the drawings. This fourth embodiment is similar in many respects in structure and function to the second and third embodiments illustrated by FIGS. 17-22 and FIGS. 23-28, respectively. In the fourth embodiment, the retaining clip 400 includes a back wall (also referred to herein as "middle plate") 404, opposite lateral side walls 406 and 408 extending preferably perpendicularly in the same direction from the back wall 404, and a bottom cover plate (also referred to herein as "second cover plate") 402 affixed to the back wall 404 and extending preferably perpendicularly therefrom in the same direction as the lateral side walls 406 and 408. A top cover plate (also referred to herein as "first cover plate") 410 is slidably attached to the back wall 404 of the retaining clip 400, as will be described in greater detail.

More preferably, the back wall 404 of the retaining clip 400 is formed with a plurality of undulations 412 which extend outwardly and inwardly from the front surface 414 thereof. These undulations 412 are used to maintain the position of the top cover plate 410 in place on the back wall 404 of the retaining clip 400 and to prevent its lateral movement while allowing a sliding, longitudinal movement on the back wall 404 of the retaining clip 400.

More specifically, the top cover plate 410 includes a main body portion 416, and two opposite plate-like extending side tabs 418 extending outwardly from the main body portion 416 and spaced apart from one another. Each tab 418 is received within a corresponding recess 420 defined by a corresponding lateral side wall 406 and 408 and a corresponding first shoulder projection 424 extending outwardly from the front surface 414 of the back wall 404. The recesses 420 defined between the corresponding lateral side walls 406 and 408 and first shoulder projections 424 are dimensioned to be slightly greater in width than the width of the side tabs 418 so as to closely receive the side tabs 418 but to allow their slidable movement therein. The recesses 420 extend at least partially along the length of the front, surface 414 of the back wall 404, from the inner surface 426 of the bottom cover plate 402 to the top edge 428 of the back wall 404.

A T-shaped rail 430 is also formed on the front surface 414 of the back wall 404 of the retaining clip 400 and extends outwardly therefrom from the inner surface 426 of the bottom cover plate 402 to the top edge 428 of the back wall. The T-shaped rail 430 has a narrow portion 432 and a widened portion 434 extending outwardly from the narrow portion 432 to provide the rail 430 with a "T"-shape in cross section. The T-shaped rail 430 is positioned between the two first shoulder projections 424 and define with the first shoulder projections 424 a pair of L-shaped slots 436 extending from the inner surface 426 of the bottom cover plate 402 to the top edge 428 of the back wall 404.

The top cover plate 410 further includes a pair of L-shaped projections 438 extending from the main body portion 416 in the same plane as the main body portion 416. The L-shaped projections 438 are disposed to face one another in mirrored symmetry so that, between them, they define a T-shaped slot 440 having a narrow portion 442 and a widened portion 444 communicating with the narrow portion 442. The spacing between the L-shaped projections 438 which define the narrow portion 442 is such as to be slightly greater than the width of the narrow portion 432 of the T-shaped rail 430, and the spacing between the L-shaped projections 438 which define the widened portion 444 of the slot 440 is such as to be slightly greater than the width of widened portion 434 of the T-shaped rail 430. In this way, the L-shaped projections 438 may be received by the corresponding L-shaped slots 436, and the T-shaped rail 430 may be received by the T-shaped slot 440 defined between the L-shaped projections 438 of the top cover plate 410. The shoulder projections 424 are similarly received by corresponding notches 419 formed in the rear edge of the top cover plate 410, each notch 419 being situated between and defined by an adjacent side tab 418 and L-shaped projection 438. Thus, the top cover plate 410 may be mounted on the front surface 414 of the back wall 404 of the retaining clip 400 and may be longitudinally (i.e., from top to bottom) slidably movable thereon with minimal lateral movement with respect to the back wall 404 of the retaining clip 400.

As in the other embodiments, the top cover plate 410 and the bottom cover plate 402 of the retaining clip 400 preferably at least partially conform to the general shape of the reagent test slides 70 held in place between them and extend outwardly from the front surface 414 of the back wall 404 a distance sufficient to cover the film portions 73 of the top and bottom reagent test slides 78, 76 in the stack of test slides 70 to help minimize evaporation of any analyte deposited thereon, but leave exposed the recesses 74 formed in the lateral edges 72 of the slides 70 and the orientation notch 82 formed in the front edge 80 of the slides to allow the entire stack of reagent test slides 70, while still held by the retaining clip 400, to be transferred to the slide injector mechanism of a chemical analyzer, as will be described in greater detail.

As in the third embodiment described previously and illustrated by FIGS. 23-28, this fourth embodiment of the retaining clip 400 may include an elastic band 450 to help secure the plurality of reagent test slides 70 in place on the retaining clip 400 between the lateral side walls 406 and 408 and the top cover plate 410 and the bottom cover plate 402. Structure is provided on preferably each of the top cover plate 410 and the bottom cover plate 402 to facilitate the placement of the elastic band 450 about the retaining clip 400 and slides 70 held thereby.

More specifically, each of the top cover plate 410 and the bottom cover plate 402 may include a pair of parallel first ribs 452, 454 respectively projecting outwardly from the outer surfaces 456, 458 thereof. In each of the first ribs 452, 454 of each of the top cover plate 410 and bottom cover plate 402 is formed a recess 464 which is dimensioned to be able to receive and help hold in place the elastic band 450. The ribs 452, 454 may further include larger projections situated on one or both sides of the recesses 464 to further help hold the elastic band 450 within the recesses. A third rib or plate 466 may extend transversely between the pair of first ribs 452 on the top cover plate 410, and extends outwardly from the outer surface 456 of the top cover plate 410. This third rib or plate 466 is preferably positioned near the recesses 464 formed in the first ribs 452 and preferably on the side of the recesses 464 closer to the back wall 404 of the retaining clip 400 so as to help guide the placement of the elastic band 450 onto the retaining clip 400 and the stack of reagent test slides 70 held thereby, as the placement of the elastic band 450 about the retaining clip 400 is preferably from the narrower front edge 80 of the reagent test slides 70 and not over the back wall 404 of the retaining clip 400, so that the transverse third rib or plate 466 acts as a back wall or stop for the elastic band 450 as it is placed about the retaining clip 400.

Even more preferably, each of the top cover plate 410 and bottom cover plate 402 may respectively include a central fourth rib 468, 470 which is positioned between the pair of first ribs 452, 454 and which also extends outwardly from the outer surface 456, 458 of each of the top cover plate 410 and bottom cover plate 402. This fourth rib 468, 470 has at least a portion thereof which has a height above the outer surface 456, 458 of the top cover plate 410 and the bottom cover plate 402 which is greater than the height of the pairs of first ribs 452, 454. A central rib, on either or both cover plates enhances compression at the center of the cover plates. Optional fifth ribs 476, 478 can be positioned preferably transversely to the pairs of first ribs 452, 454 and the fourth ribs 468, 470 to provide additional strength to the top cover plate 410 and bottom cover plate 402.

The elastic band 450 rests and exerts pressure on the raised portion of the fourth ribs 468, 470 and thereby causes pressure to be exerted in the central area of each of the top cover plate 410 and bottom cover plate 402. This ensures that the top cover plate 410 and bottom cover plate 402 tightly contact respectively the top and bottom slides 78, 76 of the stacked arrangement of slides 70 and to ensure that the top cover plate 410 and bottom cover plate 402 closely cover the film portion 73 of the top and bottom slides 78, 76 in the stack to minimize any evaporation of the analyte deposited thereon.

This fourth embodiment of the retaining clip 400, like many of the previous embodiments described, includes a handle 481 for grasping by the user. The handle 481 extends outwardly from the rear surface 480 of the back wall 404 of the retaining clip 400 in preferably a perpendicular direction therefrom. However, it may be folded and secured in place against or in proximity to the rear surface 480 of the back wall 404 when it is not being used, in order to reduce the overall dimensions of the retaining clip 400.

More specifically, the handle 481 is mounted to the rear surface 480 of the back wall 404 of the retaining clip 400 by using a living hinge 482. The living hinge 482 allows the handle 481 to be moved from its perpendicularly extended position to a position where it is flush against, or in close proximity to, the rear surface 480 of the back wall 404 of the retaining clip 400. The handle 481 is preferably L-shaped in cross-section with a longer first leg portion 484 and a shorter second leg portion 486 extending preferably perpendicularly from the first leg portion 484. The second leg portion 486, at its free end, includes a tab 488 for grasping by the user which extends to an inwardly projecting shoulder 490 spaced apart from the first leg portion 484. At least one lateral side wall 406, 408 of the retaining clip 400 includes an elongated recess or groove (also referred to herein as "receiving slot") 494 formed in the outer surface 496 thereof, which recess, groove or receiving slot 494 is dimensioned to receive the inwardly extending shoulder 490 of the handle 481 and to hold the handle 481 in place in close proximity to the rear surface 480 of the back wall 404 when the handle 481 is folded against the back wall 404 when not in use. When the user wishes to extend the handle 481, he or she grasps the tab 488 to force the shoulder 490 out of the recess, groove or receiving slot 494 formed in the side wall 406, 408, and pivots the handle 481 about the hinge 482 from its unextended position to its extended position. Preferably, the handle 481 and, for that matter, the entire retaining clip 400, is formed from a plastic material, or a polymer, such as those described in relation to the other embodiments, thus providing the handle 481 with some resiliency so that the inwardly extending shoulder 490 may be resiliently received by, and removed from, the recess, groove or receiving slot 494 formed in one or more of the lateral side walls 406, 408 of the retaining clip 400.

FIGS. 35 through 39 show a fifth embodiment of a slide retaining clip 500 formed in accordance with the present invention. The retaining clip 500 of this particular embodiment is preformed to a particular shape. It includes a bottom cover plate (also referred to herein as "second cover plate") 502 and a top cover plate (also referred to herein as "first cover plate") 506 overlying the bottom cover plate 502 and spaced apart therefrom by a predetermined distance H5. The bottom cover plate 502 and the top cover plate 506 reside generally in parallel, spaced apart planes.

The bottom cover plate 502 and the top cover plate 506 extend from opposite top and bottom edges 508, 510 of a rear or back wall (also referred to herein as "middle plate") 504 and are affixed thereto preferably perpendicularly from one side 512 thereof. A handle 514 extends preferably perpendicularly from the other side 516 of the back wall 504. The handle 514 is provided so that the user may grasp the retaining clip 500 without having to touch the reagent test slides 70 held thereby.

Preferably, the bottom cover plate 502 is curved over its extended length from where it joins the back wall 504 at 510 to its free end 518. More specifically, the bottom cover plate 502 is curved concavely, that is, toward the underside or inner surface 520 of the top cover plate 504. The material from which the retaining clip 500 is formed is preferably plastic or a polymer material, such as polypropylene, polyethylene, polyurethane or the like, or any other material such that it provides some resiliency to preferably both the bottom cover plate 502 and the top cover plate 506. At least, the bottom cover plate 502 is formed of a resilient material and, with its particular curvature, acts as a resilient leaf spring and applies pressure against a plurality of stacked reagent test slides to hold the test slides 70 between the bottom cover plate 502 and the top cover plate 506, as is illustrated by FIGS. 38 and 39 of the drawings.

Figure 38:
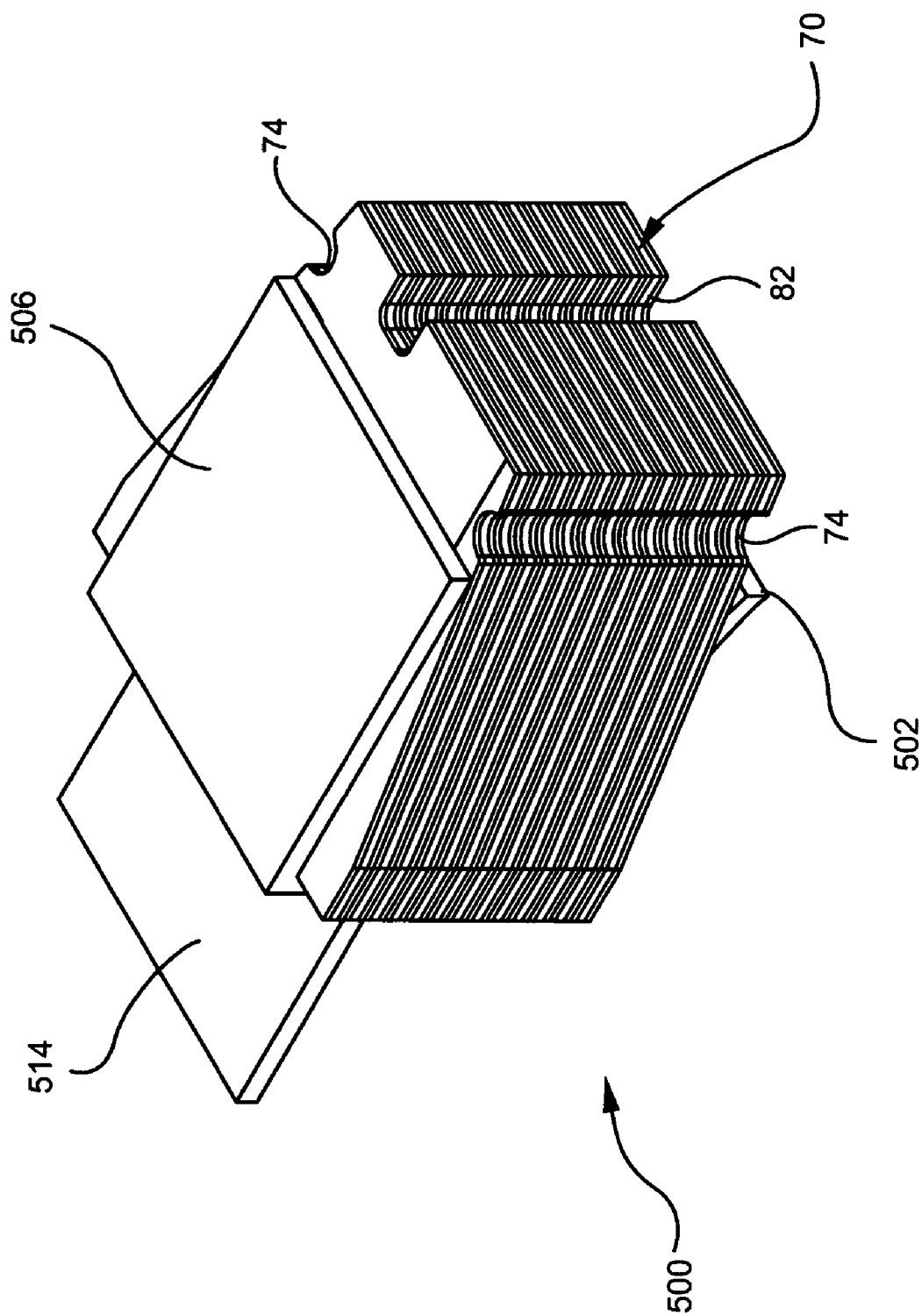
FIG. 38 is a front isometric view of the retaining clip shown in FIG. 35 holding a plurality of reagent test slides.
Figure 39:
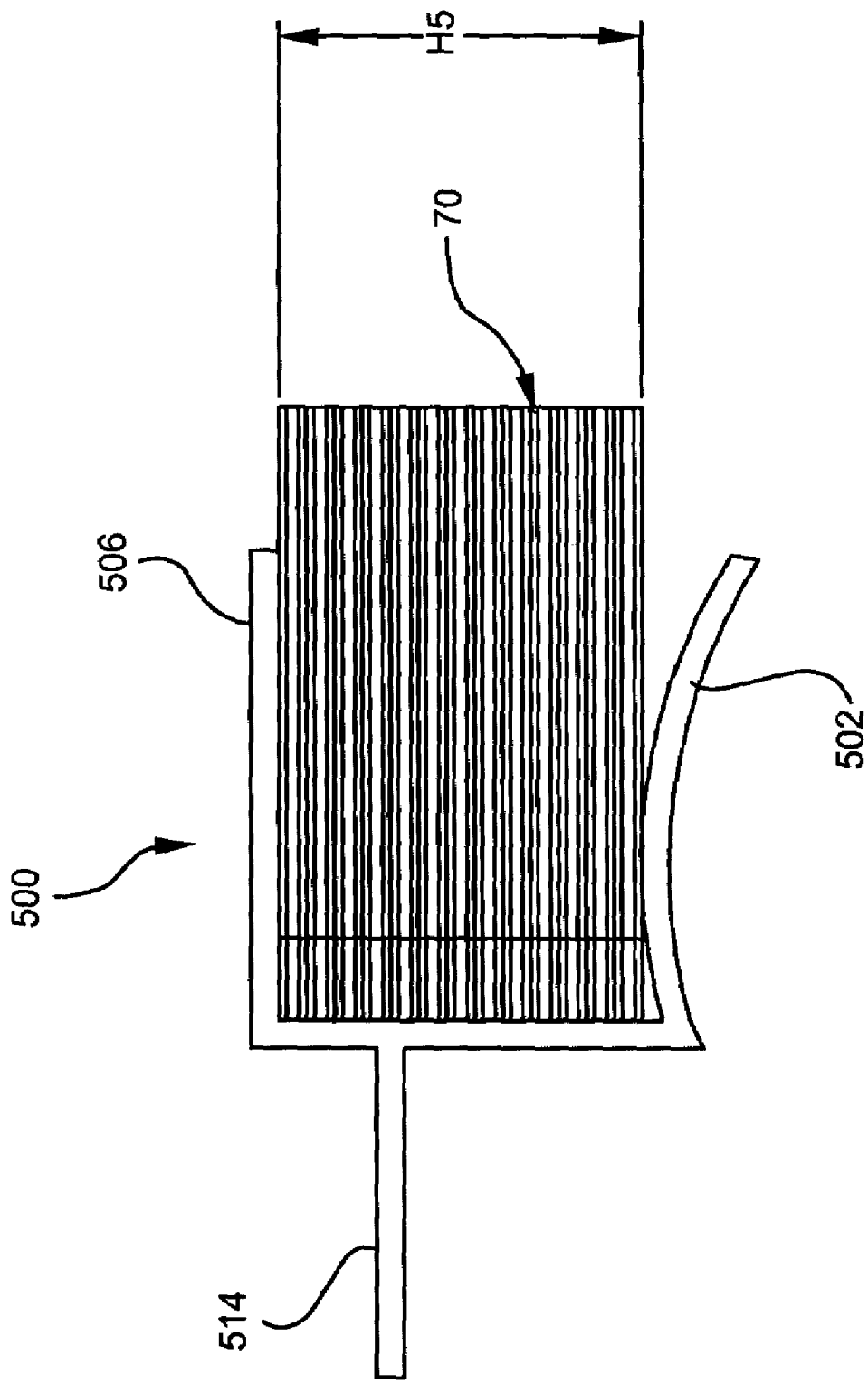
FIG. 39 is a side view of the retaining clip shown in FIG. 38 and shown holding a plurality of reagent test slides.

As can be seen from FIGS. 38 and 39, the bottom cover plate 502 and the top cover plate 506 are spaced apart from each other a predetermined distance H5 so that a particular number of slides in a stacked arrangement may be held in place between the two cover plates 502, 506. As shown by way of example in FIGS. 38 and 39, 14 slides 70 are held by the retaining clip 500. Of course, the retaining clip 500 may be dimensioned such that the bottom cover plate 502 is separated from the top cover plate 506 a predetermined distance H5 to hold a fewer number, or greater number, of reagent test slides 70 than that shown in FIGS. 38 and 39.

It should be further noted that, in the preferred form of the invention, the retaining clip 500 shown in FIGS. 35 through 39 has its bottom cover plate 502 and top cover plate 506 dimensioned in width and length such that at least the top cover plate 506 covers the film portion of the top reagent test slide 78 in the stack 70 but, neither the bottom cover plate 502 nor the top cover plate 506 extend so far as to cover the recesses 74 formed in the opposite lateral edges 72 of the slides to allow the slides 70 to be mounted, as a stack, onto the injector mechanism of the chemical analyzer, as will be described in greater detail. The top and bottom cover plates 506, 502 further preferably extend in length over the test slides such that they do not cover the orientation notch 82 formed in the front edge 80 of the slides.

Figure 35:
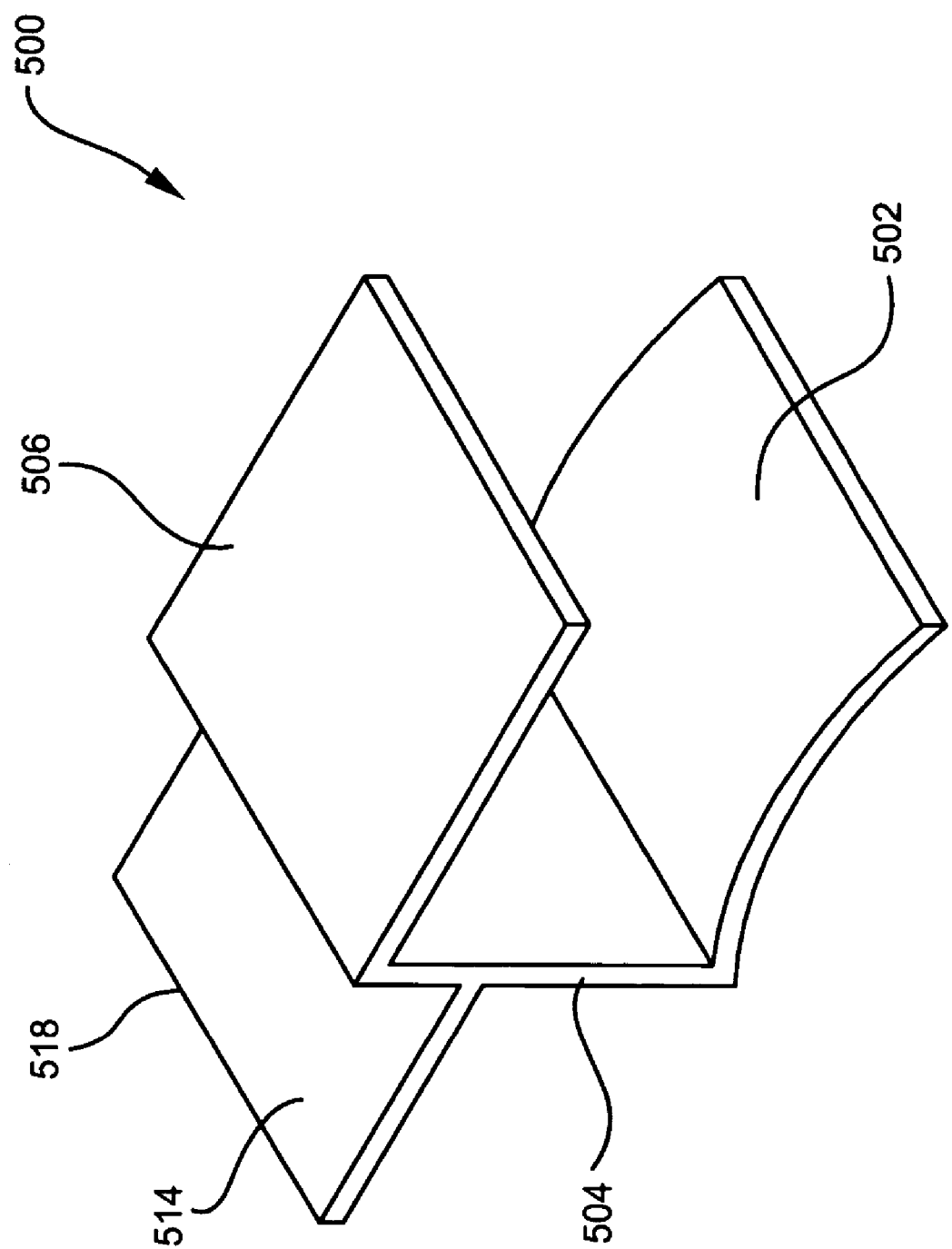
FIG. 35 is a front isometric view of a fifth embodiment of a retaining clip formed in accordance with the present invention.
Figure 36:
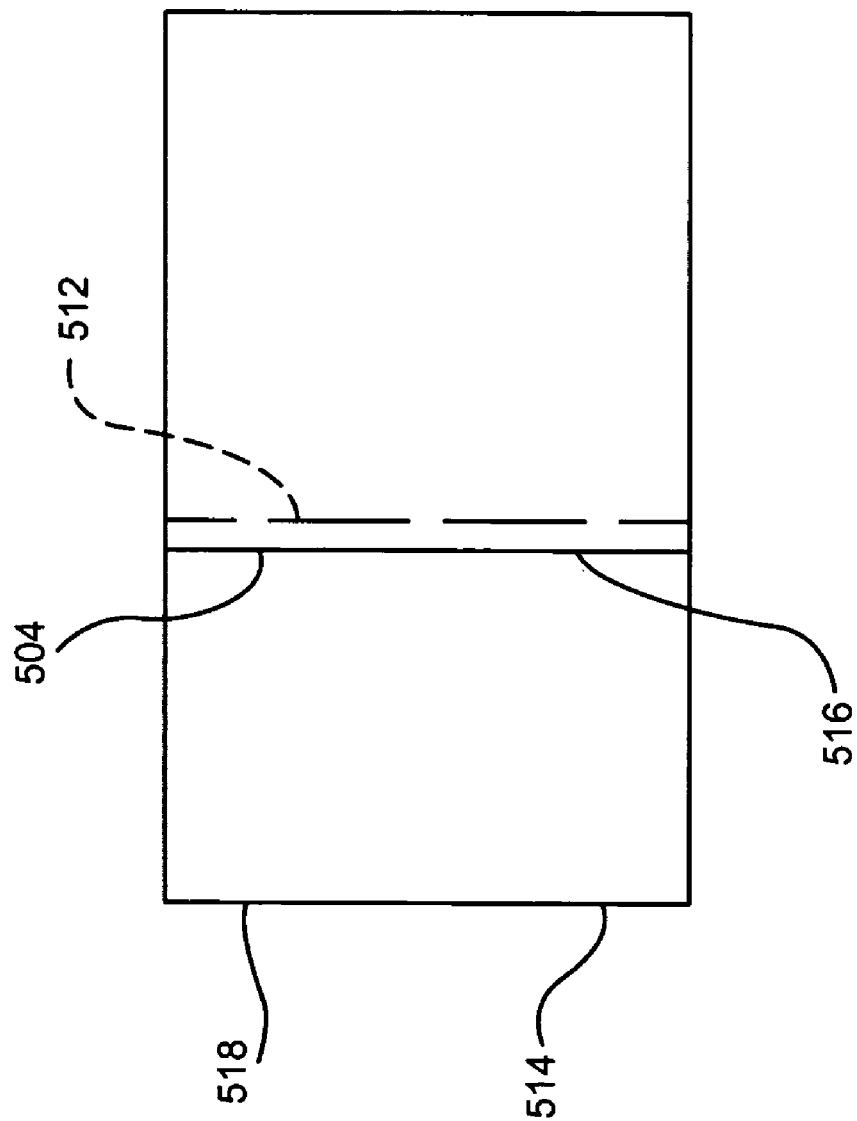
FIG. 36 is a top plan view of the retaining clip shown in FIG. 35.
Figure 40:
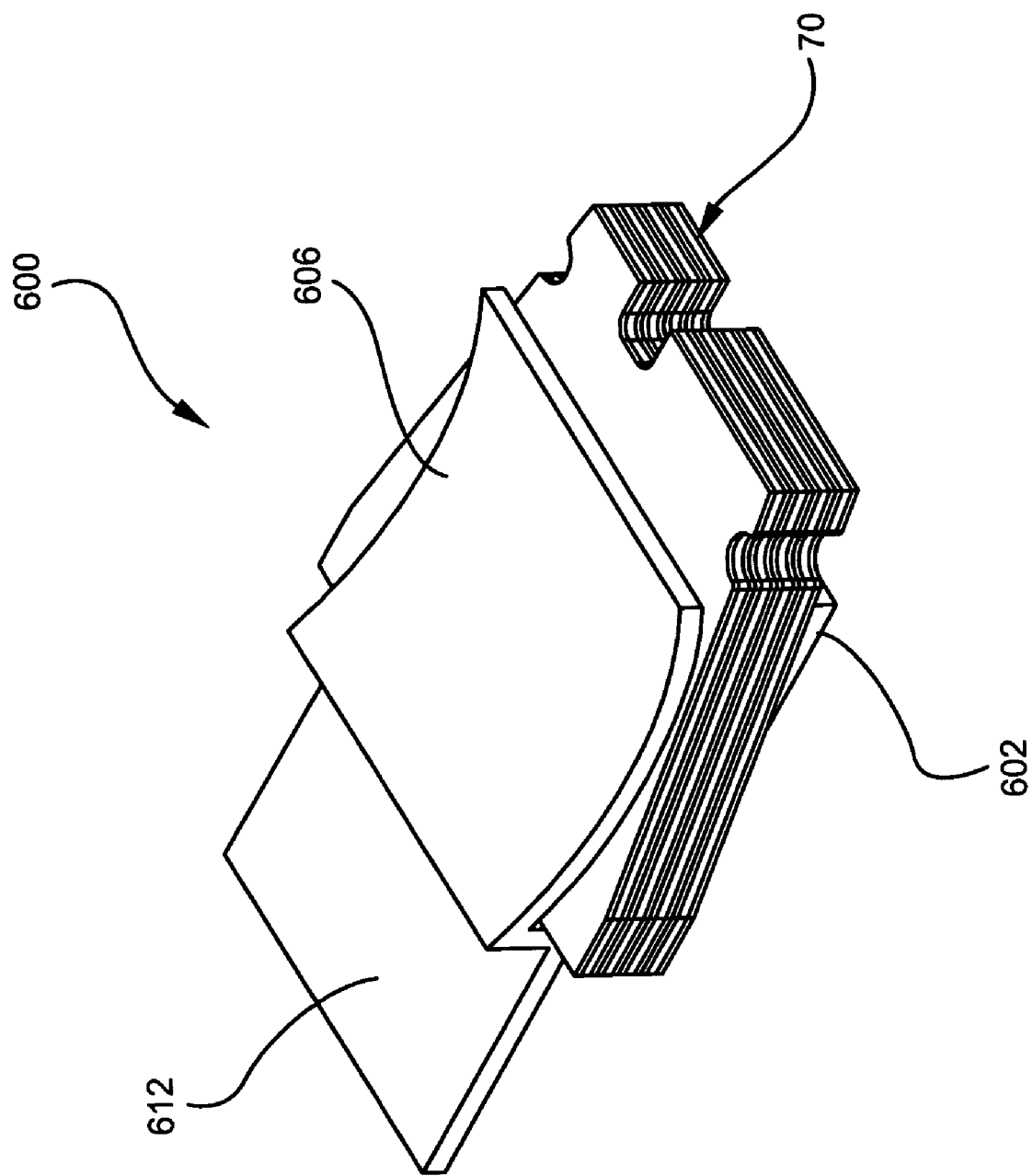
FIG. 40 is a front isometric view of a sixth embodiment of a retaining clip formed in accordance with the present invention, shown holding a plurality of reagent test slides.
Figure 41:
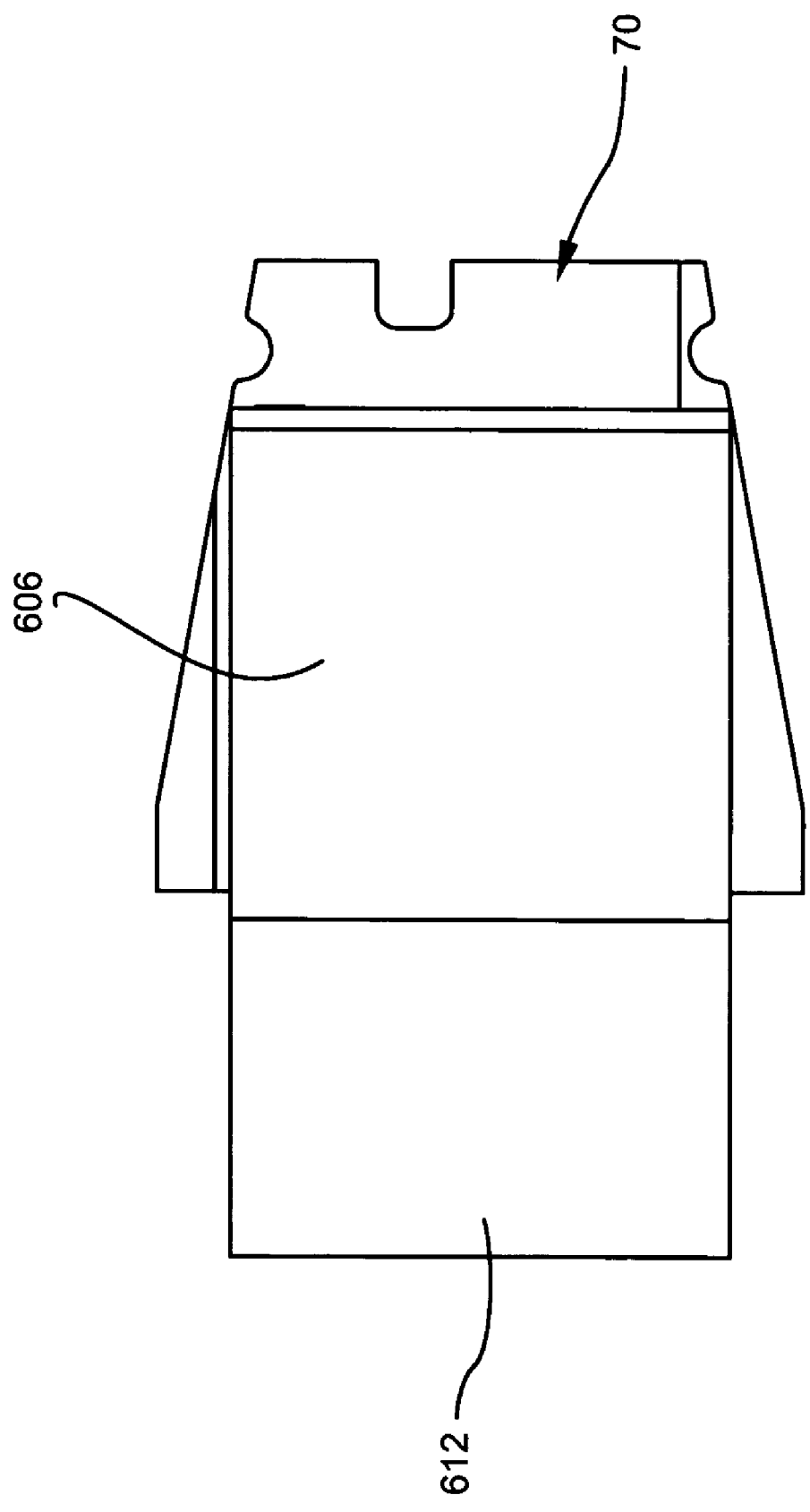
FIG. 41 is a top plan view of the retaining clip shown in FIG. 40 and shown holding a plurality of reagent test slides.
Figure 42:
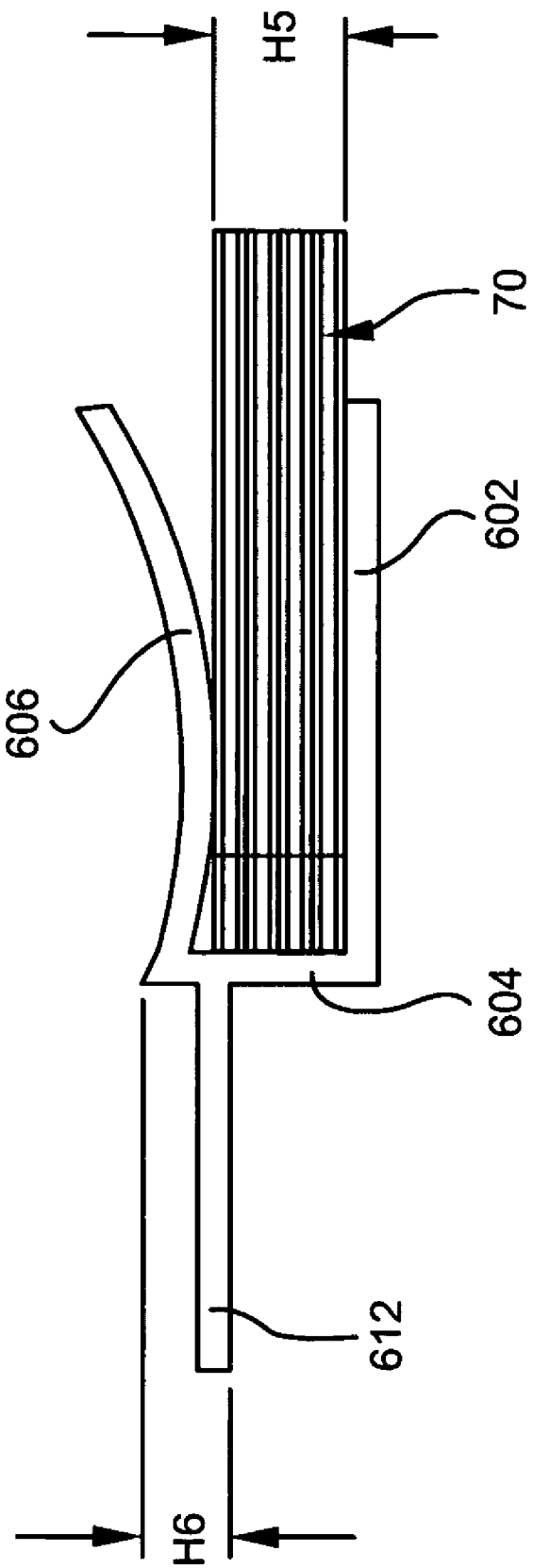
FIG. 42 is a side view of the retaining clip shown in FIG. 40 and shown holding a plurality of reagent test slides.

FIGS. 40-42 illustrate a sixth embodiment of a slide retaining clip 600 formed in accordance with the present invention. The sixth embodiment of the retaining clip 600 is very similar to the fifth embodiment 500 described previously and shown in FIGS. 35-39 of the drawings. In the sixth embodiment 600 shown in FIGS. 40-42, however, it is the top cover plate (also referred to herein as "first cover plate") 606 which is curved and acts as a resilient leaf spring, and the bottom cover plate (also referred to herein as "second cover plate") 602 is flat or planar in shape. Preferably, top cover plate 606 contacts the upper test slide closer to the leading edge of the slide (i.e., the edge with orientation notch 82) than the opposite/back slide edge. It should be further noted that the sixth embodiment 600 of the retaining clip shown in FIGS. 40-42 is dimensioned with less spacing H5 between the bottom cover plate 602 and the top cover plate 606 than that shown by way of example in FIGS. 35 39 illustrating the fifth embodiment of the present invention. Therefore, fewer reagent test slides 70, such as four slides as shown in FIGS. 40-42, are held in place by the retaining clip 600. Rear or back wall (also referred to herein as "middle plate") 604 and handle 612 are analogous to rear wall 504 and handle 514 of the fifth embodiment.

Figure 37:
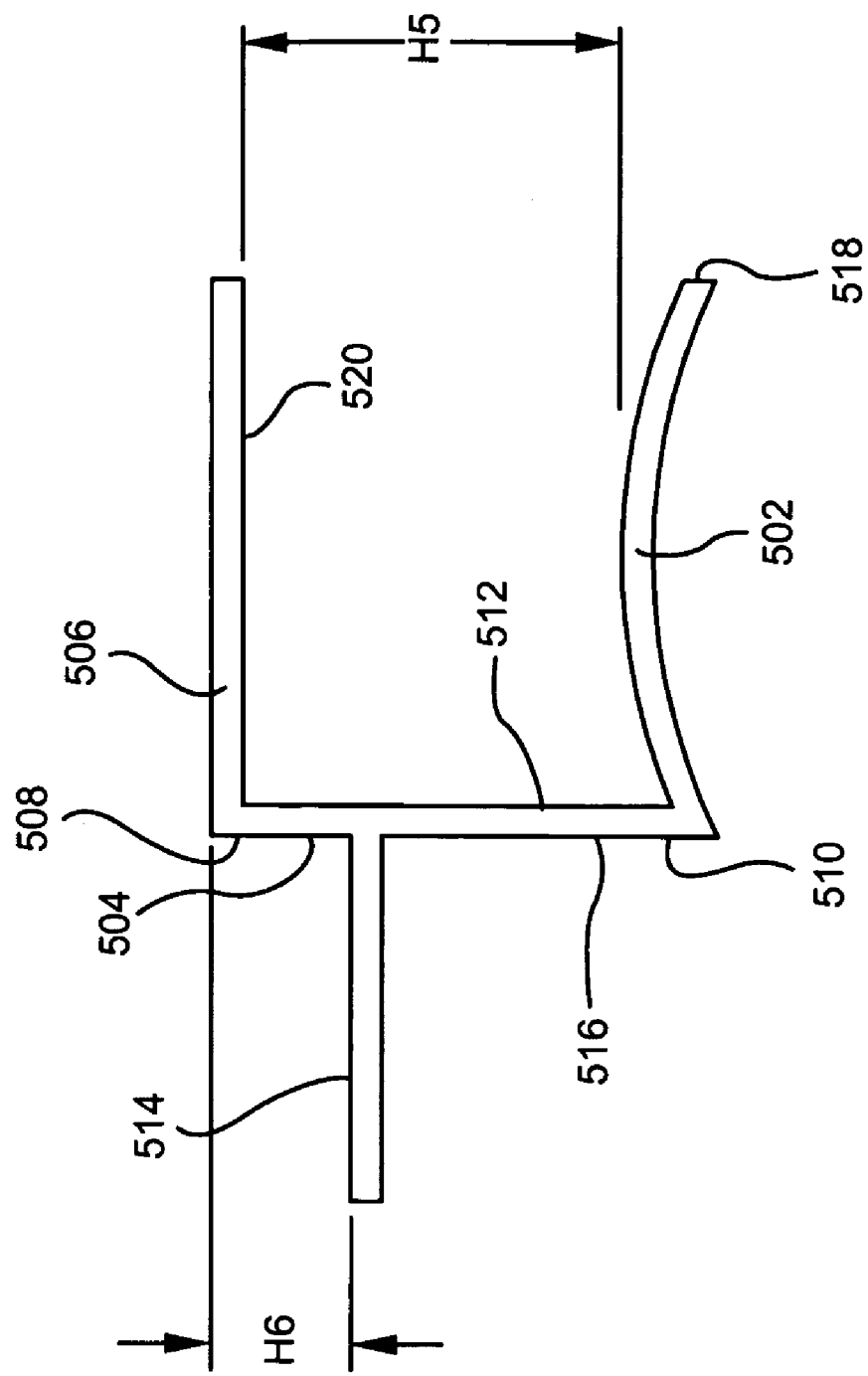
FIG. 37 is a side view of the retaining clip shown in FIG. 35.

It should be further noted that the handles 514, 612 respectively of the fifth embodiment shown in FIGS. 35-39 and the sixth embodiment shown in FIGS. 40-42 may be positioned on the back walls 504, 604 closer to where the top cover plate 506, 606 extends from the back wall 504, 604 than from where the bottom cover plate 502, 602 extends therefrom, as shown by dimension H6 in FIG. 37 and FIG. 42. This is to allow more space between the handle 514, 612 and the bottom or lower surface of the injector mechanism and so that the injector mechanism does not interfere with the user's grasp of the handles 514, 612 when the user is loading the stack of reagent test slides 70 held by the retaining clips 500, 600 onto the injector mechanism.

Both fifth and sixth embodiments are conducive to manufacture by either extrusion or molding. A resilient compression member, such as an O-ring, is optional.

Figure 19:
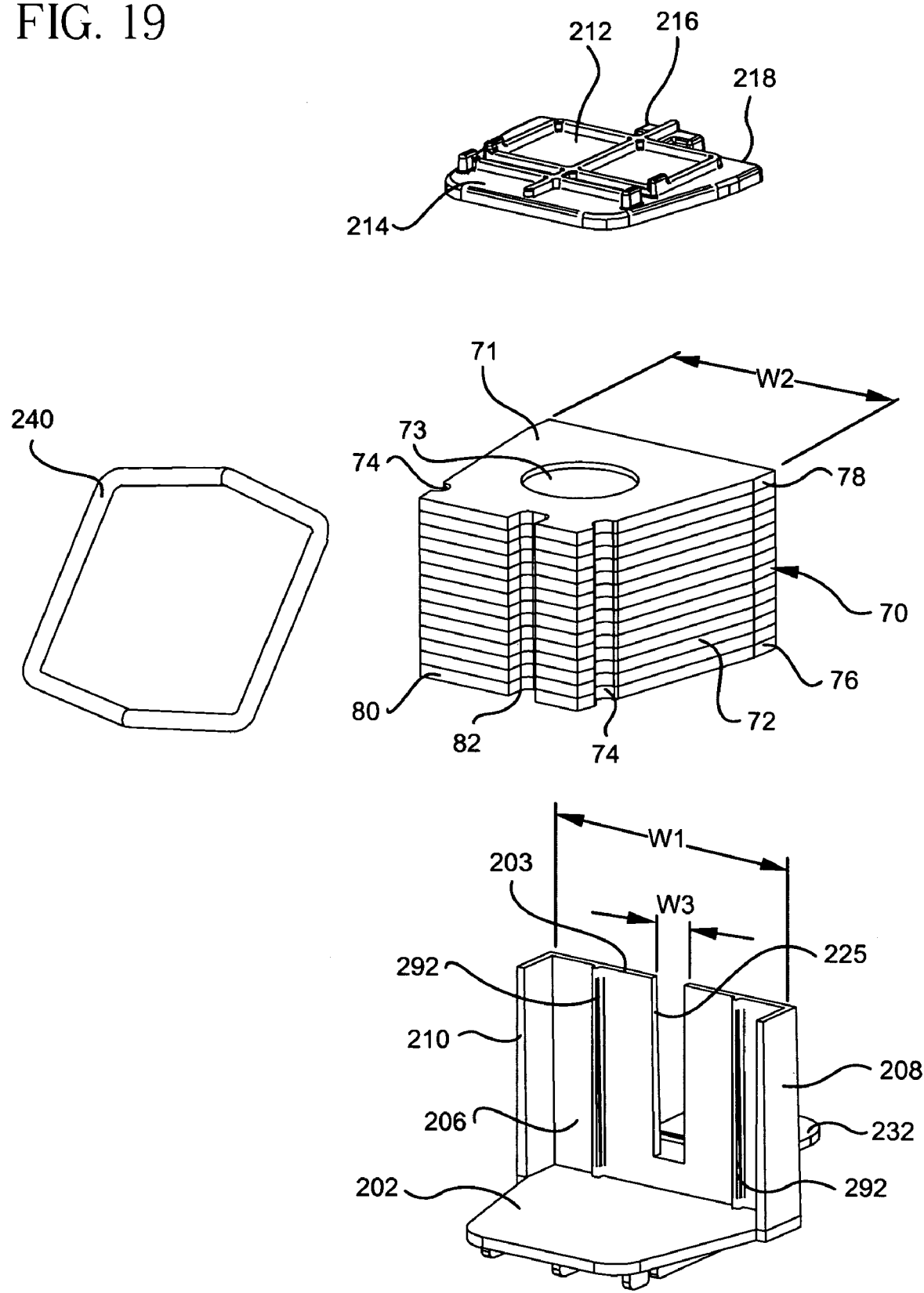
FIG. 19 is an exploded front isometric view of the retaining clip shown in FIG. 17.
Figure 20:
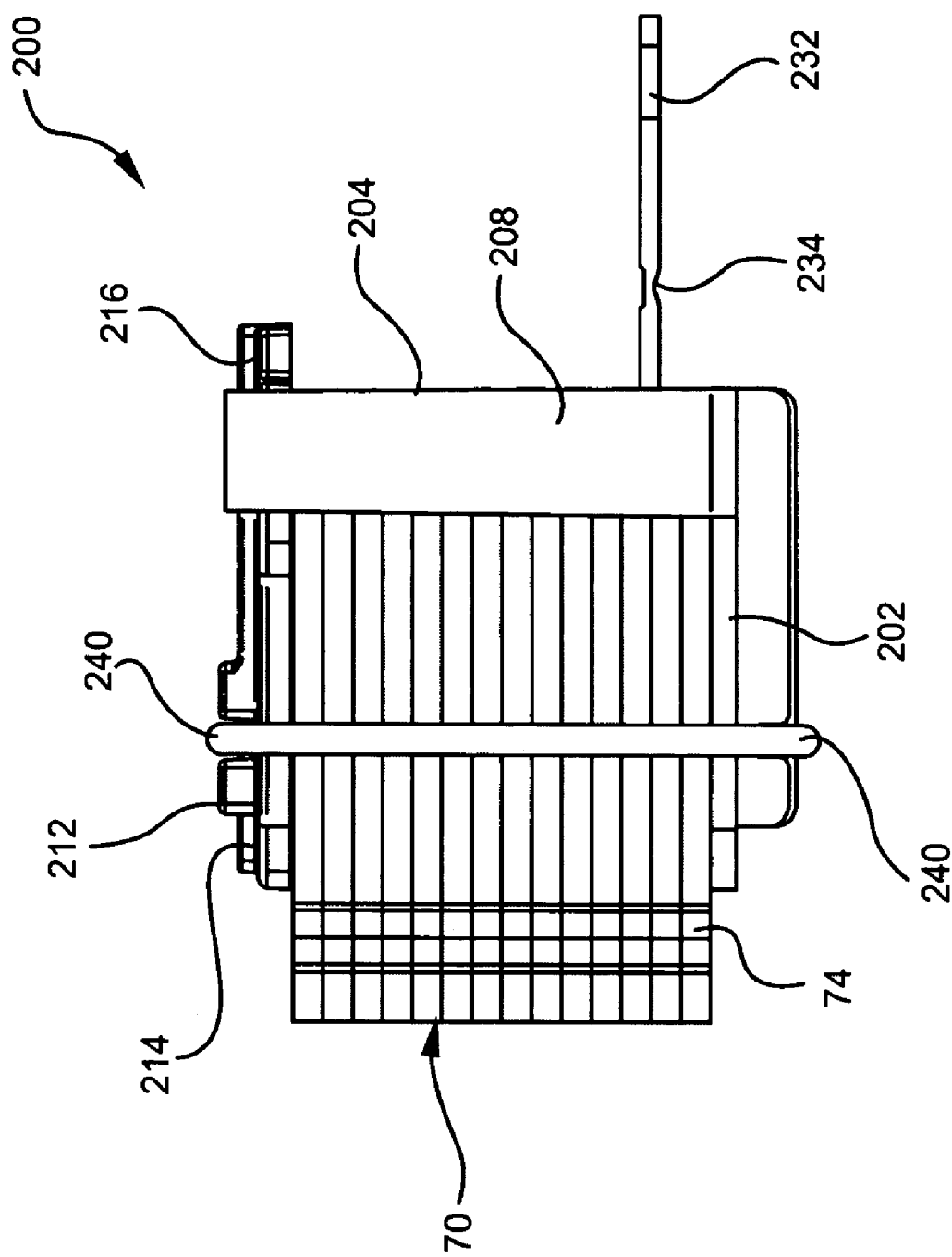
FIG. 20 is a side view of the retaining clip shown in FIG. 17.
Figure 23:
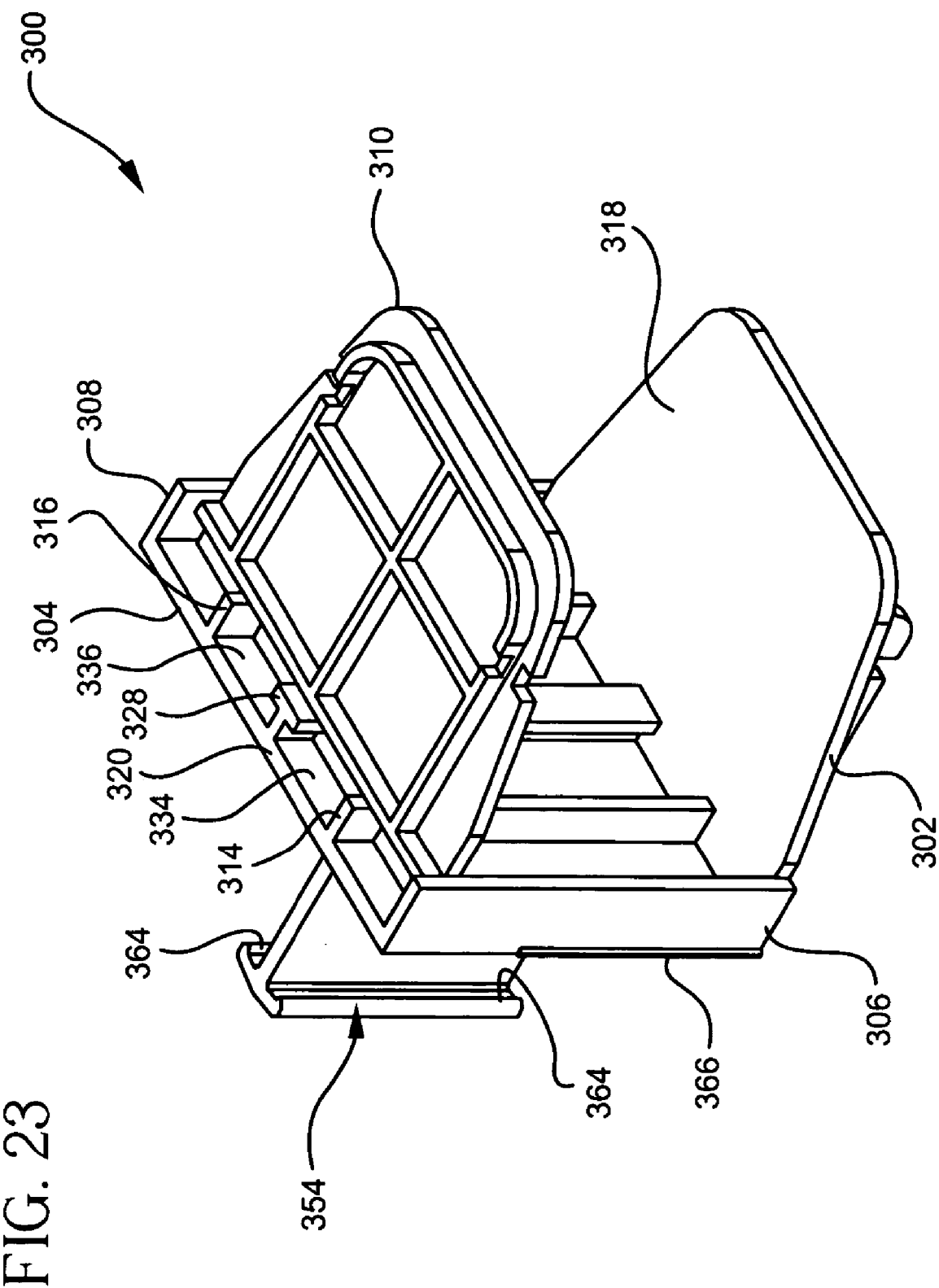
FIG. 23 is a front isometric view of a third embodiment of a slide retaining clip formed in accordance with the present invention.
Figure 24:
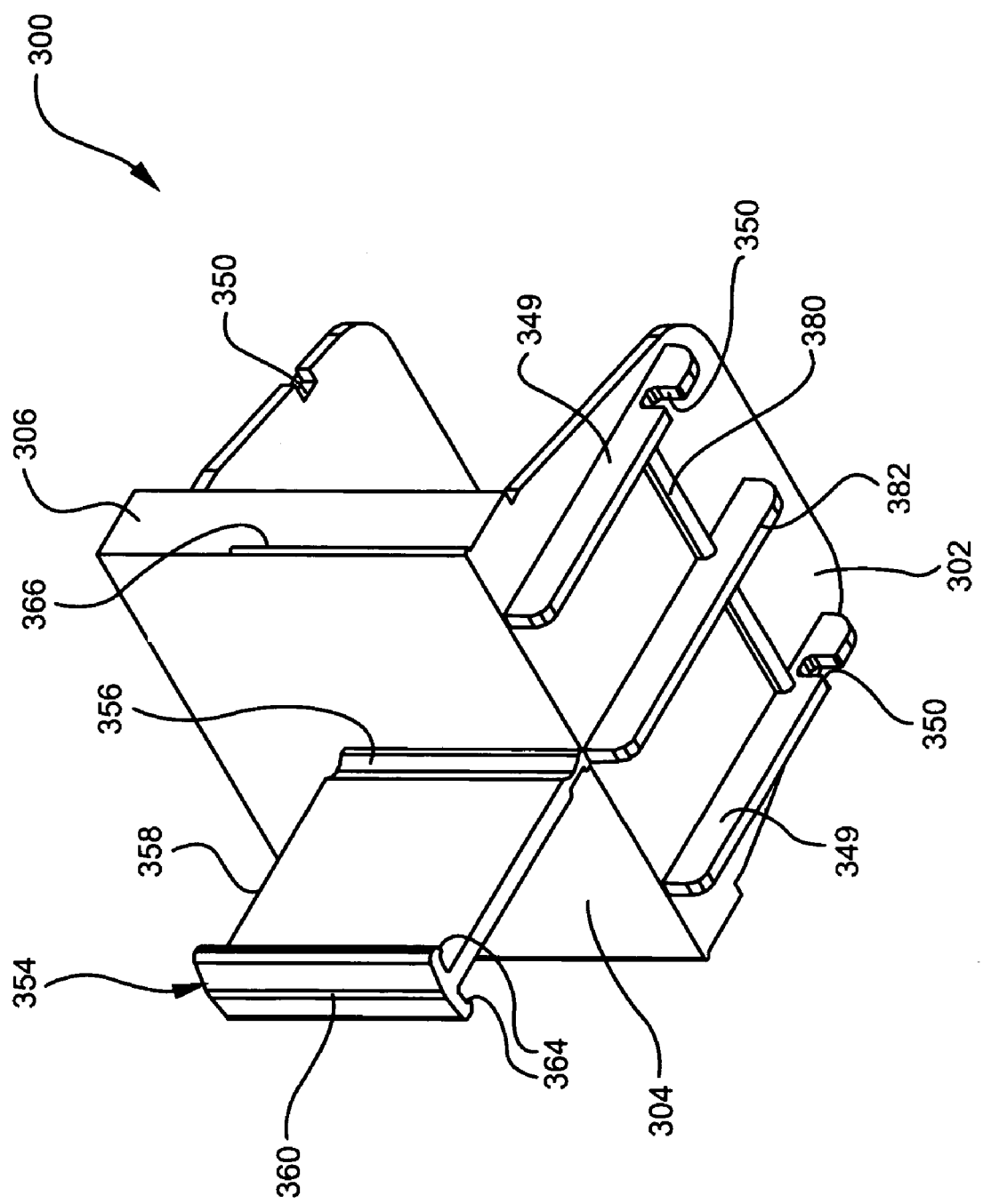
FIG. 24 is a rear isometric view of the retaining clip shown in FIG. 23.
Figure 25:
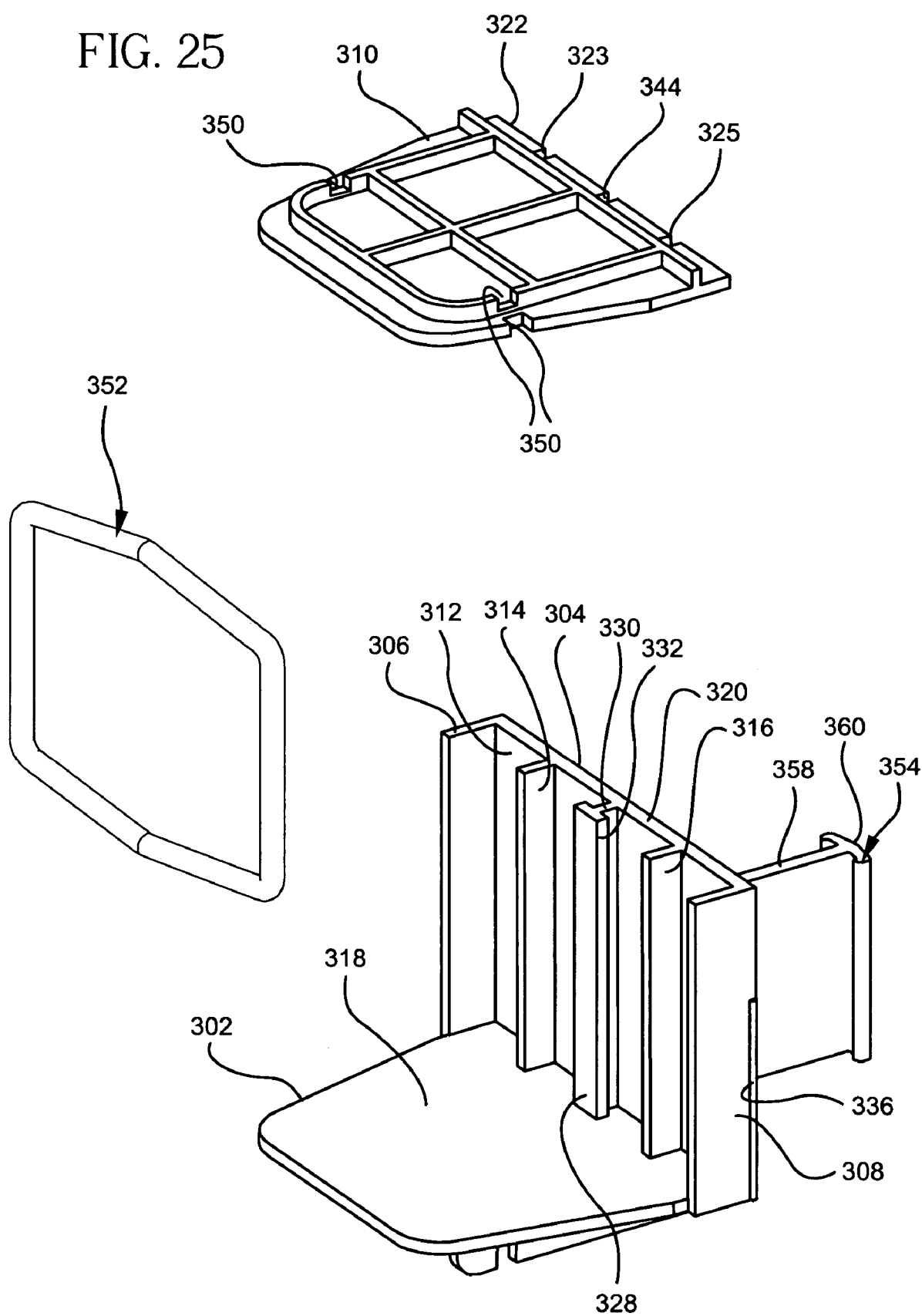
FIG. 25 is an exploded front isometric view of the retaining clip shown in FIG. 23.
Figure 26:
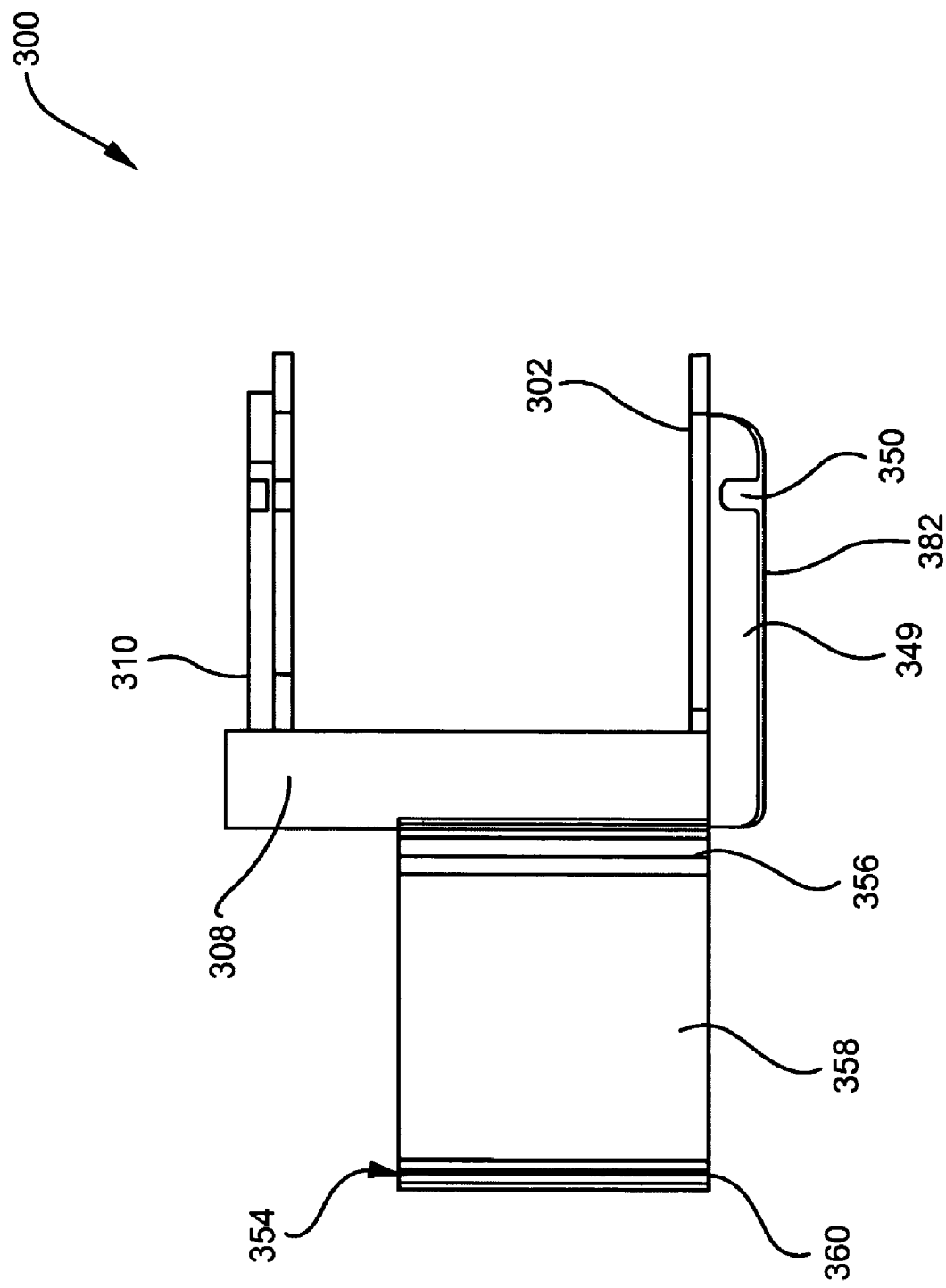
FIG. 26 is a side view of the retaining clip shown in FIG. 23.
Figure 31:
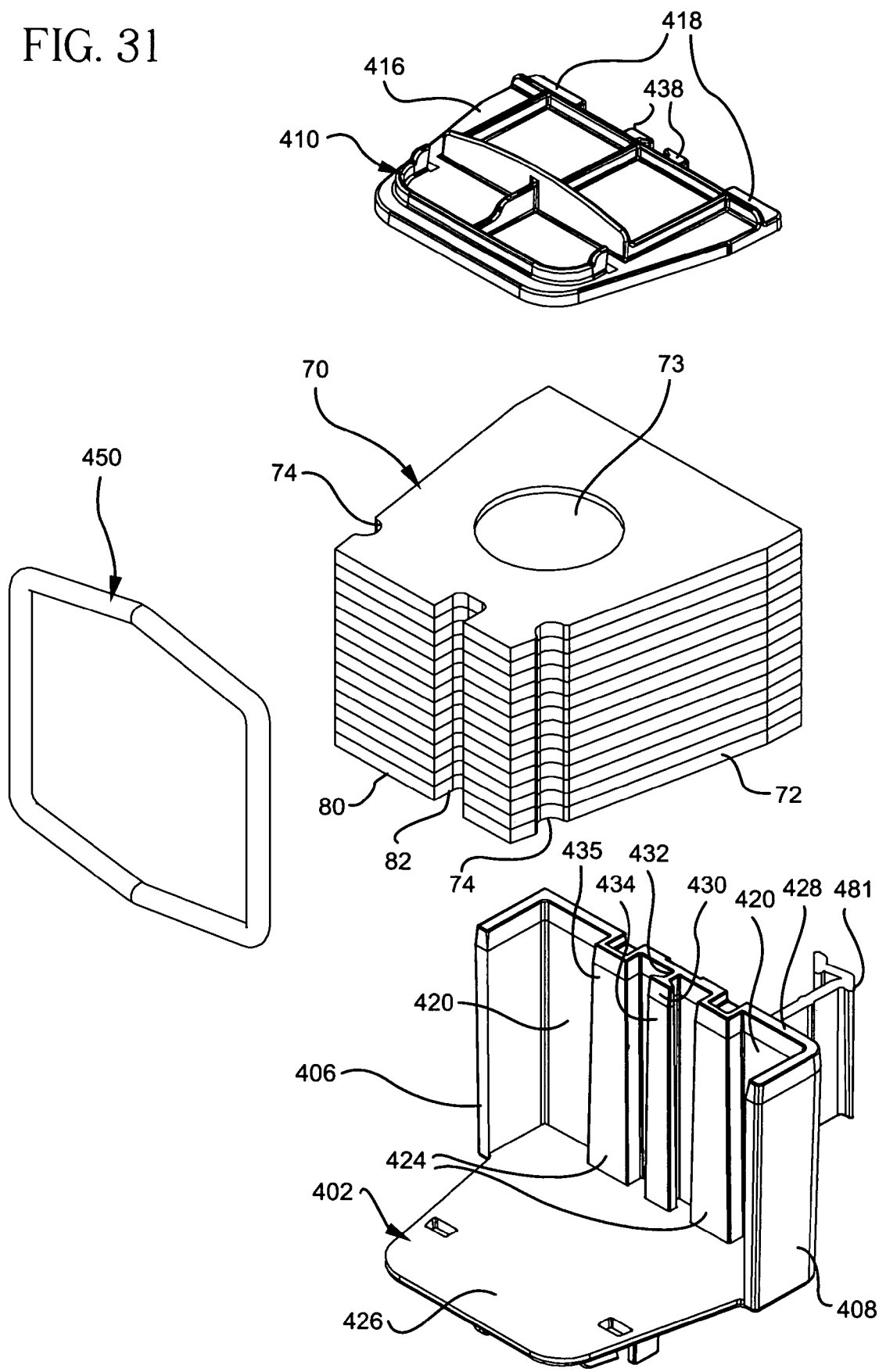
FIG. 31 is an exploded front isometric view of the retaining clip shown in FIG. 29.
Figure 31A:
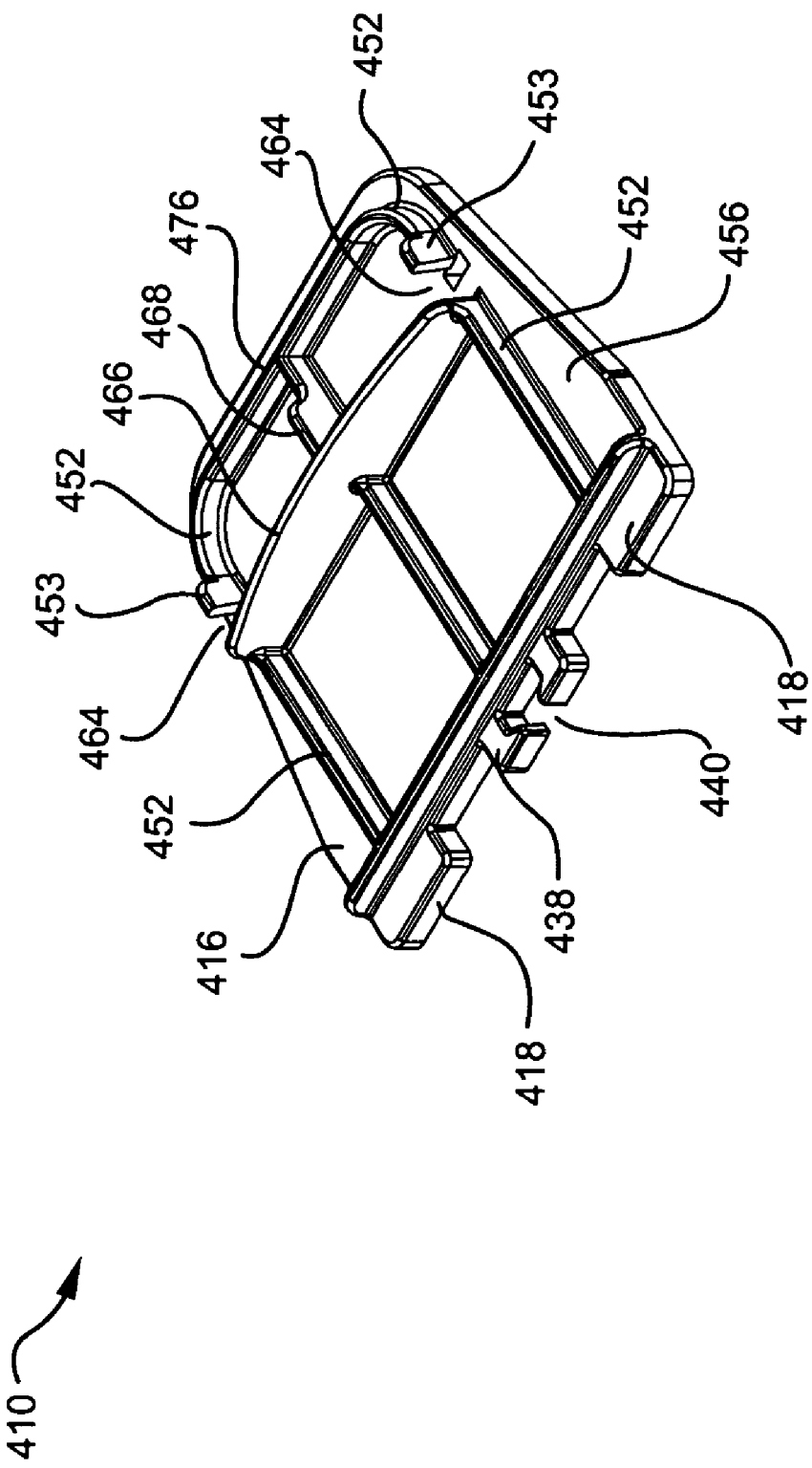
FIG. 31A is a top isometric view of a first portion of the retaining clip shown in FIG. 29.
Figure 31C:
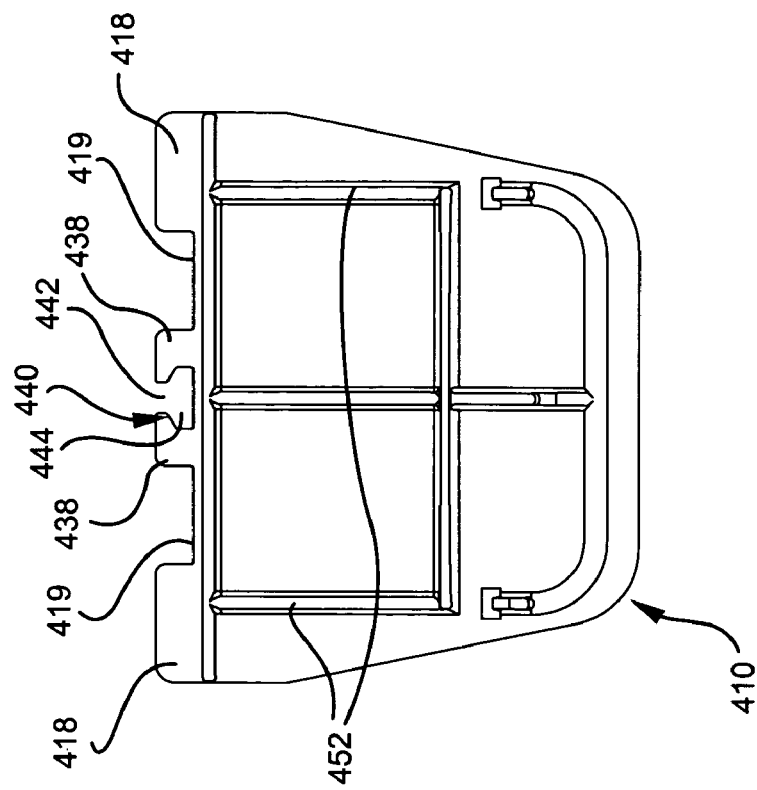
FIG. 31C is a top plan view of a second portion of the retaining clip shown in FIG. 29.
Figure 31B:
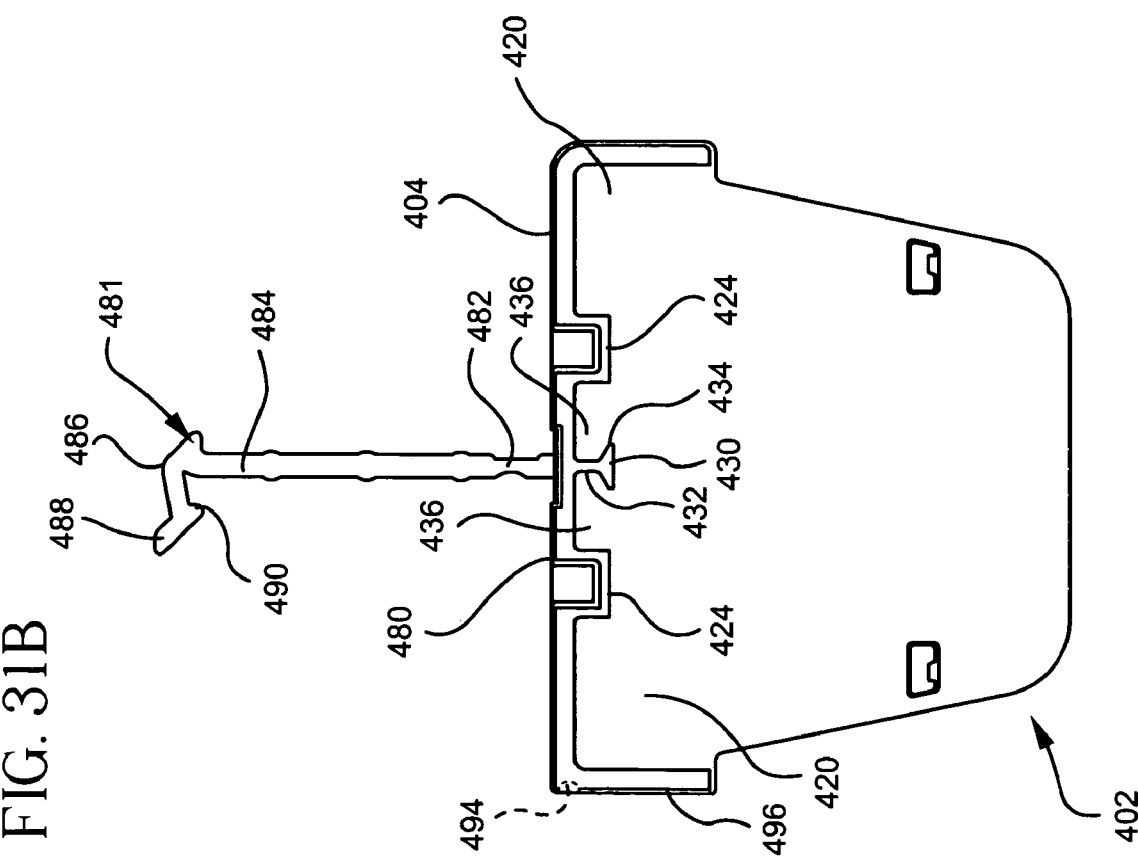
FIG. 31B is a top plan view of a first portion of the retaining clip shown in FIG. 29.
Figure 32:
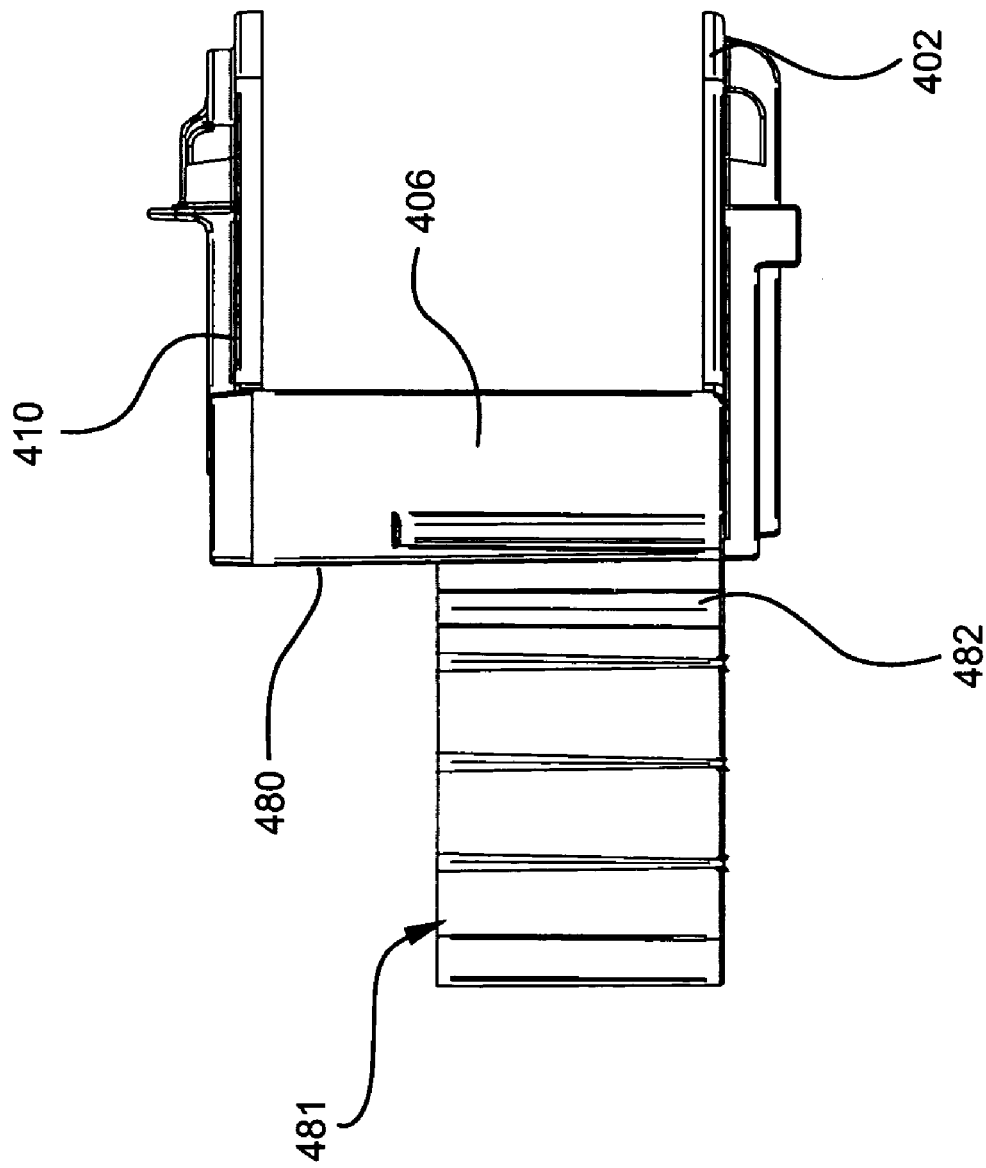
FIG. 32 is a side view of the retaining clip shown in FIG. 29.
Figure 33:
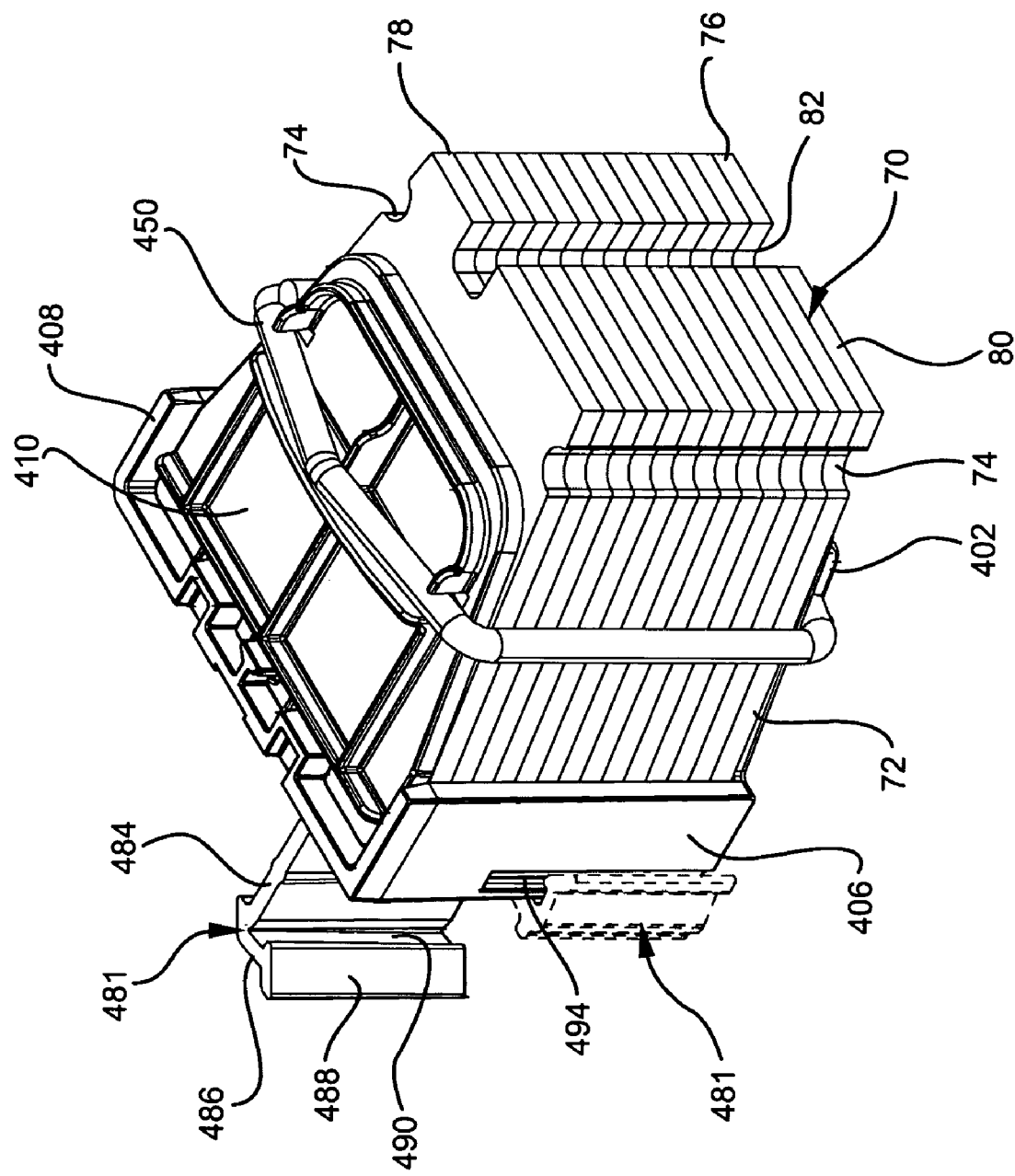
FIG. 33 is a front isometric view of the retaining clip shown in FIG. 29 and further shown holding a plurality of reagent test slides and having a part thereof shown in an extended state (in solid lines) and in an unextended state (in dashed lines).
Figure 34:
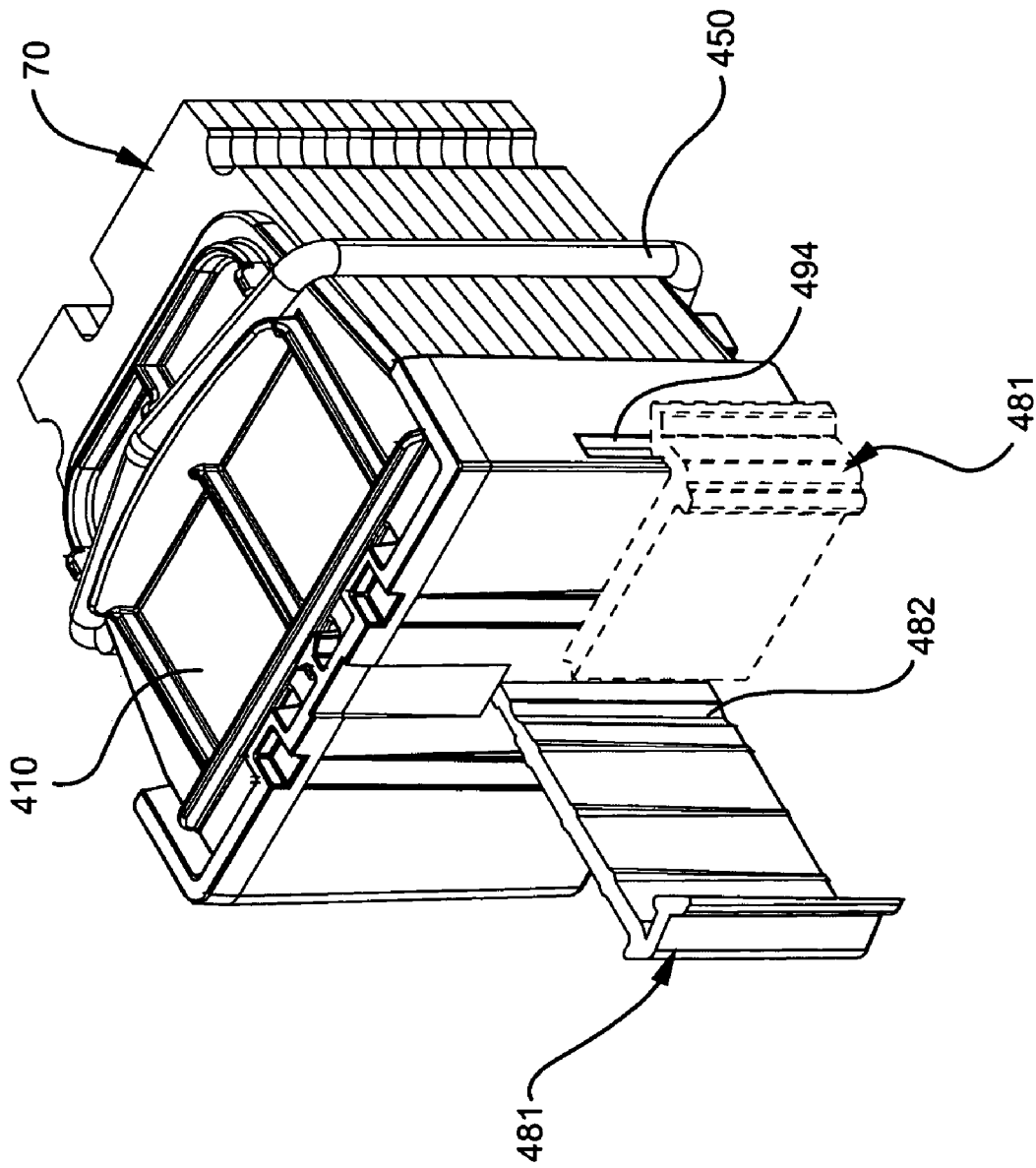
FIG. 34 is a rear isometric view of the retaining clip shown in FIG. 29 and shown holding a plurality of reagent test slides and having a part thereof shown in an extended state (in solid lines) and in an unextended state (in dashed lines).

As shown in FIGS. 19, 21 and 31 of the drawings, the test slides 70 have a frame 71 which may be either rectangular or trapezoidal in shape. The frame surrounds and supports a circular film portion 73 situated interiorly of the edges of the frame, which film portion 73 is coated with an analyte or chemical reagent, as is well known in the art. Common test slides used in biological fluid analysis include, for example, one for a calcium (Ca) test, another for an aspartate transminase (AST) test, and a third for a glucose (Glu) test.

In many of the embodiments described herein, the top and bottom cover plates are preferably trapezoidal in shape. This shape is particularly provided to accommodate and conform to the particular shape of trapezoidal test slides 70 also formed in accordance with the present invention. The trapezoidal test slides 70 include a wider outer edge 68 and a narrower, opposite inner edge 80, and opposite lateral edges 72 which mutually converge toward the narrower inner edge 80. Preferably formed in the lateral edges 72 of the test slides 70, near the narrower inner edge 80, are recesses 74 which are preferably angled inwardly of each test slide toward the narrower inner edge 80. The purpose of these recesses 74 is to allow the entire stack of reagent test slides 70, held in place by the retaining clip, to be inserted into a slide injector mechanism of the chemical analyzer, which injector mechanism includes opposite, preferably dovetailed, vertical members, as will be described in greater detail, which are parallel to and spaced apart from one another a distance which corresponds to the width of each test slide measured laterally in proximity to the opposite recesses 74. An orientation notch 82 may be formed in one of the edges of the slides, preferably the inner or front edge 80, and is offset from the center of the edge toward one lateral side 72 or the other. As will be described in greater detail, the orientation notch 82 mates with a rib or other projection, similarly located, on the slide injector mechanism to ensure that the slides are properly oriented as they are being loaded onto the slide injector mechanism.

Each vertical member on the injector mechanism may include a resilient retainer which is received by a corresponding one of the lateral recesses 74 on the test slides 70. The retaining clip of the present invention, carrying a stack of reagent test slides, is grasped by the user at the handle and placed onto the injector mechanism of the chemical analyzer such that the opposite lateral edges 72 of the slides are facing the parallel, vertically upstanding members of the injector mechanism. The retaining clip, with its stack of reagent test slides 70, is pushed forward onto the injector mechanism such that the opposite resilient retainers on the vertical members engage and are received by the recesses 74 formed in the test slides 70. Alternatively, because the vertical members of the injector mechanism may be free standing, the entire stack of slides held by the retaining clip may be inserted onto the injector mechanism from above the members.

It should be noted that since each test slide 70 has the same configuration, the recesses 74 of the test slides are aligned as grooves on opposite sides of the stack. The resilient retainers of the vertical members of the injector mechanism are received by these grooves defined by the recesses 74 and hold the entire stack of reagent test slides 70 in place between the vertical members. The user now firmly grasps the retaining clip of the present invention and pulls backwardly, away from the injector mechanism and the upstanding, vertical members. The elastic band used in certain embodiments, or the retaining clip itself, has sufficient resiliency to allow the entire stack to be longitudinally displaced from between the top and bottom cover plates and removed from the retaining clip. The grooves formed in the top and bottom cover plates retain the elastic band in place on the retaining clip while the stack of reagent test slides 70 is being removed therefrom. Accordingly, the retaining clip of the present invention allows an entire stack of reagent test slides 70 to be inserted in the chemical analyzer without the need for the user to handle individual test slides. The retaining clip of the present invention facilitates loading test slides into the chemical analyzer and minimizes any possible contamination from the user touching the film portion of the test slides or from the environment.

The particular injector mechanism described above is disclosed with particularity in U.S. Provisional Application Ser. No. 60/526,884, filed on Dec. 4, 2003, and entitled "Reagent Test Slide Injector Mechanism Having a Scotch Drive and Rotatable Turntable Having a Geneva Drive for a Chemical Analyzer," the disclosure of which is incorporated herein by reference. Additionally, the preferred form of the chemical reagent test slides is disclosed with particularity in U.S. Provisional Application Ser. No. 60/526,885, filed on Dec. 4, 2003, and entitled "Retaining Clip for Reagent Test Slides", the disclosure of which is incorporated herein by reference.

Figure 29:
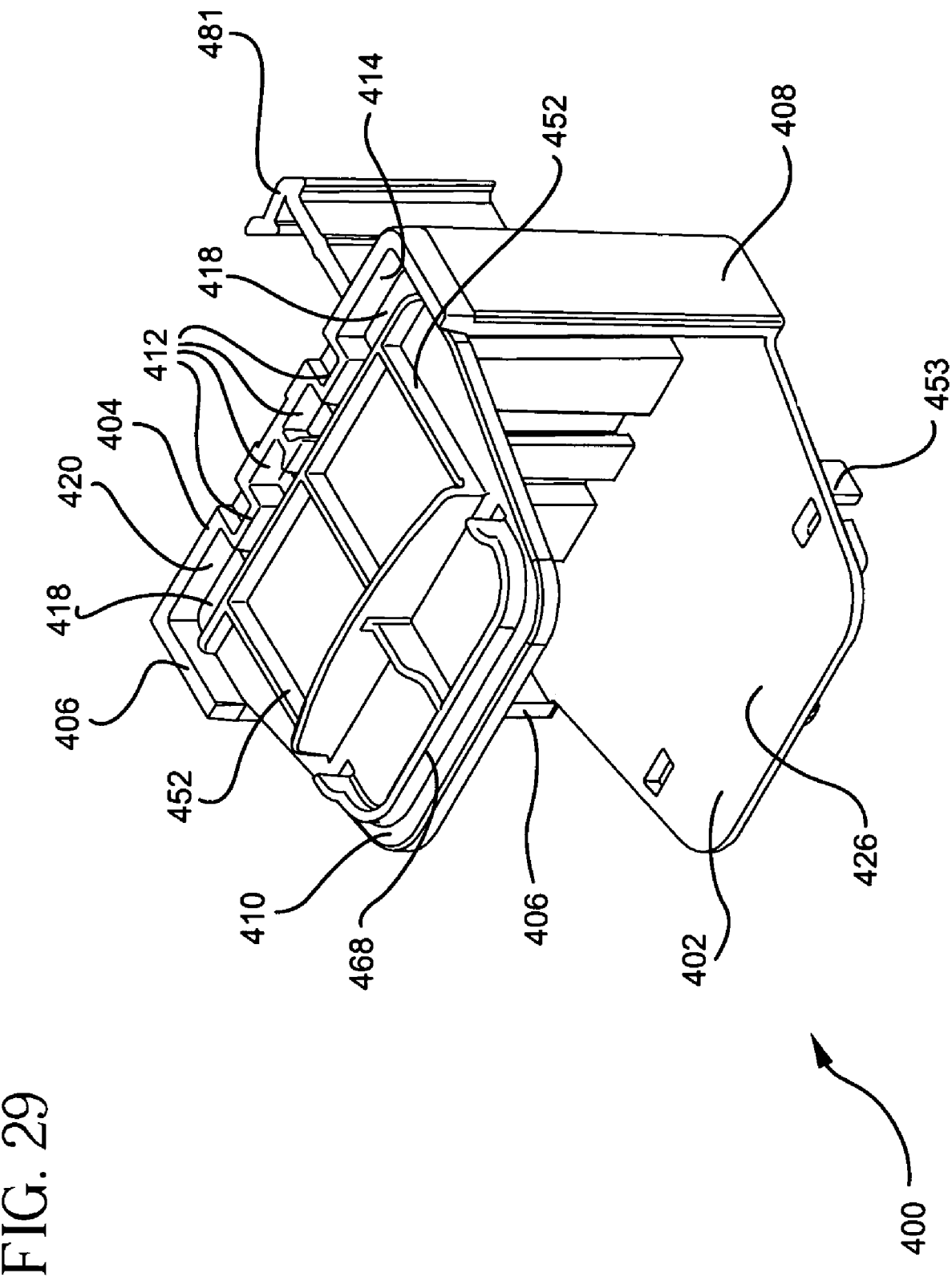
FIG. 29 is a front isometric view of a fourth embodiment of a retaining clip formed in accordance with the present invention.
Figure 30:
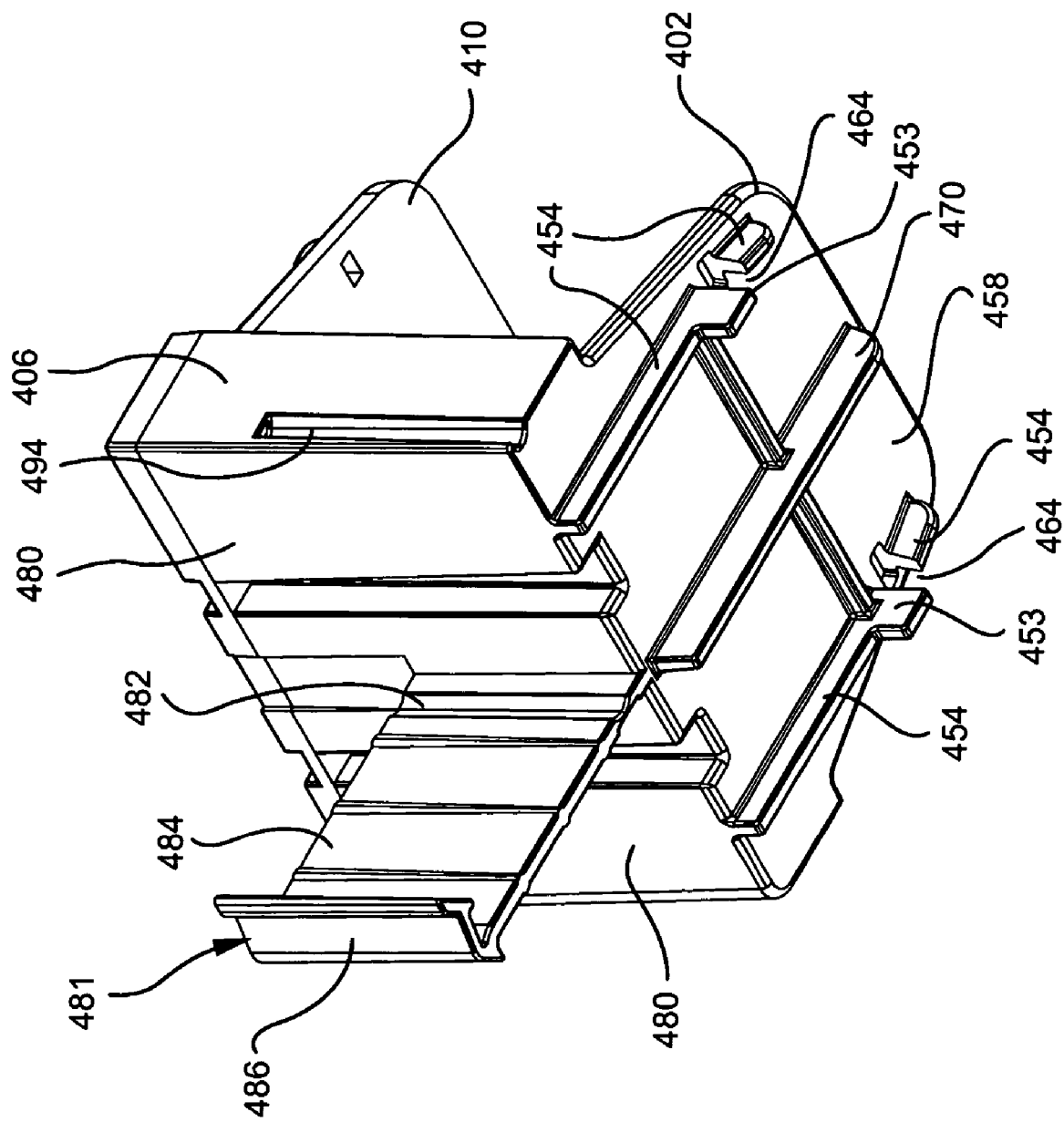
FIG. 30 is a rear isometric view of the retaining clip shown in FIG. 29.
Figure 43:
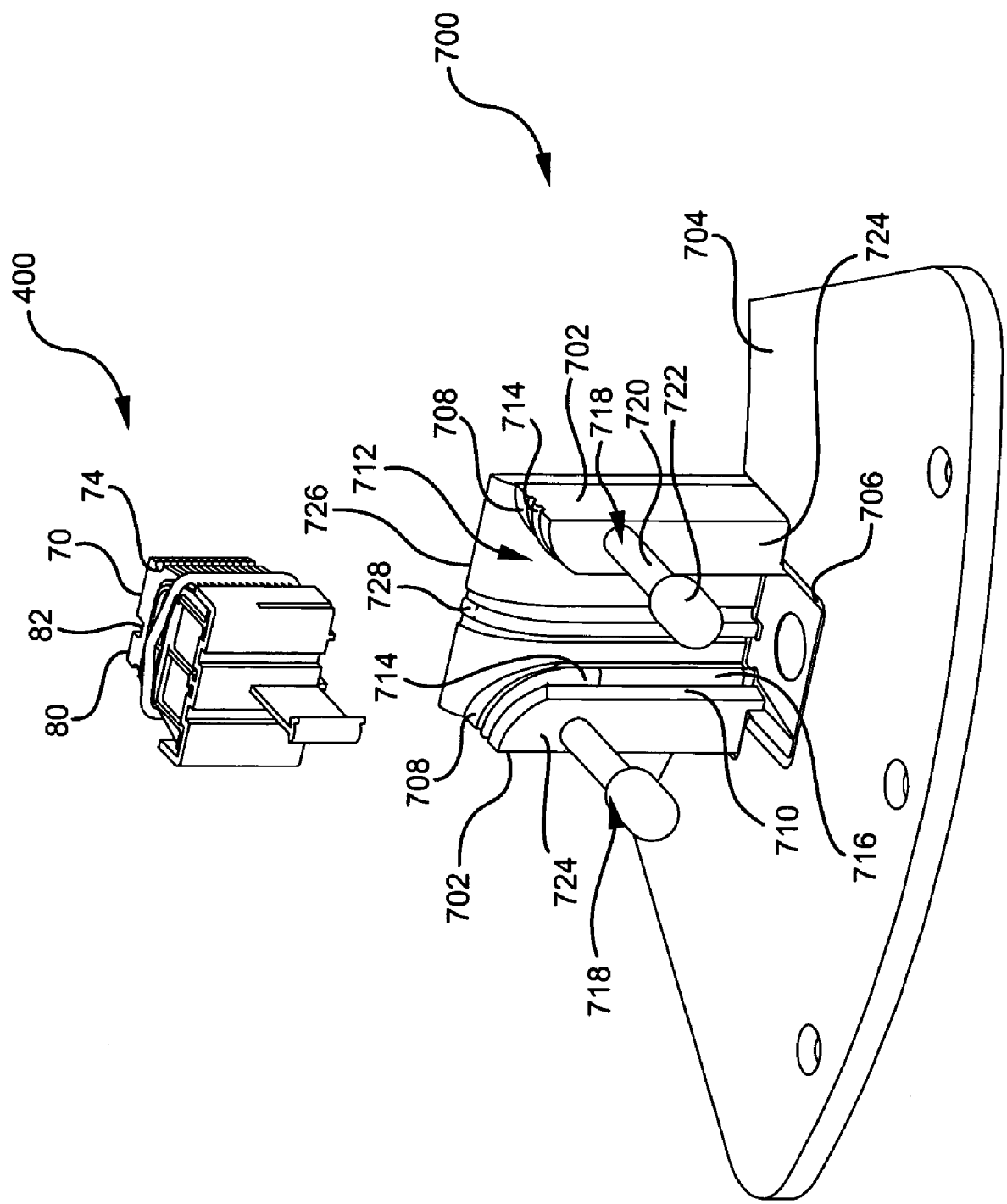
FIG. 43 is a front perspective view of a slide holder/interface and injector mechanism formed in accordance with the present invention, and showing the slide retaining clip of FIG. 29 cooperating therewith.

FIG. 43 illustrates in greater detail a slide injector mechanism 700 formed in accordance with the present invention and which includes structural components that interface with the test slides 70 to help remove the slides, in a stacked arrangement, from the retaining clip of the present invention, such as that shown in FIG. 29. The slide injector mechanism 700 includes a pair of spaced apart, upstanding, vertically disposed guide blocks 702 between which a stack of reagent test slides 70 is placed. The upstanding guide blocks 702 are mounted perpendicularly on a support plate 704 through which an opening 706 is formed which is suitably dimensioned to receive therethrough individual reagent test slides 70 from the stack of slides held in place between the upstanding guide blocks 702, with the guide blocks being positioned on the support plate 704 on opposite lateral sides of the plate opening 706. The actual mechanism for moving the individual test slides as they pass through the plate opening 706 to other stages of the chemical analyzer, such as a sample depositing stage or a rotatable turntable, is not shown or described herein, as any number of mechanisms may be employed, as would be well known to one skilled in the art, for example, a solenoid driven, reciprocatingly movable push rod or plate mounted under the support plate that engages the slides as they pass through the opening.

Each upstanding guide block 702 has a top surface 708, and an inner surface 710 which faces that of the other block. Portions of the top surfaces 708 and facing inner surfaces 710 of the guide blocks 702 may be inwardly curved to define a widened space 712 between the guide blocks 702 at their upper portions to help guide from above the blocks the insertion of a stack of reagent test slides 70 carried by the retaining clip between the blocks. Preferably, each facing inner surface 710 of the guide blocks 702 includes a rib 714 projecting outwardly therefrom which extends along the length thereof. The ribs 714 are spaced apart from each other a predetermined distance such that they closely engage and are at least partially received by corresponding recesses 74 formed in the opposite lateral edges 72 of the test slides 70 held in a stacked arrangement by the retaining clip, or individual test slides that are inserted by the user between the guide blocks 702.

A portion 716 of the length of the ribs 714, or the entire length thereof, may be formed of a resilient material, such as plastic or metal, so as to be flexible in a transverse direction with respect to the inner facing surfaces 710 of the guide blocks 702. Such resilient rib portions 716 allow the user to load a stack of test slides 70 held in place by the retaining clip, or individual test slides, onto the slide injector mechanism 700 from the front of the mechanism (as well as from atop the guide blocks 702) by pushing the slides forward between the guide blocks 702 until the resilient portions 716 of the ribs snap into the recesses 74 formed in the lateral edges 72 of the slides. The resiliency of the rib portions 716 may be unidirectional only, in the same forward direction of movement of the slides as they are being inserted between the guide blocks 702, so that the slides 70 are captively received and held between the blocks once the resilient rib portions 716 snap into the slide recesses 74. Alternatively, the resilient rib portions 716 may be flexible transversely bi-directionally, as long as the force required to unload the stack of slides from the retaining clip is not greater than the holding force that the resilient rib portions 716 imparts on the test slides.

The slide injector mechanism 700 further includes posts 718 (generally referred to as slide retaining clip disengagement members) having shank portions 720 (generally referred to as first extended portions) and enlarged, bulbous free ends 722 (generally referred to as transverse end portions) extending perpendicularly outwardly from the front face 724 of each guide block 702 in the same parallel direction. The distance between the shank portions 720 of the posts 718 is equal to or slightly greater than the width of the retaining clip so that the retaining clip may be received between the posts 718 and guided thereby, as the user loads a stack of test slides 70 held thereby from atop the guide blocks 702. The posts 718 are situated on the guide blocks 702 a distance above the support plate 704 that is at least slightly greater than the overall height of the retaining clip. Positioning and spacing the posts 718 as described above will prevent the user from inadvertently removing the retaining clip at the upper portions of the guide blocks 702, where the spacing 712 between the blocks is wider. At the upper portions of the guide blocks 702, the recesses 74 formed in the lateral edges of the test slides 70 held by the retaining clip, especially for those slides toward the top of the stacked arrangement of slides, may not fully engage the projecting ribs 714, and, therefore, some slides may remain secured to the retaining clip as it is pulled away from the slide injector mechanism 700 when the user is unloading the slides. However, with the posts 718 and the enlarged post ends 722, the user is prevented from prematurely withdrawing the retaining clip from the slide injector mechanism 700 until the retaining clip fully passes below the lowermost part of the enlarged post ends 722. This structure ensures that the projecting ribs 714 of the guide blocks 702 fully and securely engage the stacked arrangement of slides at the slide recesses 74, which occurs at the lower portion of the guide blocks 702, before the user is permitted to withdraw the retaining clip from the slide injector mechanism.

If only a portion 716 of each projecting rib 714 is made resilient, then that resilient portion 716 is preferably situated approximately above the top surface of the support plate 704 and below the lowermost extent of the enlarged ends 722 of the posts 718. In this manner, the user, when unloading the slides from the retaining clip at the front of the slide injector mechanism, can only do so if he positions the retaining clip below the posts where the ribs are resilient. It should be realized, however, that structure other than posts with enlarged ends may be used to ensure the proper positioning of the retaining clip on the slide injector mechanism. For example, L-shaped brackets (not shown) extending outwardly from the front face 724 of the guide blocks 702 may be used in lieu of the posts 718. The L-shaped brackets would be arranged in mirrored symmetry, with their shorter legs directed toward each other and spaced apart a distance sufficient to allow the handle of the retaining clip to pass therebetween. The L-shaped brackets would help guide the retaining clip into proper position on the slide injector mechanism 700 and, like the posts 718 mentioned previously, would be positioned above the top surface of the support plate 704 a predetermined distance that would prevent the user from withdrawing the retaining clip prior to the test slides in the stacked arrangement being fully engaged by the resilient rib portions 716 situated at the lower portions of the guide blocks 702.

The user would grasp the handle of the retaining clip and insert the entire stack of slides held thereby onto the slide injector 700 between the two guide blocks 702, either by sliding the stack of slides between the two blocks from atop the blocks 702, or by pushing the retaining clip forward until the recesses 74 in the lateral edges of the slides 70 in the stack engage the resilient portions 716 of the projecting ribs 714. Preferably, the user will hear an audible click from the resilient ribs 716 snapping into the slide recesses 74 and will know that the test slides, still held by the retaining clip, are properly mounted in place on the slide injector mechanism. The user may now pull backward on the handle of the retaining clip, and the entire stack of slides held thereby will be removed from the retaining clip, as they are now held in place on the slide injector mechanism.

If desired, the slide injector mechanism may include a back plate 726 situated opposite the front faces 724 of the guide blocks 702 and extending across the separation between the guide blocks. The back plate 726 may include another rib 728 extending outwardly perpendicularly from an exposed surface thereof toward the spacing between the guide posts 702 and longitudinally along the length thereof. This rib 728 is preferably not centered between the guide blocks 702, but rather is offset toward one guide block or the other. The rib 728 is aligned with and, therefore, is received by the orientation notches 82 formed in the opposite inner edge 80 of the test slides to ensure that the slides are properly oriented as they are being loaded onto the slide injector mechanism 700. If the slides 70 are being inserted on the slide injector mechanism upside down, the rib 728 will not be in alignment with the orientation notches 82 of the slides and will not be received thereby. The height of the rib 728 above the exposed surface of the back plate 726 is such that, when the slides are improperly oriented, the rib 728 engages the un-notched portion of the inner edge 80 of the slides 70 and prevents the recesses 74 from receiving the projecting ribs 714 of the guide blocks 702. Accordingly, the stack of slides 70 will be prevented from being unloaded from the retaining clip if the slides are in an improper orientation.

It should be further noted that either the top cover plate or the bottom cover plate, or both, are preferably dimensioned so that they entirely cover the film portion 73 of the top and bottom end slides in the stack, but also have a width which is less than the width of the test slides measured across the slides between the recesses 74 formed in the opposite lateral edges 72 so that at least portions of the lateral edges of the slides bearing the recesses 74 extend beyond the lateral sides of the top and bottom cover plates to expose the recesses 74 and so that the recesses 74 may cooperate with and receive portions of the upstanding vertical members of the slide injector mechanism while the test slides are still retained by the retaining clip. As mentioned previously, the top and bottom cover plates also preferably do not cover an orientation notch 82 formed in the front edge 80 of the test slides 70, so that the orientation notch 82 which is offset to one lateral side 72 or the other, will be exposed to engage a cooperating orientation rib 728 of the slide injector mechanism.

There are a number of advantages with the retaining clip of the present invention. There are no dividers between each test slide in the stack. Therefore, the retaining clip of the present invention may handle a greater density of test slides in a smaller space. Alternatively, "dummy" slides could be used to separate slides that may cross-contaminate. It is preferred, however, that the same or compatible dry analyte slides are used in the stack to prevent cross-contamination and mixing of dry analytes between adjacent test slides.

Also, as previously mentioned, the top and bottom cover plates of most of the preferred embodiments of the retaining clip cover the film portion of the top and bottom slides in the stack. The middle slides are, of course, protected from the environment by the top and bottom slides and their next adjacent slides in the stack. This minimizes air exposure and contamination of the slides and increases their shelf life. It is preferred, however, that the retaining clip with a pre-mounted stack of slides held in place is encapsulated in an air tight (low permeability) plastic or foil enclosure.

The retaining clip of the present invention is easy to mold by injection molding or other methods. This decreases the cost of manufacture of the retaining clip. Also, because the retaining clip of the present invention can accommodate different height stacks in one retaining clip, fewer retaining clips of different sizes are required, which also decreases the cost of the molding process. Nevertheless, it may be desired to manufacture retaining clips with different heights to accommodate different numbers of reagent test slides. For the embodiments shown in FIGS. 1-34, it should be realized that the sliding top cover plate assembly advantageously may be used with its cooperating portions of the retaining clip having various heights.

The retaining clip of the present invention allows a single slide from the stack, or the entire stack, to be loaded into the chemical analyzer. Only one motion is required, which simplifies the loading process and minimizes the loading time, which has the further benefit of minimizing any likelihood of exposure of the test slides to contaminants in the environment. Further, there is no need for the user to handle individual test slides, which further minimizes the chance that the film portion may be inadvertently touched and contaminated.

The top and bottom cover plates of most if not all of the embodiments described previously preferably exert a uniform and constant sealing force on the test slides within the stack. This increases the shelf life of the test slides prior to their use.

Also, because either the top or bottom or both top and bottom cover plates in several of the embodiments are movable relative to each other, stacks of varying number of test slides may be accommodated by a single retaining clip, and fewer retaining clips to accommodate the required number of test slides for a chemical analyzer are required which, of course, leads to the need for fewer stock keeping units (sku's) in the manufacturer's database.

Since the retaining clips of the present invention may accommodate stacks of varying number of test slides, the retaining clips may be used with stacks of different dry analyte slides. In other words, certain tests may require more of one reagent type of test slide than another reagent type. The same retaining clip may be used to accommodate eight calcium test slides or twelve ammonia test slides, or a mix of various chemistries for example. The first stack of calcium test slides may be loaded onto the injector mechanism of the chemical analyzer from the first retaining clip, and the second stack of ammonia test slides may be loaded on top of the first stack on the injector mechanism from the second retaining clip. This allows batching of test slides in the chemical analyzer without the need for the user to handle test slides individually. Thus, the retaining clip is perfectly adaptable to accommodate different sized stacks of test slides.

Also, the particular trapezoidal shape of the test slides, as well as the conforming shape of the retaining clip top and bottom cover plates, permit individual slides or the entire stack of slides to be removed from the retaining clip with ease. The trapezoidal shape of the test slides, with the recesses formed in the side edges of the test slides, cooperate with and allow the injector mechanism to unload the slides from the retaining clip and hold the test slides securely in place in a stack. Furthermore, there is a noticeable audible click (from the resilient retainers snapping into the slide recesses) when the test slides are removed from the retaining clip and properly secured on the injector mechanism, which alerts the user that proper loading of the test slides on the chemical analyzer has occurred. The particular trapezoidal shape of the test slides allows a greater number of test slides to be loaded on a rotatable turntable of the chemical analyzer planarly, in a side-by-side configuration, such as shown in the previously mentioned Heidt et al. patents.

The retaining clip of the present invention is also easy to manufacture, as there are no critical dimensions required, other than ensuring that the length of the top and bottom cover plates fully cover the film portion of the test slides. Furthermore, the built in handle facilitates the use and handling of the test slides.

The retaining clip of the present invention is a disposable unit which may be recycled. It further may include an RFID (radio frequency identification) or bar code situated in several suitable locations, including its top and bottom cover plates, or more preferably, on the handle thereof, to identify the type of test slides which are being loaded onto the chemical analyzer. The RFID or bar code is sensed by the chemical analyzer, which provides such information to the electronic circuit and software of the analyzer.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. In combination:
   a plurality of reagent test slides, each reagent test slide of the plurality of reagent test slides including a frame and a film portion, the frame surrounding and supporting the film portion; and
   a retaining clip for retaining the plurality of reagent test slides in a stacked arrangement, which comprises:
   a middle plate having a first side and a second side opposite the first side, the middle plate having a slot formed through the thickness thereof;
   a first cover plate at least partially received by the slot of the middle plate and being slidable therein, the first cover plate extending transversely to and outwardly from the first side of the middle plate;
   a second cover plate, the second cover plate being joined to the middle plate and extending transversely to and outwardly from the first side of the middle plate, the first cover plate and the second cover plate being in overlying relationship with each other to define therebetween a space for receiving the plurality of reagent test slides in the stacked arrangement, the slot formed in the middle plate having an elongated length and extending along its elongated length in a direction towards the second cover plate, the slot further having a width which is narrower than the elongated length of the slot, the first cover plate being slidable in the slot along the elongated length thereof in a sliding direction towards the second cover plate.

2. A combination as defined by claim 1, wherein the retaining clip further comprises:
   opposite lateral side walls, the opposite lateral side walls being joined to the middle plate and extending transversely to and outwardly from the first side of the middle plate, the opposite lateral side walls together with the first cover plate and the second cover plate defining the space for receiving the plurality of reagent test slides in the stacked arrangement.

3. A combination as defined by claim 1, wherein each reagent test slide of the plurality of reagent test slides includes opposite lateral edges and a recess formed in each lateral edge, and wherein the width of the first cover plate and the width of the second cover plate are less than the width of each reagent test slide of the plurality of reagent test slides measured between the recesses formed in the lateral edges thereof so that the first and second cover plates do not overlie the recesses formed in the lateral edges of each reagent test slide of the plurality of reagent slides.

4. A combination as defined by claim 1, wherein the retaining clip further comprises:
 a foldable handle, the foldable handle being pivotally joined to the middle plate on the second side thereof; and
 a hinge pivotally joining the foldable handle to the middle plate.

5. A combination as defined by claim 4, wherein the hinge of the retaining clip includes a living hinge, the living hinge being connected to the foldable handle and the middle plate to allow the handle to pivot with respect to the middle plate.

6. A combination as defined by claim 1, wherein the first cover plate of the retaining clip includes an extended portion having a T-shape and which extends through the slot of the middle plate and outwardly from the second side of the middle plate.

7. A combination as defined by claim 1, wherein the retaining clip further comprises:
 a restraining band, the restraining band encircling the first cover plate and the second cover plate and the space defined by the first cover plate and the second cover plate for receiving the plurality of reagent test slides in the stacked arrangement.

8. A combination as defined by claim 7, wherein at least one of the first cover plate and the second cover plate of the retaining clip includes structure defining a groove for at least partially receiving the restraining band.

9. In combination:
 a plurality of reagent test slides, each reagent test slide of the plurality of reagent test slides including a frame and a film portion, the frame surrounding and supporting the film portion; and
 a retaining clip for retaining the plurality of reagent test slides in a stacked arrangement, which comprises:
  a middle plate having a first side and a second side opposite the first side;
  a first cover plate slidably mounted on the middle plate and extending transversely to and outwardly from the first side of the middle plate;
  a second cover plate, the second cover plate being joined to the middle plate and extending transversely to and outwardly from the first side of the middle plate, the first cover plate and the second cover plate being in overlying relationship with each other to define therebetween a space for receiving the plurality of reagent test slides in the stacked arrangement, the first cover plate being continuously slidable on the middle plate in a direction toward the second cover plate; and
  means for slidably mounting the first cover plate on the middle plate, the first cover plate being slidable on the middle plate in a direction toward the second cover plate.

10. A combination as defined by claim 9, wherein the retaining clip further comprises:
 opposite lateral side walls, the opposite lateral side walls being joined to the middle plate and extending transversely to and outwardly from the first side of the middle plate, the opposite lateral side walls together with the first cover plate and the second cover plate defining the space for receiving the plurality of reagent test slides in the stacked arrangement.

11. A combination as defined by claim 9, wherein the means for slidably mounting the first cover plate on the middle plate of the retaining clip includes a T-shaped rail extending outwardly from the first side of the middle plate and in a direction between the first cover plate and the second cover plate; and wherein the first cover plate includes means for defining a T-shaped slot situated thereon, the T-shaped rail of the middle plate being receivable by the T-shaped slot of the first cover plate to slidably mount the first cover plate to the middle plate.

12. A combination as defined by claim 11, wherein the first cover plate of the retaining clip includes a main body portion; and wherein the means for defining a T-shaped slot of the retaining clip includes a first L-shaped leg extending co-planarly from the main body portion of the first cover plate and a second L-shaped leg extending co-planarly from the main body portion of the first cover plate and in the same direction as the first L-shaped leg, the first L-shaped leg and the second L-shaped leg being spaced apart from one another to define therebetween the T-shaped slot for receiving the T-shaped rail of the middle plate.

13. A combination as defined by claim 9, wherein the retaining clip further comprises:
 a plurality of guide plates, each guide plate of the plurality of guide plates being joined to the middle plate and extending transversely to and outwardly from the first side of the middle plate and further extending in a direction between the first cover plate and the second cover plate.

14. A combination as defined by claim 9, wherein the retaining clip further comprises:
 a foldable handle, the foldable handle being pivotally joined to the middle plate on the second side thereof; and
 a hinge pivotally joining the foldable handle to the middle plate.

15. A combination as defined by claim 14, wherein the hinge of the retaining clip includes a living hinge, the living hinge being connected to the foldable handle and the middle plate and allowing the foldable handle to pivot with respect to the middle plate.

16. In combination:
 a plurality of reagent test slides, each reagent test slide of the plurality of reagent test slides including a frame and a film portion, the frame surrounding and supporting the film portion; and
 a retaining clip for retaining the plurality of reagent test slides in a stacked arrangement, which comprises:
  a middle plate having a first side and a second side opposite the first side;
  a first cover plate slidably mounted on the middle plate and extending transversely to and outwardly from the first side of the middle plate;
  a second cover plate, the second cover plate being joined to the middle plate and extending transversely to and outwardly from the first side of the middle plate, the first cover plate and the second cover plate being in overlying relationship with each other to define therebetween a space for receiving the plurality of reagent test slides in the stacked arrangement, the first cover plate being continuously slidable on the middle plate in a direction toward the second cover plate;
  means for slidably mounting the first cover plate on the middle plate;
  a foldable handle, the foldable handle being pivotally joined to the middle plate on the second side thereof;
  a hinge pivotally joining the foldable handle to the middle plate; and
  opposite lateral side walls, the opposite lateral side walls being joined to the middle plate and extending transversely to and outwardly from the first side of the middle plate, the opposite lateral side walls together with the first cover plate and the second cover plate defining the space for receiving the plurality of reagent test slides; and wherein at least one of the opposite lateral side walls includes a bead extending outwardly therefrom, the foldable handle including a resilient portion for engaging the bead of the at least one lateral side wall to selectively retain the foldable handle in a folded position in proximity to the second side of the middle plate.

17. In combination:
a plurality of reagent test slides, each reagent test slide of the plurality of reagent test slides including a frame and a film portion, the frame surrounding and supporting the film portion; and
a retaining clip for retaining the plurality of reagent test slides in a stacked arrangement, which comprises:
a middle plate having a first side and a second side opposite the first side;
a first cover plate slidably mounted on the middle plate and extending transversely to and outwardly from the first side of the middle plate;
a second cover plate, the second cover plate being joined to the middle plate and extending transversely to and outwardly from the first side of the middle plate, the first cover plate and the second cover plate being in overlying relationship with each other to define therebetween a space for receiving the plurality of reagent test slides in the stacked arrangement, the first cover plate being continuously slidable on the middle plate in a direction toward the second cover plate;
means for slidably mounting the first cover place on the middle plate;
a foldable handle, the foldable handle being pivotally joined to the middle plate on the second side thereof;
a hinge pivotally joining the foldable handle to the middle plate; and
opposite lateral side walls, the opposite lateral side walls being joined to the middle plate and extending transversely to and outwardly from the first side of the middle plate, the opposite lateral side walls together with the first cover plate and the second cover plate defining the space for receiving the plurality of reagent test slides; and wherein at least one of the opposite lateral side walls has formed in a surface thereof a groove, the foldable handle including a resilient portion for engaging and being received by the groove of the at least one lateral side wall to selectively retain the foldable handle in a folded position in proximity to the second side of the middle plate.

18. A combination as defined by claim 9, wherein each reagent test slide of the plurality of reagent test slides includes opposite lateral edges and a recess formed in each lateral edge, and wherein the width of the first cover plate and the width of the second cover plate are less than the width of each reagent test slide of the plurality of reagent test slides measured between the recesses formed in the lateral edges thereof so that the first and second cover plates do not overlie the recesses formed in the lateral edges of each reagent test slide of the plurality of reagent slides.

19. A combination as defined by claim 9, wherein the retaining clip further comprises:
a restraining band, the restraining band encircling the first cover plate and the second cover plate and the space defined by the first cover plate and the second cover plate for receiving the plurality of reagent test slides in the stacked arrangement.

20. A combination as defined by claim 19, wherein at least one of the first cover plate and the second cover plate of the retaining clip includes structure defining a groove for at least partially receiving the restraining band.

21. A combination as defined by claim 12, wherein the middle plate of the retaining clip includes undulations which define at least one recess formed in the first side of the middle plate and extending toward the second side and in a direction between the first cover plate and the second cover plate, and at least one projecting guide structure extending outwardly towards the space for receiving the plurality of reagent test slides and in a direction between the first cover plate and the second cover plate; wherein the first cover plate further includes at least one tab, the at least one tab being slidably received by the at least one recess of the middle plate; and wherein the main body portion of the first cover plate includes an exposed edge and at least one recess formed in the exposed edge, the at least one recess of the main body portion of the first cover plate slidably receiving the at least one projecting guide structure, the at least one tab and the at least one recess of the first cover plate cooperating respectively with the at least one projecting guide structure and the at least one recess of the middle plate to minimize lateral movement of the first cover plate with respect to the middle plate.

22. A combination as defined by claim 1, wherein each of the first and second cover plates of the retaining clip is solid and non-apertured through the thickness thereof.

23. A combination as defined by claim 9, wherein each of the first and second cover plates of the retaining clip is solid and non-pertured through the thickness thereof.

24. In combination:
a plurality of reagent test slides, each reagent test slide of the plurality of reagent test slides including opposite lateral edges and a recess formed in each lateral edge, each reagent test slide having a first width measured between the recesses formed in the opposite lateral edges of the reagent test slide; and
a retaining clip for retaining the plurality of reagent test slides in a stacked arrangement, the retaining clip comprising:
a middle plate having a first side and a second side opposite the first side, the middle plate having a slot formed through the thickness thereof;
a first cover plate at least partially received by the slot of the middle plate and being slidable therein, the first cover plate extending transversely to and outwardly from the first side of the middle plate, the first cover plate residing generally in a first plane, the first cover plate including opposite lateral edges and having a second width measured between the opposite lateral edges of the first cover plate; and
a second cover plate, the second cover plate being joined to the middle plate and extending transversely to and outwardly from the first side of the middle plate, the second cover plate residing generally in a second plane which is substantially parallel to the first plane, the second cover plate including opposite lateral edges and having a third width measured between the opposite lateral edges of the second cover plate, the first cover plate and the second cover plate being in overlying relationship with each other to define therebetween a space for receiving the plurality of reagent test slides in a stacked arrangement, the slot formed in the middle plate having an elongated length and extending along its elongated length in a direction towards the second cover plate, the slot residing generally in a third plane which is oriented to be transverse to the first and second planes in which the first and second cover plates respectively generally reside, the first cover plate being slideable in the slot along the elongated length thereof in a sliding direction towards the second cover plate, the second width of the first cover plate and the third width of the second cover plate being less than the first width of each reagent test slide of the plurality of reagent test slides so that the first and second cover plates do not overlie the recesses formed in the lateral edges of each reagent test slide of the plurality of reagent test slides.

25. In combination:
a plurality of reagent test slides, each reagent test slide of the plurality of reagent test slides including opposite lateral edges and a recess formed in each lateral edge, each reagent test slide having a first width measured between the recesses formed in the opposite lateral edges of the reagent test slide; and
a retaining clip for retaining the plurality of reagent test slides in a stacked arrangement, the retaining clip comprising:
   a middle plate having a first side and a second side opposite the first side;
   a first cover plate slidably mounted on the middle plate and extending transversely to and outwardly from the first side of the middle plate, the first cover plate residing generally in a first plane, the first cover plate including opposite lateral edges and having a second width measured between the opposite lateral edges of the first cover plate;
   means for slidably mounting the first cover plate on the middle plate; and
   a second cover plate, the second cover plate being joined to the middle plate and extending transversely to and outwardly from the first side of the middle plate, the second cover plate residing generally in a second plane which is substantially parallel to the first plane, the second cover plate including opposite lateral edges and having a third width measured between the opposite lateral edges of the second cover plate, the first cover plate and the second cover plate being in overlying relationship with each other to define therebetween a space for receiving the plurality of reagent test slides in a stacked arrangement, the first cover plate being continuously slidable on the middle plate towards the second cover plate in a third plane which is transverse to the first and second planes in which the first and second cover plates respectively generally reside, the second width of the first cover plate and the third width of the second cover plate being less than the first width of each reagent test slide of the plurality of reagent test slides so that the first and second cover plates do not overlie the recesses formed in the lateral edges of each reagent test slide of the plurality of reagent test slides.

26. In combination:
a plurality of reagent test slides, each reagent test slide of the plurality of reagent test slides including opposite lateral edges and a recess formed in each lateral edge, each reagent test slide having a first width measured between the recesses formed in the opposite lateral edges of the reagent test slide; and
a retaining clip for retaining the plurality of reagent test slides in a stacked arrangement, the retaining clip comprising:
   a middle plate having a first side and a second side opposite the first side, the middle plate including a T-shaped rail extending outwardly from the first side thereof and having an elongated length;
   a first cover plate slidably mounted on the middle plate, the first cover plate including means for defining a T-shaped slot situated thereon, the T-shaped rail of the middle plate being receivable by the T-shaped slot of the first cover plate to slidably mount the first cover plate on the middle plate, the first cover plate extending transversely to and outwardly from the first side of the middle plate, the first cover plate residing generally in a first plane, the first cover plate including opposite lateral edges and having a second width measured between the opposite lateral edges of the first cover plate; and
   a second cover plate, the second cover plate being joined to the middle plate and extending transversely to and outwardly from the first side of the middle plate, the second cover plate residing generally in a second plane which is substantially parallel to the first plane, the second cover plate including opposite lateral edges and having a third width measured between the opposite lateral edges of the second cover plate, the first cover plate and the second cover plate being in overlying relationship with each other to define therebetween a space for receiving the plurality of reagent test slides in a stacked arrangement, the T-shaped rail of the middle plate extending along its elongated length in a direction towards the second cover plate, the T-shaped rail residing generally in a third plane which is oriented to be transverse to the first and second planes in which the first and second cover plates respectively generally reside, the first cover plate being slidable on the T-shaped rail along the elongated length thereof in a sliding direction towards the second cover plate, the second width of the first cover plate and the third width of the second cover plate being less than the first width of each reagent test slide of the plurality of reagent test slides so that the first and second cover plates do not overlie the recesses formed in the lateral edges of each reagent test slide of the plurality of reagent test slides.

27. A combination as defined by claim 26, wherein the first cover plate of the retaining clip includes a main body portion; and wherein the means for defining a T-shaped slot of the retaining clip includes a first L-shaped leg extending co-planarly from the main body portion of the first cover plate and a second L-shaped leg extending co-planarly from the main body portion of the first cover plate and in the same direction as the first L-shaped leg, the first L-shaped leg and the second L-shaped leg being spaced apart from one another to define therebetween the T-shaped slot for receiving the T-shaped rail of the middle plate.

* * * * *

UNITED STATES PATENT AND TRADEMARK OFFICE
CERTIFICATE OF CORRECTION

PATENT NO. : 7,632,468 B2  Page 1 of 1
APPLICATION NO. : 11/002599
DATED : December 15, 2009
INVENTOR(S) : Barski et al.

It is certified that error appears in the above-identified patent and that said Letters Patent is hereby corrected as shown below:

On the Title Page Item [75] Inventors as follows:

Delete Item (75) and insert the following paragraph:

--Stanislaw Barski, Limerick, ME (US); Ross Bryan Goldman, Scarborough, ME (US); Carl Russell Rich, Falmouth, ME (US)--.

Signed and Sealed this

Sixteenth Day of March, 2010

David J. Kappos
*Director of the United States Patent and Trademark Office*